(12) United States Patent
Lundberg et al.

(10) Patent No.: US 12,018,054 B2
(45) Date of Patent: Jun. 25, 2024

(54) MULTIVALENT OspA POLYPEPTIDES AND METHODS AND USES RELATING THERETO

(71) Applicant: Valneva Austria GmbH, Vienna (AT)

(72) Inventors: Urban Lundberg, Pressbaum (AT);
Andreas Meinke, Pressbaum (AT);
Abhijeet Nayak, Amsterdam (NL);
Wolfgang Schüler, Vienna (AT)

(73) Assignee: Valneva Austria GmbH, Vienna (AT)

( * ) Notice: Subject to any disclaimer, the term of this patent is extended or adjusted under 35 U.S.C. 154(b) by 1260 days.

(21) Appl. No.: 16/497,178

(22) PCT Filed: Apr. 13, 2018

(86) PCT No.: PCT/EP2018/059533
§ 371 (c)(1),
(2) Date: Sep. 24, 2019

(87) PCT Pub. No.: WO2018/189372
PCT Pub. Date: Oct. 18, 2018

(65) Prior Publication Data
US 2023/0151063 A1 May 18, 2023

(30) Foreign Application Priority Data

Apr. 13, 2017 (EP) .................................. 17166483

(51) Int. Cl.
| | |
|---|---|
| A61K 39/02 | (2006.01) |
| A61K 39/39 | (2006.01) |
| A61P 31/04 | (2006.01) |
| C07K 14/20 | (2006.01) |
| A61K 39/00 | (2006.01) |

(52) U.S. Cl.
CPC .......... *C07K 14/20* (2013.01); *A61K 39/0225* (2013.01); *A61K 39/39* (2013.01); *A61P 31/04* (2018.01); *A61K 2039/55505* (2013.01); *A61K 2039/575* (2013.01); *A61K 2039/70* (2013.01); *C07K 2319/02* (2013.01); *C07K 2319/90* (2013.01)

(58) Field of Classification Search
None
See application file for complete search history.

(56) References Cited

U.S. PATENT DOCUMENTS

| | | |
|---|---|---|
| 6,248,562 B1 | 6/2001 | Dunn et al. |
| 7,008,625 B2 | 3/2006 | Dattwyler et al. |
| 8,466,259 B2 | 6/2013 | Liu et al. |
| 8,986,704 B2 | 3/2015 | Comstedt et al. |
| 9,926,343 B2 | 3/2018 | Comstedt et al. |
| 9,975,927 B2 | 5/2018 | Lundberg et al. |
| 10,406,221 B2 | 9/2019 | Leng et al. |
| 10,544,194 B2 | 1/2020 | Comstedt et al. |
| 10,766,931 B2 | 9/2020 | Lundberg et al. |
| 10,787,501 B1 | 9/2020 | Babb et al. |
| 11,208,439 B2 | 12/2021 | Comstedt et al. |
| 11,466,058 B2 | 10/2022 | Comstedt et al. |
| 11,572,392 B2 | 2/2023 | Lundberg et al. |
| 2004/0023325 A1 | 2/2004 | Luft et al. |
| 2009/0176273 A1 | 7/2009 | Leng et al. |
| 2011/0053244 A1 | 3/2011 | Oyler et al. |
| 2011/0293652 A1 | 12/2011 | Crowe et al. |
| 2014/0010835 A1 | 1/2014 | Comstedt et al. |
| 2015/0232517 A1 | 8/2015 | Comstedt et al. |
| 2015/0250865 A1 | 9/2015 | Comstedt et al. |
| 2016/0045591 A1 | 2/2016 | Campos-Neto et al. |
| 2016/0333056 A1 | 11/2016 | Lundberg et al. |
| 2017/0101446 A1 | 4/2017 | Comstedt et al. |
| 2017/0107263 A1 | 4/2017 | Comstedt et al. |
| 2017/0239340 A1 | 8/2017 | Ellingsworth et al. |
| 2018/0327460 A1 | 11/2018 | Comstedt et al. |
| 2018/0362593 A1 | 12/2018 | Lundberg et al. |
| 2020/0239525 A1 | 7/2020 | Comstedt et al. |
| 2021/0054032 A1 | 2/2021 | Lundberg et al. |
| 2022/0185851 A1 | 6/2022 | Comstedt et al. |
| 2023/0173051 A1 | 6/2023 | Bézay et al. |
| 2023/0295245 A1 | 9/2023 | Comstedt et al. |
| 2023/0322869 A1 | 10/2023 | Lundberg et al. |

FOREIGN PATENT DOCUMENTS

| | | |
|---|---|---|
| CN | 103118701 A | 5/2013 |
| EP | 2753352 B1 | 1/2017 |
| EP | 2869839 B1 | 9/2018 |
| JP | 4810428 B2 | 11/2011 |
| JP | 2019-070007 A | 5/2019 |
| KR | 10-2013-0062954 A | 6/2013 |
| WO | WO 2002/016421 A2 | 2/2002 |
| WO | WO 2008/031133 A2 | 3/2008 |

(Continued)

OTHER PUBLICATIONS

Greenspan et al (Nature Biotechnology 7: 936-937, 1999).*
Chothia et al (The EMBO Journal, 1986, 5/4:823-26).*
[No Author Listed] Clinical Trials Identifier: NCT03010228. Study assessing the safety, immunogenicity and dose response of VLA15, a new vaccine candidate against Lyme borreliosis. Jan. 4, 2017. retrieved Mar. 26, 2018 from https://clinicaltrials.gov/ct2/show/study/NCT03010228.
[No Author Listed] ECDC; Meeting Report: Second expert consultation on tick-borne diseases with emphasis on Lyme borreliosis and tick-borne encephalitis, Stockholm, Sweden, Nov. 22-23, 2011.
[No Author Listed] pET System Manual. May 2003. Novagen.
[No Author Listed] Valneva Completes Recruitment for Phase 2 Studies of its Lyme Disease Vaccine Candidate VLA15. Valneva SE. Sep. 30, 2019. 3 pages.

(Continued)

*Primary Examiner* — Jennifer E Graser
(74) *Attorney, Agent, or Firm* — Wolf, Greenfield & Sacks, P.C.

(57) ABSTRACT

The present invention relates to an immunogenic polypeptide, a nucleic acid encoding the same, a pharmaceutical composition comprising the same and the immunogenic polypeptide, nucleic acid or pharmaceutical composition for use as a medicament, particularly a vaccine, or for use in a method of treating or preventing a *Borrelia* infection.

20 Claims, 10 Drawing Sheets

Figure 4:
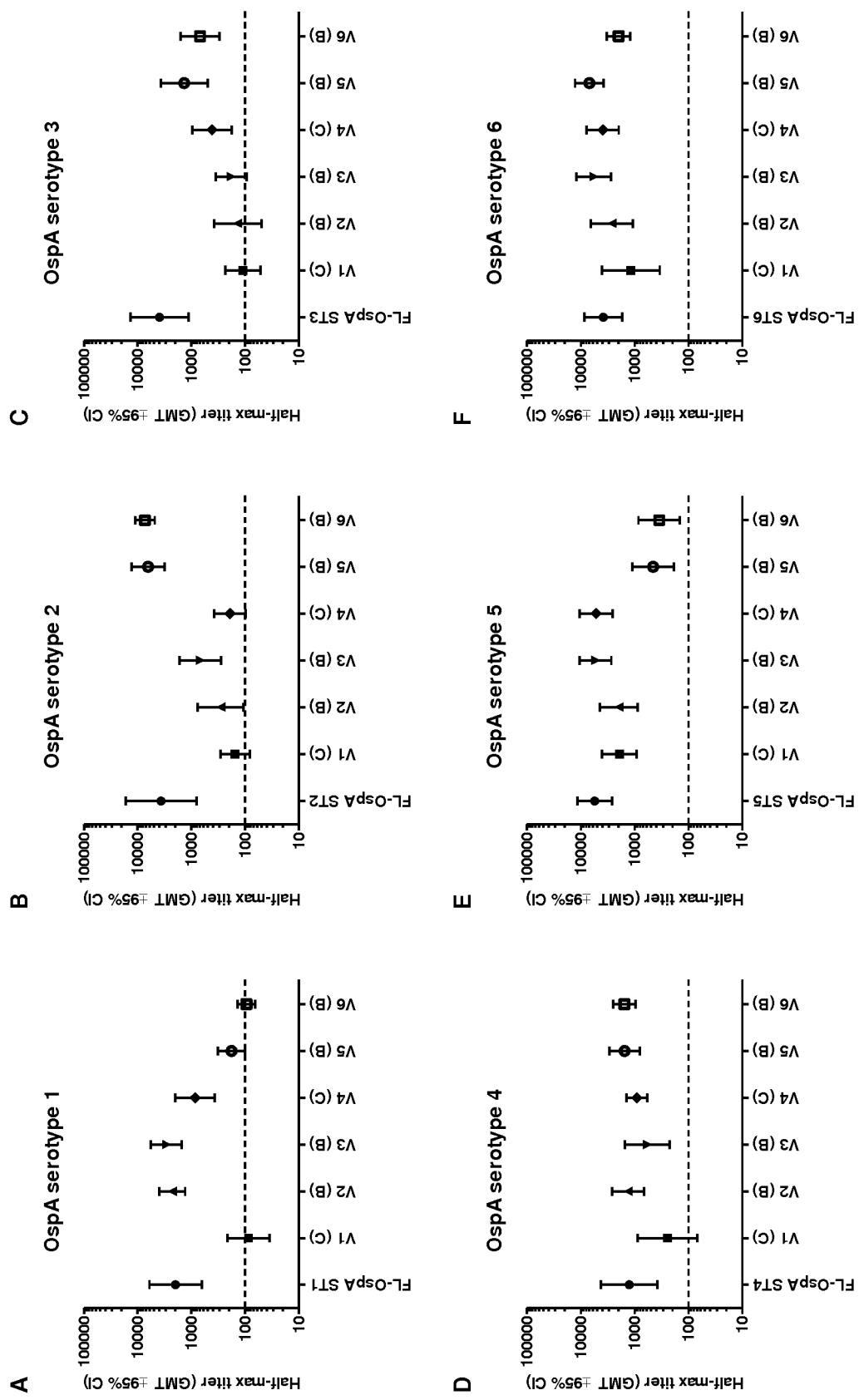

Specification includes a Sequence Listing.

(56) References Cited

FOREIGN PATENT DOCUMENTS

| WO | WO 2011/143617 A1 | 11/2011 |
|---|---|---|
| WO | WO 2011/143623 A1 | 11/2011 |
| WO | WO 2012/028741 A1 | 3/2012 |
| WO | WO 2012/066420 A1 | 5/2012 |
| WO | WO 2012/066423 A1 | 5/2012 |
| WO | WO 2013/083726 A1 | 6/2013 |
| WO | WO 2013/083729 A2 | 6/2013 |
| WO | WO 2014/006226 A1 | 1/2014 |
| WO | WO 2015/104396 A1 | 7/2015 |
| WO | WO 2015/169271 A1 | 11/2015 |
| WO | WO 2018/189372 A1 | 10/2018 |
| WO | WO 2019/092002 A1 | 5/2019 |
| WO | WO 2020/234300 A1 | 11/2020 |

OTHER PUBLICATIONS

[No Author Listed] Valneva report positive phase I interim results for its Lyme vaccine candidate VLA15. Valneva. Mar. 19, 2018.

[No Author Listed], Analysis of Fatty Acids in Infant Formulas Using an Agilent J&W HP-88 Capillary GC Column. Agilent Technologies. Jun. 17, 2011. 8 pages.

[No Author Listed], CDC provides estimate of Americans diagnosed with Lyme disease each year. CDC Press Release. Accessible at www.cdc.gov/media. 2 pages.

[No Author Listed], Lyme Borreliosis in Europe. WHO Europe. 2020. 1 page.

[No Author Listed], Lyme Disease Charts and Figures: Historical Data. Accessible at www.cdc.gov/lyme/stats/graphs.html. Retrieved on May 4, 2020. 1 page.

[No Author Listed], Press release: Valneva Reports Positive Initial Booster Data and Final Phase 1 Data for its Lyme Disease Vaccine Candidate. Jan. 31, 2019.

[No Author Listed], Report 9: Impact of non-pharmaceutical interventions (NPIs) to reduce COVID-19 mortality and healthcare demand. Imperial College COVID-19 Response Team. Mar. 16, 2020. 20 pages.

[No Author Listed], Valneva and Pfizer Report Further Positive Phase 2 Results, Including Booster Response, for Lyme Disease Vaccine Candidate. Valneva SE and Pfizer Press Release. Sep. 28, 2021. 1 page.

Altschul et al., Gapped BLAST and PSI-BLAST: a new generation of protein database search programs. Nucleic Acids Res. Sep. 1, 1997;25(17):3389-402. doi: 10.1093/nar/25.17.3389.

Altschul, et al. Basic Local Alignment Search Tool (1990) J. Mol. Biol. 215:403-410.

Andrews et al., Bacterial iron homeostasis. FEMS Microbiol Rev. Jun. 2003;27(2-3):215-37. doi: 10.1016/S0168-6445(03)00055-X.

Baker et al., Electrostatics of nanosystems: application to microtubules and the ribosome. Proc Natl Acad Sci U S A. Aug. 28, 2001;98(18):10037-41.

Barroso et al., Nucleotide sequence of Clostridium difficile toxin B gene. Nucleic Acids Res. Jul. 11, 1990;18(13):4004. doi: 10.1093/nar/18.13.4004.

Bessler et al. Synthetic lipopeptides as novel adjuvants. Res Immunol. Jun. 1992; 143(5):548-53; discussion 579-80.

Betz, Disulfide bonds and the stability of globular proteins. Protein Sci. Oct. 1993;2(10):1551-8.

Bockenstedt et al., Identification of a Borrelia burgdorferi OspA T cell epitope that promotes anti-OspA IgG in mice. J Immunol. Dec. 15, 1996;157(12):5496-502.

Bockenstedt et al., Inability of truncated recombinant Osp A proteins to elicit protective immunity to Borrelia burgdorferi in mice. J Immunol. Jul. 15, 1993;151(2):900-6.

Bouchon et al., Analysis of the lipidated recombinant outer surface protein A from Borrelia burgdorferi by mass spectrometry. Anal Biochem. Mar. 1, 1997;246(1):52-61.

Bunikis et al. A Surface-Exposed Region of a Novel Outer Membrane Protein (P66) of *Borrelia* spp. is Variable in Size and Sequence (1998) Journal of Bacteriology 180(7):1618-1623.

Caruthers et al., New chemical methods for synthesizing polynucleotides. Nucleic Acids Symp Ser. 1980;(7):215-23.

Chakrabarti et al., Dissecting Protein-Protein Recognition Sites; PROTEINS: Structure, Function, and Genetics 47:334-343 (2002).

Compton et al., Introduction of a Disulfide Bond Leads to Stabilization and Crystallization of a Ricin Immunogen (2011) Proteins 79(4):1048-1060. doi:10.1002/prot.22933.

Comstedt et al. Characterization and optimization of a novel vaccine for protection against Lyme borreliosis (2015) Vaccine 33:5982-5988.

Comstedt et al., Design and development of a novel vaccine for protection against Lyme borreliosis. PLoS One. Nov. 19, 2014;9(11):e113294. doi: 10.1371/journal.pone.0113294.

Comstedt et al., Efficacy testing of a novel OspA based Lyme borreliosis vaccine. Gordon Research Conference: "Biology of Spirochetes", Ventura, California. Jan. 19-24, 2014. Abstract.

Comstedt et al., Investigation of a vaccine targeting Lyme borreliosis in Europe. Gordon Research Conference: "Biology of Spirochetes". Ventura, California. Jan. 19-24, 2014. Abstract.

Comstedt et al., The novel Lyme borreliosis vaccine VLA15 shows broad protection against *Borrelia* species expressing six different OspA serotypes. PLoS One. Sep. 1, 2017;12(9):e0184357. doi: 10.1371/journal.pone.0184357. eCollection 2017.

Corpet, Multiple sequence alignment with hierarchical clustering. Nucleic Acids Res. Nov. 25, 1988;16(22):10881-90. doi: 10.1093/nar/16.22.10881.

Creighton et al., Mechanisms and catalysts of disulfide bond formation in proteins. Trends Biotechnol. Jan. 1995;13(1):18-23.

Crowe, A Lyme borreliosis vaccine for Europe and beyond. Climate change impact on ticks and tick-borne diseases. Brussels. Feb. 6, 2009.

Cutler, et al. Emerging borreliae—Expanding beyond Lyme borreliosis (2017) Molecular and Cellular robes 31:22e27.

Davies et al., Interactions of protein antigens with antibodies (1996) Proc. Natl. Acad. Sci. USA 93:7-12.

De Silva, et al. Borrelia burgdorferi OspA Is an Arthropod-specific Transmission-blocking Lyme Disease Vaccine (1996) J. Exp. Med. 183:271-275.

Devereux, et al. A comprehensive set of sequence analysis programs for the VAX (1984) Nucleic Acids Research 12(1):387-395.

Ding et al., Structural identification of a key protective B-cell epitope in Lyme disease antigen OspA. J Mol Biol. Oct. 6, 2000;302(5):1153-64.

Dolinsky et al., PDB2PQR: expanding and upgrading automated preparation of biomolecular structures for molecular simulations. Nucleic Acids Res. Jul. 2007;35(Web Server issue):W522-5.

Dove et al., Molecular characterization of the Clostridium difficile toxin A gene. Infect Immun. Feb. 1990;58(2):480-8. doi: 10.1128/iai.58.2.480-488.1990.

Dykhuizen et al., Borrelia burgdorferi is clonal: Implications for taxonomy and vaccine development. Proc. Natl. Acad. Sci. 1993;90:10163-7.

Edelman et al., Degeneracy and complexity in biological systems. Proc Natl Acad Sci U S A. Nov. 20, 2001;98(24):13763-8. doi: 10.1073/pnas.231499798. Epub Nov. 6, 2001.

Egan et al., Relationship between tightness of binding and immunogenicity in an aluminum-containing adjuvant-adsorbed hepatitis B vaccine. Vaccine. May 21, 2009;27(24):3175-80. doi: 10.1016/j.vaccine.2009.03.054. Epub Apr. 7, 2009.

Embers et al., Vaccination against Lyme disease: past, present, and future. Frontiers in Cellular and Infection Microbiology 2013;3(6). www.frontiersin.org. doi:10.3389/fcimb.2013.00006.

Erdile et al., Role of attached lipid in immunogenicity of Borrelia burgdorferi OspA. Infect Immun. Jan. 1993;61(1):81-90.

Fass, Disulfide bonding in protein biophysics. Annu Rev Biophys. 2012;41:63-79. doi: 10.1146/annurev-biophys-050511-102321. Epub Dec. 20, 2011.

Feng et al., Progressive sequence alignment as a prerequisite to correct phylogenetic trees. J Mol Evol. 1987;25(4):351-60. doi: 10.1007/BF02603120.

Fingerle, et al. Epidemiological aspects and molecular characterization of *Borrelia burgdorferi* s.l. from southern Germany with

(56) References Cited

OTHER PUBLICATIONS special respect to the new species *Borrelia spielmanii* sp. nov. International Journal of Medical Microbiology 2008;298:279-290. doi:10.1016/j.ijmm.2007.05.002.

Friguet et al. Measurements of the true affinity constant in solution of antigen-antibody complexes by enzyme-linked immunosorbent assay. J Immunol Methods. Mar. 18, 1985;77(2):305-19.

Gern et al., Immunization with a polyvalent OspA vaccine protects mice against Ixodes ricinus tick bites infected by *Borrelia burgdorferi* ss, *Borrelia garinii* and *Borrelia afzelii*. Vaccine. Oct. 1997; 15(14):1551-7.

Golde et al., Reactivity with a specific epitope of outer surface protein A predicts protection from infection with the Lyme disease spirochete, Borrelia burgdorferi. Infect Immun. Mar. 1997;65(3):882-9.

Greenspan et al., Defining epitopes: It's not as easy as it seems. Nat Biotechnol. Oct. 1999; 17(10):936-7.

Gross et al., Identification of LFA-1 as a candidate autoantigen in treatment-resistant Lyme arthritis. Science. Jul. 31, 1998;281(5377):703-6. doi: 10.1126/science.281.5377.703.

Grygorcauk et al., Assessment of the frequency of different *Borrelia burgdorferi* sensu *lato* species in patients with Lyme borreliosis from north-east Poland by studying preferential serologic response and DNA isolates. Annals of Agricultural and Environmental Medicine. 2013;20(1):21-29.

Hansen et al., Effect of the strength of adsorption of hepatitis B surface antigen to aluminum hydroxide adjuvant on the immune response. Vaccine. Feb. 5, 2009;27(6):888-92. doi: 10.1016/j.vaccine. 2008.11.078. Epub Dec. 9, 2008.

Hansen et al., Relationship between the strength of antigen adsorption to an aluminum-containing adjuvant and the immune response. Vaccine. Sep. 4, 2007;25(36):6618-24. doi: 10.1016/j.vaccine.2007. 06.049. Epub Jul. 16, 2007.

Henikoff et al., Amino acid substitution matrices from protein blocks. Proc Natl Acad Sci U S A. Nov. 15, 1992;89(22):10915-9. doi: 10.1073/pnas.89.22.10915.

Hertadi et al., Unfolding mechanics of multiple OspA substructures investigated with single molecule force spectroscopy. J Mol Biol. Nov. 7, 2003;333(5):993-1002.

Higgins et al., CLUSTAL: a package for performing multiple sequence alignment on a microcomputer. Gene. Dec. 15, 1988;73(1):237-44. doi: 10.1016/0378-1119(88)90330-7.

Higgins et al., Fast and sensitive multiple sequence alignments on a microcomputer. Comput Appl Biosci. Apr. 1989;5(2):151-3. doi: 10.1093/bioinformatics/5.2.151.

Hinckley, et al. Lyme Disease Testing by Large Commercial Laboratories in the United States. Clin Infect Dis. 2014;59(5):676-681. doi:10.1093/cid/ciu397.

Ho et al., Crystal structure of receptor-binding C-terminal repeats from Clostridium difficile toxin A. Proc Natl Acad Sci U S A. Dec. 20, 2005;102(51):18373-8. doi: 10.1073/pnas.0506391102. Epub Dec. 12, 2005.

Horn et al., Synthesis of oligonucleotides on cellulose. Part II: Design and synthetic strategy to the synthesis of 22 oligodeoxynucleotides coding for gastric inhibitory polypeptide (GIP). Nucleic Acids Symp Ser. 1980;(7):225-32.

Huang et al., Parallelization of a local similarity algorithm. Comput Appl Biosci. Apr. 1992;8(2):155-65. doi: 10.1093/bioinformatics/ 8.2.155.

Iyer et al., Stage-specific global alterations in the transcriptomes of Lyme disease spirochetes during tick feeding and following mammalian host adaptation. Molecular Microbiology. 2015;95(3):509-538. doi:10.1111/mmi.12882. Epub Dec. 30, 2014.

Jiang et al., Purification of Borrelia burgdorferi Outer Surface Protein A (OspA) and Analysis of Antibody Binding Domains Clinical and Diagnostic Laboratory Immunology. 1994;1(4):406-412.

Kiefer et al., The SWISS-MODEL Repository and associated resources. Nucleic Acids Res. Jan. 2009;37(Database issue):D387-92. doi: 10.1093/nar/gkn750.

Koide et al., Multistep denaturation of Borrelia burgdorferi OspA, a protein containing a single-layer beta-sheet. Biochemistry. Apr. 13, 1999;38(15):4757-67.

Koide et al., Structure-based design of a second-generation Lyme disease vaccine based on a C-terminal fragment of Borrelia burgdorferi OspA. J Mol Biol. Jul. 8, 2005;350(2):290-9.

Lathrop et al., Adverse event reports following vaccination for Lyme disease: Dec. 1998-Jul. 2000. Vaccine. Feb. 22, 2002;20(11-12):1603-8. doi: 10.1016/s0264-410x(01)00500-x.

Legros et al., Characterization of an anti-Borrelia burgdorferi OspA conformational epitope by limited proteolysis of monoclonal antibody-bound antigen and mass spectrometric peptide mapping. Protein Science 2000;9:1002-1010.

Li et al., Crystal structure of Lyme disease antigen outer surface protein A complexed with an Fab. Proc Natl Acad Sci U S A. Apr. 15, 1997;94(8):3584-9.

Liang et al., An immunodominant conserved region within the variable domain of VlsE, the variable surface antigen of Borrelia burgdorferi. J Immunol. Nov. 15, 1999;163(10):5566-73.

Lindgren et al., Lyme borreliosis in Europe: influences of climate and climate change, epidemiology, ecology and adaptation measures. World Health Organization. 2006. 34 pages.

Lingelbach, Developing a vaccine against Lyme disease Progress update post Phase 1 interim results. World Vaccine Congress. Apr. 4, 2018. Valneva.

Lingellbach, World Vaccine Congress presentation, Apr. 16, 2019 entitled: "Developing a vaccine against Lyme disease; Phase 1 results and next steps".

Livey et al., A new approach to a Lyme disease vaccine. Clin Infect Dis. Feb. 2011;52 Suppl 3:S266-70. doi: 10.1093/cid/ciq118.

Livey et al., Development of a novel Lyme disease vaccine. The International Conference on Lyme Borreliosis and other Tick Borne Diseases. 2010. Poster.

Lo Conte et al., The Atomic Structure of Protein-Protein Recognition Sites. J. Mol. Biol. 1999;285:2177-2198.

Makabe et al., Atomic-resolution crystal structure of Borrelia burgdorferi outer surface protein A via surface engineering. Protein Sci. Aug. 2006;15(8):1907-14. Epub Jul. 5, 2006.

Marshall et al., Safety and immunogenicity of a meningococcal B bivalent rLP2086 vaccine in healthy toddlers aged 18-36 months: a; phase 1 randomized-controlled clinical trial. Pediatr Infect Dis J. Oct. 2012;31(10):1061-8.

Mead, Epidemiology of Lyme disease. Infect Dis Clin North Am. Jun. 2015;29(2):187-210. doi: 10.1016/j.idc.2015.02.010.

Melero et al., The Pneumovirinae fusion (F) protein: A common target for vaccines and antivirals. Virus Res. Nov. 2, 2015;209:128-35. doi: 10.1016/j.virusres.2015.02.024. Epub Mar. 1, 2015.

Montgomery et al., Direct Demonstration of Antigenic Substitution of Borrelia burgdorferi Ex Vivo: Exploration of the Paradox of the Early Immune Response to Outer Surface Proteins A and C in Lyme Disease. J. Exp. Med. 1996;183:261-269.

Nadolski et al., Protein lipidation. FEBS J. Oct. 2007;274(20):5202-10. doi: 10.1111/j.1742-4658.2007.06056.x. Epub Sep. 24, 2007.

Nakagawa et al., Calorimetric dissection of thermal unfolding of OspA, a predominantly beta-sheet protein containing a single-layer beta-sheet. J Mol Biol. Nov. 1, 2002;323(4):751-62.

Nayak et al., Broadly Protective Multivalent OspA Vaccine against Lyme Borreliosis, Developed Based on Surface Shaping of the C-Terminal Fragment. Infect Immun. Mar. 23, 2020;88(4):e00917-19. doi: 10.1128/IAI.00917-19.

Needleman et al., A general method applicable to the search for similarities in the amino acid sequence of two proteins. J Mol Biol. Mar. 1970;48(3):443-53. doi: 10.1016/0022-2836(70)90057-4.

Nelson et al., Incidence of Clinician-Diagnosed Lyme Disease, United States, 2005-2010. Emerging Infectious Diseases 2015;21(9):1625-1631. DOI: http://dx.doi.org/10.3201/eid2109. 150417.

Nissen et al., A randomized, controlled, phase 1/2 trial of a Neisseria meningitidis serogroup B bivalent rLP2086 vaccine in healthy children and adolescents. Pediatr Infect Dis J. Apr. 2013;32(4):364-71. doi: 10.1097/INF.0b013e31827b0d24.

Noe et al., Mechanism of immunopotentiation by aluminum-containing adjuvants elucidated by the relationship between antigen

(56) References Cited

OTHER PUBLICATIONS retention at the inoculation site and the immune response. Vaccine. Apr. 30, 2010;28(20):3588-94. doi: 10.1016/j.vaccine.2010.02.085. Epub Mar. 5, 2010.
O'Fallon et al., A direct method for fatty acid methyl ester synthesis: application to wet meat tissues, oils, and feedstuffs. J Anim Sci. Jun. 2007;85(6):1511-21. doi: 10.2527/jas.2006-491. Epub Feb. 12, 2007.
Ornstein et al., Characterization of Lyme Borreliosis Isolates from Patients with Erythema Migrans and Neuroborreliosis in Southern Sweden. J. Clin. Microbiol 2001;39(4):1294-1298. DOI: 10.1128/JCM.39.4.1294-1298.
Ornstein et al., Differential Immune Response to the Variable Surface Loop Antigen of P66 of Borrelia burgdorferi Sensu Lato Species in Geographically Diverse Populations of Lyme Borreliosis Patients. Clin. Diagnost. Lab. Immunol. 2002;9(6):1382-1384. DOI: 10.1128/CDLI.9.6.1382-1384.2002.
Pal et al., Attachment of Borrelia burgdorferi within Ixodes scapularis mediated by outer surface protein A. J. Clin. Invest. 2000;106:561-569.
Pantoliano et al., High-density miniaturized thermal shift assays as a general strategy for drug discovery. J Biomol Screen. Dec. 2001;6(6):429-40.
Parmley, Uptick for Lyme vaccine. Biocentury innovations. Jan. 15-16, 2015.
Pawley et al., Backbone dynamics and thermodynamics of Borrelia outer surface protein A. J Mol Biol. Dec. 13, 2002;324(5):991-1002.
Pearson et al., Improved tools for biological sequence comparison. Proc Natl Acad Sci U S A. Apr. 1988;85(8):2444-8. doi: 10.1073/pnas.85.8.2444.
Pearson, Using the FASTA program to search protein and DNA sequence databases. Methods Mol Biol. 1994;25:365-89. doi: 10.1385/0-89603-276-0:365.
Pham et al., NMR studies of Borrelia burgdorferi OspA, a 28 kDa protein containing a single-layer beta-sheet. J Biomol NMR. May 1998;11(4):407-14.
Piesman et al., Lyme borreliosis in Europe and North America. Parasitology 2004;129, S191-S220. doi: 10.1017/S0031182003004694.
Poland, Vaccines against Lyme Disease: What Happened and What Lessons Can We Learn? Clinical Infectious Diseases 2011;52(S3):S253-S258. doi: 10.1093/cid/ciq116.
Pritt et al., Identification of a novel pathogenic Borrelia species causing Lyme borreliosis with unusually high spirochaetaemia: a descriptive study. Lancet Infect Dis. May 2016;16(5):556-564. doi: 10.1016/S1473-3099(15)00464-8. Epub Feb. 6, 2016. Erratum in: Lancet Infect Dis. Jun. 2016;16(6):636.
Pronk et al., GROMACS 4.5: a high-throughput and highly parallel open source molecular simulation toolkit. Bioinformatics. Apr. 1, 2013;29(7):845-54. doi: 10.1093/bioinformatics/btt055.
Radolf et al., Of ticks, mice and men: understanding the dual-host lifestyle of Lyme disease spirochaetes. Nat Rev Microbiol. 2012;10(2): 87-99. doi: 10.1038/nrmicro2714.
Richmond et al., A bivalent Neisseria meningitidis recombinant lipidated factor H binding protein vaccine in young adults: results of a randomised, controlled, dose-escalation phase 1 trial. Vaccine. Sep. 21, 2012;30(43):6163-74. doi: 10.1016/j.vaccine.2012.07.065. Epub Aug. 5, 2012.
Richmond et al., Safety, immunogenicity, and tolerability of meningococcal serogroup B bivalent recombinant lipoprotein 2086 vaccine in healthy adolescents: a randomised, single-blind, placebo-controlled, phase 2 trial. Lancet Infect Dis. Aug. 2012;12(8):597-607. Epub May 7, 2012.
Rizzoli et al., Lyme borreliosis in Europe. Euro Surveill. 2011;16(27):pii=19906. Available online: http://www.eurosurveillance.org/ViewArticle.aspx?ArticleId=19906.
Roberge et al., A strategy for a convergent synthesis of N-linked glycopeptides on a solid support. Science. Jul. 14, 1995;269(5221):202-4.
Routledge, Beyond de-foaming: the effects of antifoams on bioprocess productivity. Comp and Struct Biotechnol J. Oct. 2012;3(4):e201210014. doi: 10.5936/csbj.201210014. 7 pages.
Scarselli et al., Rational Design of a Meningococcal Antigen Inducing Broad Protective Immunity. www.ScienceTranslationalMedicine.org. 2011;3(91):91ra62.
Schaible et al., Monoclonal antibodies specific for the outer surface protein A (OspA) of Borrelia burgdorferi prevent Lyme borreliosis in severe combined immunodeficiency (scid) mice. Proc. Nati. Acad. Sci. USA 1990;87:3768-3772.
Schildgen et al., Human Metapneumovirus: lessons learned over the first decade. Clin Microbiol Rev. Oct. 2011;24(4):734-54. doi: 10.1128/CMR.00015-11.
Schlegl et al., Influence of elemental impurities in aluminum hydroxide adjuvant on the stability of inactivated Japanese Encephalitis vaccine, IXIARO®. Vaccine. Nov. 4, 2015;33(44):5989-96. doi: 10.1016/j.vaccine.2015.05.103. Epub Jun. 19, 2015.
Schubach et al., Mapping Antibody-Binding Domains of the Major Outer Surface Membrane Protein (OspA) of Borrelia burgdorferi. Infect. And Immun. 1991;59(6):1911-1915.
Schuijt et al., Lyme borreliosis vaccination: the facts, the challenge, the future. Trends in Parasitology 2011;27(1):40-47. doi:10.1016/j.pt.2010.06.006.
Schwan et al., Temporal Changes in Outer Surface Proteins A and C of the Lyme Disease-Associated Spirochete, Borrelia burgdorferi, during the Chain of Infection in Ticks and Mice. J Clin Microbiol. Jan. 2000; 38(1):382-8.
Schwendinger et al., Evaluation of OspA vaccination-induced serological correlates of protection against Lyme borreliosis in a mouse model. PLoS One. Nov. 18, 2013;8(11):e79022. doi: 10.1371/journal.pone.0079022.
Sears et al., Molecular Mapping of Osp-A Mediated Immunity Against Borrelia burgdorferi, The Agent of Lyme Disease. J of Immunol 1991;147(6):1995-2000.
Sigal et al., A vaccine consisting of recombinant Borrelia burgdorferi outer surface protein A to prevent lyme disease. N Engl J Med 1998;339:216-22.
Smith et al., Comparison of Biosequences. Adv Appl Math. 1981;2:482-9.
Stanek et al., Lyme borreliosis. Lancet. 2012;379:461-73 doi:10.1016/S0140-6736(11)60103-7. EPub Sep. 7, 2011.
Steere et al., Vaccination against Lyme disease with recombinant Borrelia burgdorferi outer-surface lipoprotein A with adjuvant. Lyme Disease Vaccine Study Group. N Engl J Med. Jul. 23, 1998;339(4):209-15.
Stupica et al., Correlation of Culture Positivity, PCR Positivity, and Burden of Borrelia burgdorferi Sensu Lato in Skin Samples of Erythema Migrans Patients with Clinical Findings. PLoS One 2015;10(9): e0136600. doi:10.1371/journal.pone.0136600.
Todar, Todar's Online Textbook of Bacteriology; Nutrition and Growth of Bacteria. Accessible at texbookofbacteriology.net/nutgro.html. Retrieved on Mar. 11, 2021. 2 pages.
Ulbrandt et al., Conformational Nature of the Borrelia burgdorferi Decorin Binding Protein A Epitopes That Elicit Protective Antibodies. Infection and Immunity 2001;69(8)4799-4807. doi: 10.1128/IAI.69.8.4799-4807.2001.
Van Den Hoogen et al., Analysis of the genomic sequence of a human metapneumovirus. Virology. Mar. 30, 2002;295(1):119-32. doi: 10.1006/viro.2001.1355.
Van Den Hoogen et al., Antigenic and genetic variability of human metapneumoviruses. Emerg Infect Dis. Apr. 2004;10(4):658-66. doi: 10.3201/eid1004.030393.
Van Hoecke et al., Evaluation of the safety, reactogenicity and immunogenicity of three recombinant outer surface protein (OspA) lyme vaccines in healthy adults. Vaccine. Dec. 1996;14(17-18):1620-6.
Von Eichel-Streiber et al., Clostridium difficile toxin A carries a C-terminal repetitive structure homologous to the carbohydrate binding region of streptococcal glycosyltransferases. Gene. Nov. 30, 1990;96(1):107-13. doi: 10.1016/0378-1119(90)90348-u.
Voth et al., Clostridium difficile toxins: mechanism of action and role in disease. Clin Microbiol Rev. Apr. 2005;18(2):247-63. doi: 10.1128/CMR.18.2.247-263.2005.
Wilske et al., An OspA serotyping system for Borrelia burgdorferi based on reactivity with monoclonal antibodies and OspA sequence analysis. J Clin Microbiol. Feb. 1993;31(2):340-50.

(56) References Cited

OTHER PUBLICATIONS

Wormser et al., The clinical assessment, treatment, and prevention of lyme disease, human granulocytic anaplasmosis, and babesiosis: clinical practice guidelines by the Infectious Diseases Society of America. Clin Infect Dis. Nov. 1, 2006;43(9):1089-134. doi: 10.1086/508667. Epub Oct. 2, 2006. Erratum in: Clin Infect Dis. Oct. 1, 2007;45(7):941.

Wressnigg et al., A Novel multivalent OspA vaccine against Lyme borreliosis is safe and immunogenic in an adult population previously infected with Borrelia burgdorferi sensu lato. Clin Vaccine Immunol. Nov. 2014;21(11):1490-9. doi: 10.1128/CVI.00406-14. Epub Sep. 3, 2014.

Wressnigg et al., Safety and immunogenicity of a novel multivalent OspA vaccine against Lyme borreliosis in healthy adults: a double-blind, randomised, dose-escalation phase 1/2 trial. Lancet Infect Dis. Aug. 2013;13(8):680-9. doi: 10.1016/S1473-3099(13)70110-5. Epub May 10, 2013.

Yoder et al., Tripalmitoyl-S-glyceryl-cysteine-dependent OspA vaccination of toll-like receptor 2-deficient mice results in effective protection from Borrelia burgdorferi challenge. Infect Immun. Jul. 2003;71(7):3894-900.

Zhong et al., Plasmid DNA and protein vaccination of mice to the outer surface protein A of Borrelia burgdorferi leads to induction of T helper cells with specificity for a major epitope and augmentation of protective IgG antibodies in vivo. Eur. J. Immunol. 1996;26:2749-2757.

Chothia et al., The relation between the divergence of sequence and structure in proteins. EMBO J. Apr. 1986;5(4):823-6. doi: 10.1002/j.1460-2075.1986.tb04288.x.

\* cited by examiner

Figure 1A
LAYOUT 1
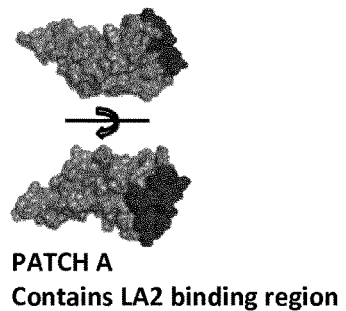
PATCH A
Contains LA2 binding region
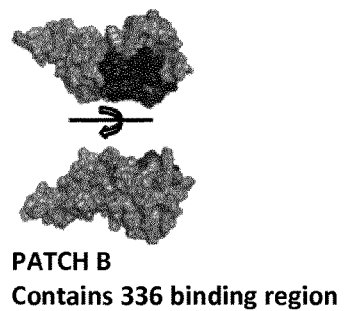
PATCH B
Contains 336 binding region
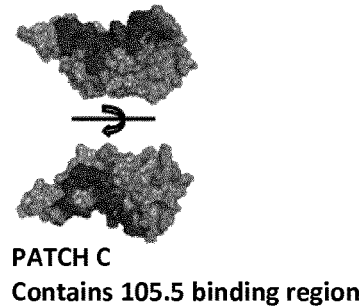
PATCH C
Contains 105.5 binding region
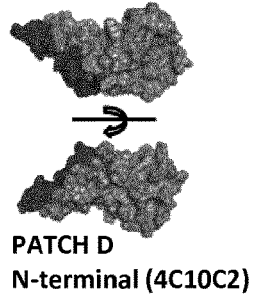
PATCH D
N-terminal (4C10C2)
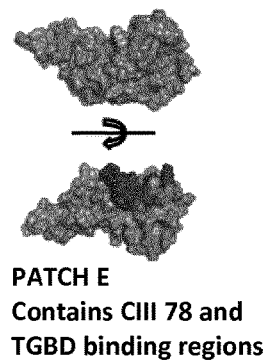
PATCH E
Contains CIII 78 and
TGBD binding regions
LAYOUT 2
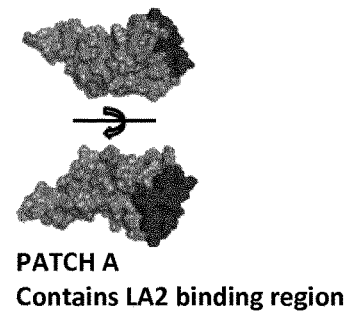
PATCH A
Contains LA2 binding region
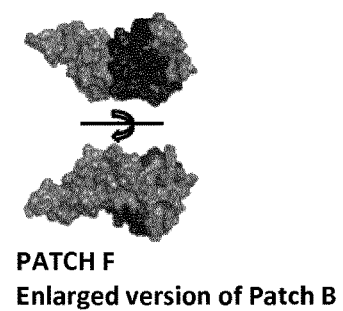
PATCH F
Enlarged version of Patch B
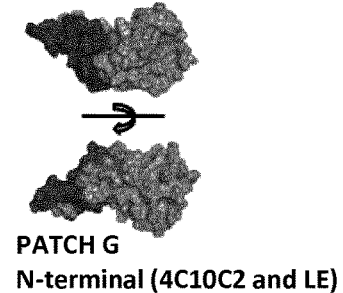
PATCH G
N-terminal (4C10C2 and LE)
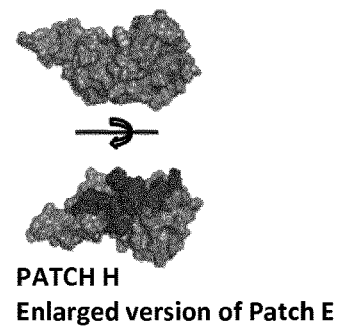
PATCH H
Enlarged version of Patch E

Figure 1B

| Proteins | Disulfide bond | Patch A | Patch F | Patch G | Patch H | |
|---|---|---|---|---|---|---|
| Variant 1 | α | ST1 | ST5 | ST5 | ST4 | |
| Variant 2 | ß | ST1 | ST5 | ST5 | ST4 | |
| Variant 3 | ß | ST1 | ST5 | ST4 | ST5 | |
| Variant 4 | α | ST1 | ST5 | ST4 | ST5 | |
| | | Patch A | Patch B | Patch C | Patch D | Patch E |
| Variant 5 | ß | ST6 | ST3 | ST2 | ST2 | ST6 |
| Variant 6 | ß | ST2 | ST3 | ST2 | ST2 | ST6 |

Figure 2

```
B. afzelii K78 (ST2) 126 FNEKGELSAKTMTRENGTKLEYTEMKSDGTGKAKEVLKNFTLEGKVAND-KVTLEVKEGTVTTLSKEIAKSGEVTVALNDT 204
Variant 1              1 ....I.E..IV.A..R....DI...K.........D......T.A.-.....KT.........H.PN....I..E.D...  79
Variant 2              1 ....I.E..IV.A..R....DI...K.........D......T.A.-.....K.TC........H.PN....I..E.D...  79
Variant 3              1 .....A...E..IL.A..R......I................D.A...T..A.G......K.TC.........N.S......I......D...  80
Variant 4              1 .....A...E..IL.A..R......I................D.A...T..A.G......K.T..........N.S......I......D...  80
Variant 5              1 .................................................-................C.............................  79
Variant 6              1 .................................................-................C.............................  79
Exposure                 o+++++++++o+-oo+++-+-++-++++++++-+-+++-+++-+-+++-+++++-+-+o++++-+-+++++-+-+-+
Layout 1                 DDDDDDDDDDDDDDDD-D-CC-CCCCCCC-D-D-DD-C-CCC-CCCCC-C-C-CCCCC-C-C-CCCCCC-C-C-C
Layout 2                 GGGGGGGGGGGGGGGG-G-GGGGGGGGGG-G-GGGGGGGGG-G-GGG-GGHHH-H-F-FFFFFF-H-H-HHHHHHH-H-FFF
Type "alpha"             ----------------------------------------------------------------------------
Type "beta"              -------------------------------C-------------------------------------------
PDB 1OSP (ST1)       126 FNEKGEVSEKIITRADGTRLEYTGIKSDGSGKAKEVLKGYVLEGTLTAE-KTTLVVKEGTVTLSKNISKSGEVSVELNDT 204

B. afzelii K78 (ST2) 205 NTTQATKKKTGAWDSKTSTLTISVNSKKTTQLVFTKQDTITVQKYDSAGTNLEGTAVEIKTLDELKNALK 273
Variant 1             80 DSSA.......A.....N........T........KN.........E....C..N.....N.........KC....T.K.... 148
Variant 2             80 DSSA.......A.....N........T........KN.........E.......N.....N.........K......T.K..C... 148
Variant 3             81 DSSA.......A......G.......T........K..........E.......N.....N.........K......T.K..C... 149
Variant 4             81 DSSA.......A......G.......T........K..........E....C..N.....N.........KC....T.K.... 149
Variant 5             80 ....R......K.................Q..KN.........E..........N..............SPA..D.A..CA... 148
Variant 6             80 ...........................KN.........E..........N..............SPA..D.A..CA... 148
Exposure                 ++++++++++-+-+++++--o-oo++++o--+-+++++o-o-o+-o++-+-++++++-+++++-++--+
Layout 1                 CAAAACACAAAAEEEEEEE-E-AAAAAABBE-E-AAAAAABBE-E-EEE-E-EBEB-AAAAAE-BBBBB-AAAAAE-BBBBB-BBB-B
Layout 2                 AAAAAAAAAAHHHHHHH-H-AAAAAAFFH-H-AAAAAAFFH-H-HHH-H-HFHFHAAAAAHHFFFFF-FFFFF-FFF-F
Type "alpha"             ------------------------------C-----------------------------------
Type "beta"              -----------------------------------------C-----------------------
PDB 1OSP (ST1)       205 DSSAATKKTAAWNSGTSTLTITVNSKKTKDLVFTKENTITVQQYDSNGTKLEGSAVEITKLDEIKNALK 273
```

Figure 3

A

```
Lip—CSS                                                                                    HHHHHH
         ┌─┬─┬─┬─┬─┬─┬─┐        S              S       ┌──┬─┬──┬─┬──┬─┬──┬─┬──┬─┬─┐   S
         │G│H│F│H│H│F│A│          ┌──┐            ┌─┬─┐│A │E│A │B│E │A│E │A│A │E│B│
         └─┴─┴─┴─┴─┴─┴─┘          │L2│            │D │C││  │ │  │ │  │ │  │ │  │ │ │
                H   A              └──┘            │  │D││  │ │  │ │  │ │  │ │  │ │ │
               F F  H H                                 C   ↑ B ↑ B  ↑ B ↑ B ↑ B E
                    ←   ←                                   A   A   A   A   A
         ←─────────────→                          ←─────────────────────────────→
              Variant 3                                       Variant 5
```

B

```
B.afzelii ST2 (PKo)
Type "beta"           126 FNEKGELSAKTMTRENGTKLEYTEMKSDGTGKAKEVLKNFTLEGKVAND-KVTLEVKEGTVTLSKEIAKSGEVTVALNDT 204
Variant3                1 .A....E..IL.A..R...I............D.A...T..A.G...K.TC....N.S...I...D.. 80
Layout 2                  GGGGGGGGGGGGGGGGG-G-GGGGGGGGGG-G-G-GG-G-GGG-GGHHH-H-F-FFFFFF-H-H-HHHHHHH-H-FFF
Variant5                1 ..................N............-.....C....C...............-..... 79
Layout 1                  DDDDDDDDDDDDDDDDDD-D-CC........D-D-CCC-C-CCC-CCCCC-C-C-C-CCCC-C-C-CCCCCC-C-C-C B.afzelii ST2 (PKo)
Type "beta"           205 NTTQATKKTGAWDSKTSTLTISVNSKKTTQLVFTQKDTITVQKYDSAGTNLEGTAVEIKTLDELKNALK 273
Variant3               81 DSSA....A....G.....T.....K.....E.....N...N.....K...T.K.C.....C---- 149
Layout 2                  AAAAAAAAAAAAHHHHHHH-H-AAAAAAFFH-H-HHH-H-HFHFHAAAAAAHHFFFFFF-FFFFF-FFF-F
Variant5               80 ...R.....K.......Q..KN.....E........N.......SPA...D.A..CA... 148
Layout 1                  CAAAACACAAAEEEEEEE-E-AAAAAABBE-E-EEE-E-EBEB-AAAAAE-EBEB-AAAAE-BBBBBB-BBBBB-BBB-B L2 (P66 B. garinii PBr)   1 ANNQAGQKSSGSTQATTPNLTFE 23
```

MULTIVALENT OspA POLYPEPTIDES AND METHODS AND USES RELATING THERETO

RELATED APPLICATION

This application is a national stage filing under 35 U.S.C. § 371 of International Patent Application PCT/EP2018/059533, filed Apr. 13, 2018, the content of which is incorporated herein by reference in its entirety.

FIELD OF THE INVENTION

The invention relates to constructs and compositions for use as prophylactic or therapeutic treatments against *Borrelia* infections.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 11, 2019, is named I042270130US00-SEQ-CEW and is 114 kilobytes in size.

BACKGROUND OF THE INVENTION

The present invention relates to an immunogenic polypeptide, a nucleic acid encoding the same, a pharmaceutical composition comprising the same and the immunogenic polypeptide, nucleic acid or pharmaceutical composition for use as a medicament, particularly a vaccine, or for use in a method of treating or preventing a *Borrelia* infection.

Lyme borreliosis (LB), or Lyme disease, is the most commonly reported tick-borne disease in Europe and North America. The disease is caused by the arthropod-borne gram-negative-like spirochete, *Borrelia burgdorferi sensu lato* (*B. burgdorferi* s.l.). *Borrelia* belongs to the family *Spirochaetaceae*, which is subdivided into the medically important genera *Treponema, Leptospira* and *Borrelia*. *B. burgdorferi* s.l. is a spiral-shaped, vigorously motile gram-negative-like bacterium, about 10-20 μm long and 0.2-0.5 μm wide, that grows under microaerophilic conditions. The spirochetal cell wall consists of a cytoplasmic membrane immediately surrounded by peptidoglycan and several flagella and further by a loosely-associated outer membrane. The spirochetes are transmitted by hard bodied *Ixodes* spp. ticks in a complex enzootic cycle which primarily includes small mammals and birds. Transmission occurs during the tick feeding, when the infected tick transmits the spirochetes into the host blood stream. When humans contract the infection, a spectrum of distinct clinical manifestations can follow, ranging from early localized infection of the skin (erythema migrans) to progressive disseminated infection of the nervous system (neuroborreliosis), skin (acrodermatitis chronica atrophicans), heart (Lyme carditis) and joints (Lyme arthritis). *B. burgdorferi* s.l. consists of at least 17 genospecies worldwide. The genospecies *B. garinii* can be further divided into several serotypes based on binding of monoclonal antibodies to the outer surface protein A (OspA).

In most countries, Lyme borreliosis is not a notifiable disease and no exact data regarding annual incident rates are available. In Europe, four *B. burgdorferi* s.l. genospecies, representing six different OspA serotypes (ST), are responsible for the majority of human clinical cases; *B. burgdorferi sensu stricto* (s.s.; OspA ST1), *B. afzelii* (OspA ST2) *B. garinii* (OspA ST3, ST5 and ST6) and *B. bavariensis* (OspA ST4).

The number of LB cases in Europe is estimated to be at least 200,000 annually, but due to the lack of centralized surveillance and data acquisition systems, coupled with the fact that LB is not a reportable disease in most European countries, this number is most likely still an underestimation. In the US, the Centers for Disease Control (CDC) estimate the annual LB cases at between 288,000 and 329,000, thereby establishing LB as a major health burden with substantial economic impact. The increasing incidence of cases globally argues in favor of development of a multivalent vaccine that would reduce the debilitating health and economic burden of the disease globally.

Efforts to develop a subunit vaccine for prevention of Lyme borreliosis have been focused in large part on the use of borrelial outer surface protein A (OspA) as an antigen. Vaccines based on OspA have been comprehensively studied in pre-clinical and clinical settings. At least two monovalent vaccines (LYMErix™, SmithKline Beecham and ImuLyme, Pasteur Merieux-Connaught) based on the full-length OspA of *B. burgdorferi* s.s. (OspA ST1) have been assessed in clinical trials, the former vaccine having been licensed for human use from 1998 to 2002. Additionally, a recombinant vaccine comprising three chimeric OspA antigens covering six OspA serotypes was also tested in clinical trials (Wressnig N. et al., 2013, Lancet Infect. Dis. 13(8):680-689 and Wressnigg N. et al., 2014, Clin. Vaccine Immunol. 21(11):1490-1499).

A hexavalent LB vaccine candidate developed by Valneva Austria GmbH is based on the C-terminal half of six different OspA serotypes (OspA ST1-ST6) linked together to form three heterodimeric fusion proteins, each heterodimer containing OspA fragments from two different *Borrelia* serotypes (Comstedt et al., 2014, PLoS One 9(11):e113294; Comstedt et al., 2015, Vaccine 33(44):5982-8; WO14/006226 and WO15/104396). This LB vaccine represents an advance in the field as the number of proteins in the vaccine formulation has been reduced to three instead of six; nonetheless, considerable costs and complexity are still involved in the production process.

Accordingly, in one embodiment, it was an object of the present invention to provide an improved vaccine against Lyme borreliosis, particularly a multivalent, broadly protective polypeptide to be used as a vaccine against Lyme borreliosis, preferably with a limited number of required antigens. Preferably, the vaccine is easily produced while being protective, safe and more effective than existing therapies and/or provides protection against more than one *Borrelia* species or OspA serotype. More preferably, it was intended to provide a single antigen in the final vaccine formulation without compromising protection against the majority of clinically-relevant *Borrelia* species and OspA serotypes associated with LB in humans.

SUMMARY OF THE INVENTION

The object was solved by providing chimeric polypeptides based on a scaffold OspA fragment which is altered to contain immunogenic portions of OspA which are derived from different serotypes (abbreviated herein as "ST"). In light of the complexity, the inventors have, for the development of a Lyme borreliosis vaccine, applied a structure-based surface shaping approach, targeting the six most clinically relevant OspA serotypes (ST1-ST6) of the *Borrelia* species causing Lyme borreliosis. "Surface shaping" as used herein means the rational alteration of amino acids present on the surface of an OspA C-terminal fragment. This alteration of certain surface amino acid residues is used herein to design chimeric OspA fragments containing immunogenic patches (i.e., epitopes or portions of epitopes) on the three dimensional surface structure which correspond to distinct serotypes of OspA; i.e., to produce a multivalent OspA antigen, e.g. in sum representing regions of two, three or more serotypes on its surface. The C-terminal half of OspA, which is the part of OspA which is exposed on the surface of the *Borrelia* spirochete, has been used for surface shaping. The sequence of OspA from *B. afzelii* (OspA ST2) which represents the most prevalent ST causing LB in Europe has been used as the "conserved backbone" or "structural scaffold" for the chimeric proteins disclosed herein. The surface of the OspA fragment has been divided into regions referred to herein as "patches" and amino acids of the individual regions have been exchanged (see Example 1). As used herein, the multivalent OspA antigen, by virtue of containing epitopes from two or more OspA serotypes may also be referred to as "chimeras" or "multivalent chimeras" or "multivalent antigens".

In the course of the invention, the concept of surface shaping was approached by examining the three-dimensional crystal structure of ST1 OspA (Li et al., 1997, PNAS 94(8):3584-9). The procedure of surface shaping is described herein for the C-terminal domain of OspA, but could also be applied e.g. for the design of full-length multivalent OspA. First, amino acid residues in the C-terminal region of ST2 OspA were characterized based on their apparent accessibility in the protein structure (based on the ST1 crystal structure) in relation to the surface; i.e., exposed ("+"), partially exposed ("0") or buried ("−") (see FIG. 2). For the classification 'buried', the structure also was checked with respect to sidechain packing in the core. Residues which participated in the compact hydrophobic sidechain packing 'core' structure of ST2 were retained. Next, each residue was further evaluated using a scaling factor for per-residue interference penalties in the combination selection step, taking into account interference between neighboring patch attributions. Scaling factors were 0, 0.5 and 1 for buried, partially exposed and exposed, but distinguishing between partially exposed and exposed, with effect on the ranking of the possible combinations. For partially exposed residues the decision to include them as 'exposed' was not unambiguous but was taken conservatively, i.e. the ranking of the residue may have been adapted based on additional information. For example, in some cases, a particular partially exposed residue could be considered either 'exposed' or 'buried' depending upon the angle of observation.

In a further step, the OspA fragment was examined in terms of "patches", i.e., areas on the surface of the folded molecule which comprise potential/known epitopes (i.e., antibody binding sites such as e.g. LA-2 for serotype 1 for which a crystal structure is available, PDB 1FJ1) or epitopes known in the field provided from a diversity of methods in varying detail, among them NMR chemical shift perturbation, point mutation experiments, antibody competition, linear peptide scanning and/or epitope prediction. A patch as used herein means an area on the surface of the OspA molecule which comprises a potentially immunogenic region, i.e., an epitope or a partial epitope, preferably a region containing a partial or complete antibody footprint, i.e., antibody binding site. The patch may be about 400-2000 angstroms square ($Å^2$), preferably about 500-1800 $Å^2$, more preferably between about 600-1600 $Å^2$, even more preferably about 800-1200 $Å^2$.

As used herein, a specific OspA epitope shall mean the binding area of a specific antibody to OspA and, in particular, is defined herein as the binding area on OspA of any antibody that is competed away by at least 50% by a specific antibody known to be specific for said binding area. In general, an epitope is approximately five or six amino acids in length. In this regard, a typical full-length protein sequence contains many different epitopes against which distinct antibodies can bind. For any given protein sequence, multiple unique antibodies will generally recognize the protein. Each of these antibodies binds to a specific epitope located on that protein. Within a protein sequence, one can find both 1) continuous epitopes, which are formed by or defined by linear sequences of amino acids within the protein, and 2) discontinuous epitopes, which exist only when the protein is folded into a particular conformation and more distal regions of the primary sequence are arranged in proximity to one another. Preferable OspA epitopes include those associated with protection and/or those corresponding to the mapped binding sites of monoclonal antibodies described in the literature as well as additional binding regions reported for the C-terminal fragment of OspA ST1 (Sears J E, et al. 1991. Molecular mapping of Osp-A mediated immunity against *Borrelia burgdorferi*, the agent of Lyme disease. J. Immunol. 147:1995-2000; Wilske B, et al. 1992. Molecular analysis of the outer surface protein A (OspA) of *Borrelia burgdorferi* for conserved and variable antibody binding domains. Med. Microbiol. Immunol. 181: 191-207; Jiang W, et al. 1994. Purification of *Borrelia burgdorferi* outer surface protein A (OspA) and analysis of antibody binding domains. Clin. Diagn. Lab. Immunol. 1:406-12).

Findings from the ST1 OspA C-terminal three-dimensional structure from PDB 1OSP (a complex with Fab 184.1, which binds to the C-terminus and shows the C-terminus unaffected by conformational changes from antibody binding), e.g., ranking, spatial position and attribution to defined surface areas of the amino acid residues, were then applied to the homologous fragment from ST2 OspA (see FIG. 2). This fragment, used as a backbone for designing the multivalent OspA antigen, was in silico altered in a variety of ways. The backbone further comprised the addition of at least two cysteine residues for the introduction of a disulphide bond for stabilizing the three dimensional structure of the OspA fragment.

Within a patch, the residues which are exposed are replaced to represent a surface of the target serotype/genotype, while buried residues with their sidechain not accessible are retained. Buried residues often represent hydrophobic amino acids and often are tightly packed. In this quality they contribute to define the fold of the protein, which in the case of OspA ST1-6 is highly homologous. Not changing the non-accessible residues avoids situations in which the buried core residues of adjacent patches representing characteristics of diverging serotypes/genotypes would be exchanged in a non-fitting manner leading to fold distortions.

The attribution of adjacent patches can be optimized, by taking into account that, depending on the choice of the serotype attributions to the patches, situations can arise in which the relative spatial orientation of conflicting residues in adjacent patches is altered. The term "conflicting" as used in this respect means that on the surface a residue is close to an adjacent patch which is different from the actual serotype/ genotype attribution. A programmatic approach was used to attribute higher penalty scores to combinations which have more conflicting residues. This can be achieved by systematically finding for all patches the conflicting residues and applying a scoring scheme which takes into account the exposition rank and the distance between conflicting residues as defined by the C-alpha atoms to define a cutoff for the calculation. Scoring is repeated for all combinations of desired serotypes/genotypes to be represented on die multivalent polypeptide.

A variety of multivalent ST2 fragment designs were examined in silico. For proof-of-principle, two patch layouts (Layouts 1 and 2, FIGS. 1A and B, respectively) were selected and the polypeptides Variants 1-4 (layout 1) and Variants 5-6 (layout 2) were synthesized and tested (see FIG. 2). The Variants as described in the examples represent only finite examples of the many possibilities with regard to OspA surface patch definition and should not be regarded as limiting. These six chimeric proteins possess combinations of surface-exposed amino acids representing multiple OspA serotypes. All six of the Variants were assessed for immunogenicity by measuring specific antibody response by ELISA and for functional OspA binding antibodies by *Borrelia* surface binding and a growth inhibition assay (see Examples 2 to 4).

Briefly, only the four multivalent OspA monomeric fragments with a β-type disulfide bond (disulfide bond between two introduced cysteine residues at the amino acid positions corresponding to amino acids 182 and 269 of OspA serotype 2) proved to be significantly protective in mouse challenge models. Surprisingly, the presence of an α-type disulfide bond (disulfide bond between two introduced cysteine residues at the amino acid positions corresponding to amino acids 244 and 259 of OspA serotype 2) did not seem to be favorable for the three-dimensional presentation of the immunogenic epitopes contained in the primary sequence.

The four multivalent chimeras having a β-type disulfide bond (Variants 2, 3, 5 and 6) conferred significant protection in mice challenged with ticks infected with *B. burgdorferi* s.s. (OspA ST1), *B. afzelii* (OspA ST2) and *B. bavariensis* (OspA ST4), as well as needle challenges with in vitro grown *B. burgdorferi* s.s. (OspA ST1) and two *B. garinii* strains (OspA ST5 and ST6) (Table 2). The study demonstrates a novel multivalent OspA vaccine approach that has the potential to achieve broad protection with a single antigen, also making the process of OspA vaccine development less intricate and more cost-effective.

Accordingly, in one aspect, the present invention relates to an altered OspA C-terminal OspA fragment or domain which provides distinct epitopes from at least two, at least three, at least four distinct species and/or strains of *Borrelia*; i.e., a multivalent OspA antigen. This approach provides a modality for addressing a plurality of clinically-relevant OspA serotypes in the context of one immunogenic polypeptide. Furthermore, such multivalent OspA antigens may be combined into heteromers, such as e.g. heterodimers or heterotrimers, to provide multiple epitopes simultaneously and potentially protection from multiple strains and/or serotypes and/or species of pathogenic *Borrelia*. In a preferred embodiment, said heteromers provide epitopes from at least four, at least five, at least six, at least seven, at least eight distinct *Borrelia* species and/or strains, preferably at least six, most preferably exactly six. In one embodiment, the heteromers are joined by linker peptides. In a preferred embodiment, the heteromers are N-terminally lipidated. As used herein, "epitope" shall mean an immunogenic region which corresponds to at least a partial binding site of at least one antibody, preferably more than one antibody. The alteration from its native form of an OspA C-terminal fragment, which may also referred to herein as a "scaffold", may be accomplished by the combination of serial sub-fragments of the OspA fragment from different species or strains of *Borrelia*, e.g., the fusion of adjacent amino acid sequences derived from different *Borrelia* strains. This approach is described in detail in WO2015/104396, which is incorporated herein by reference in its entirety. Additionally, in a preferred embodiment, a scaffold C-terminal fragment of OspA derived from one species or strain of *Borrelia* may be rationally altered in its structure by introducing point mutations in key locations in order to recreate known epitopes from one or more additional distinct *Borrelia* species or strain or serotype. In one aspect, the OspA C-terminal fragment is stabilized by the introduction of at least one non-native disulfide bond. In a preferred embodiment, the OspA C-terminal fragment is stabilized by the introduction of exactly one non-native disulfide bond.

As used herein, a C-terminal OspA fragment shall mean a C-terminal portion of the entire OspA protein that comprises or consists of approximately 50-60% of the C-terminal amino acids, preferably about 55% of the C-terminal amino acids. Most preferably, the C-terminal OspA fragment shall comprise or consist of amino acids corresponding to amino acids 126-273, using the OspA of *B. afzelii* (SEQ ID NO: 74) as a reference sequence. As used herein, a C-terminal OspA fragment which folds into a stable three dimensional structure, whether spontaneously or due to introduction of stabilizing mutations; e.g., cysteine bonds, is also referred to as a C-terminal OspA domain. In particular, a C-terminal OspA domain as used herein shall mean the complete extracellular part of OspA, such as, for example, the fragment consisting of amino acids 126-273 of *B. afzelii* OspA (SEQ ID NO: 7) or a functional equivalent thereof that has at least 50%, 60%, 70%, 80%, 90%, 95%, 96%, 97%, 98%, 99% sequence identity using a global alignment method such as the Needleman-Wunsch algorithm (Needleman and Wunsch (1970) A general method applicable to the search for similarities in the amino acid sequence of two proteins. J of Mol Biol. 48 (3): 443-53). The C-terminal OspA domain is preferably stabilized by the introduction of two cysteine residues, preferably at positions between about amino acids 180 to 184 and 267 to 271, most preferably at amino acids 182 and 269. As used herein, "functional equivalent" shall mean at least maintaining specific immunogenicity.

Accordingly, in one aspect, the present invention relates to the definition of patches and layouts of an OspA fragment based on the three-dimensional structure as described above. It further relates to the design of immunogenic multivalent OspA antigens, preferably based on desired serotype configurations in combination with the before-mentioned definition of patches and layouts. In one embodiment, the multivalent OspA antigen of the invention comprises regions or parts of OspA proteins from at least two, at least three, at least four or more different species or distinct strains of *Borrelia*.

Accordingly, in one aspect the present invention relates to the above OspA chimeras (multivalent antigens) and variants thereof. Particularly, the present invention relates to an immunogenic polypeptide comprising
(i) a peptide with an amino acid sequence selected from the group consisting of SEQ ID NO: 9 and SEQ ID NO: 10, or an immunogenic variant thereof, wherein said immunogenic variant has at least 90% sequence identity with SEQ ID NO: 9 or SEQ ID NO: 10; and/or (ii) a peptide with an amino acid sequence selected from the group consisting of SEQ ID NO: 12 and SEQ ID NO: 13, or an immunogenic variant thereof, wherein said immunogenic variant has at least 90% sequence identity with SEQ ID NO: 12 or SEQ ID NO: 13.

As a next step, the chimeric proteins from one of the combinations were linked to form a fusion protein with the aim to have only one protein in the final formulation, thereby achieving broad protection with a single antigen. The fusion vaccine provides significant protection against challenges with in vitro grown *B. burgdorferi* s.s. (OspA ST1) and ticks infected with *B. afzelii* (OspA ST2) demonstrating high efficacy (see Examples 5 and 6).

Accordingly, in one aspect, the present invention relates to these fusion proteins, namely an immunogenic polypeptide comprising
  (i) a peptide with an amino acid sequence selected from the group consisting of SEQ ID NO: 9 and SEQ ID NO: 10, or an immunogenic variant thereof, wherein said immunogenic variant has at least 90% sequence identity with SEQ ID NO: 9 or SEQ ID NO: 10; and
  (ii) a peptide with an amino acid sequence selected from the group consisting of SEQ ID NO: 12 and SEQ ID NO: 13, or an immunogenic variant thereof, wherein said immunogenic variant has at least 90% sequence identity with SEQ ID NO: 12 or SEQ ID NO: 13.

Details on the above-mentioned aspects of the present invention are given in the following:

*Borrelia* is a genus of bacteria of the spirochete phylum. *Borrelia* causes the vector-borne diseases relapsing fever and Lyme disease, depending on the species. *Borrelia* is transmitted primarily by ticks, but some species are transmitted by lice. At present there are 36 known species of *Borrelia*. Of the 36 known species of *Borrelia*, at least 13 of these species are known to cause Lyme disease (LD) or borreliosis and are transmitted by ticks. The major *Borrelia* species causing Lyme disease are *Borrelia burgdorferi, Borrelia afzelii*, and *Borrelia garinii*. The term *B. burgdorferi* s.l. (sensu lato) encompasses at least 17 *Borrelia* species (Table A-1 of WO 2015/104396 A1). These species occur in different geographic regions, and live in nature in enzootic cycles involving ticks of the *Ixodes ricinus* complex (also called *Ixodes persulcatus* complex) and a wide range of animal hosts. Four *Borrelia* species are responsible for the majority of infections in humans: *B. burgdorferi* s.s. (sensu stricto), *B. afzelii, B. bavariensis* and *B. garinii*. An additional species causing LB in humans, *B. mayonii*, has recently been identified (Pritt et al., 2016, Lancet Infect. Dis. 16:556-64). Three other species, *B. lusitaniae, B. bissettii* and *B. spielmanii*, have occasionally been detected in humans, but their role in Lyme borreliosis is uncertain at present. New species of *Borrelia* are still being identified.

As detailed above, *Borrelia* outer surface protein A (OspA) is an abundant immunogenic lipoprotein of *Borrelia* of particular interest because of its potential as a vaccine candidate. OspA of *B. burgdorferi* s.l. is a basic lipoprotein that has a molecular mass of approximately 28 kDa and is encoded on a linear plasmid. It is expressed by the spirochetes only when it is in the gut of the tick vector. During tick feeding, the incoming blood from the host results in environmental changes in the tick gut which cues the spirochetes to down regulate OspA. After down regulation of OspA the spirochetes migrate to tick vector salivary glands and from there to the host. The different host environments encountered by the spirochetes necessitates their differential regulation of protein expression for infection and survival in the diverse milieus. Thus, OspA antibodies produced by vaccination do not fight infection in the body of the host, but rather enter the gut of the tick when it takes a blood meal. Therefore, the antibodies neutralize the spirochetes and block the migration of bacteria from the midgut to the salivary glands of the tick, the route through which *Borrelia* enters the vertebrate host. Thus, OspA-specific antibodies prevent the transmission of *Borrelia* from the tick vector to the human host.

An important aspect of the OspA protein is the presence of an N-terminal lipid moiety; that is, fatty acids with a chain length of between about C14 and C20 with or without double bonds, attached to an N-terminal cysteine residue, a feature which enhances the immunogenicity of the OspA protein. It has been shown that poorly-immunogenic synthetic peptides induce stronger antibody responses when lipidated; for example, when covalently coupled to Pam$_3$Cys (Bessler and Jung, 1992, Research Immunology 143:548-552; see also FIG. 8), a fatty acid substitution found at the amino terminus of many bacterial lipoproteins that are synthesized with a signal sequence specifying lipid attachment. Additionally, the Pam$_3$Cys moiety was shown to enhance immune responses to OspA in mice, partially through its interaction with TLR-2/1 (Yoder, et al., 2003, Infection and Immunity 71:3894-3900). Therefore, the addition of an N-terminal lipid moiety to an OspA chimera, fusion protein or derivative would be expected to enhance the immunogenicity and protective capacity.

As detailed herein, the immunogenic polypeptides of the present invention are characterized by the amino acid sequences of SEQ ID NO: 9, SEQ ID NO: 10, SEQ ID NO: 12 and SEQ ID NO: 13.

The amino acid sequence of SEQ ID NO: 9 relates to a protein also referred to as Variant 2 with a β-type disulfide bond (indicated by *). It comprises epitopes derived from ST1, ST4 and ST5 and has the following amino acid sequence:

```
                                               (SEQ ID NO: 9)
FNEKGEISEKTIVRANGTRLEYTDIKSDKTGKAKEVLKDFTLEGTVAADK

VTLKVTC*GTVTLSKHIPNSGEITVELDDTDSSAATKKTAAWDSNTSTLT

ITVNSKKTKNLVFTKEDTITVQNYDSNGTNLEGKAVETITLKELC*NALK
```

The amino acid sequence of SEQ ID NO: 10 relates to a protein also referred to as Variant 3 with a β-type disulfide bond (indicated by *). It comprises epitopes derived from ST1, ST4 and ST5 and has the following amino acid sequence:

```
                                              (SEQ ID NO: 10)
FNAKGELSEKTILRANGTRLEYTEIKSDGTGKAKEVLKDFALEGTVAADG

KVTLKVTC*GTVTLSKNISKSGEITVALDDTDSSAATKKTAAWDSGTSTL

TITVNSKKTKQLVFTKEDTITVQNYDSNGTNLEGKAVEITTLKELC*NAL

K
```

The amino acid sequence of SEQ ID NO: 12 relates to a protein also referred to as Variant 5 with a β-type disulfide bond (indicated by *). It comprises epitopes derived from ST2, ST3 and ST6 and has the following amino acid sequence:

```
                                                    (SEQ ID NO: 12)
FNEKGELSAKTMTRENGTKLEYTEMKSDGTGKAKEVLKNFTLEGKVANDK

VTLEVKC*GTVTLSKEIAKSGEVTVALNDTNTTRATKKTGKWDSKTSTLT

ISVNSQKTKNLVFTKEDTITVQNYDSAGTNLEGSPAEIKDLAELC*AALK
```

The amino acid sequence of SEQ ID NO: 13 relates to a protein also referred to as Variant 6 with a β-type disulfide bond (indicated by *). It comprises epitopes derived from ST2, ST3 and ST6 and has the following amino acid sequence:

```
                                                    (SEQ ID NO: 13)
FNEKGELSAKTMTRENGTKLEYTEMKSDGTGKAKEVLKNFTLEGKVANDK

VTLEVKC*GTVTLSKEIAKSGEVTVALNDTNTTQATKKTGAWDSKTSTLT

ISVNSKKTKNLVFTKEDTITVQNYDSAGTNLEGSPAEIKDLAELC*AALK
```

The above peptides and variants thereof may be divided into two groups. In accordance with the present invention a peptide of group (i) also referred to as peptide (i) includes a peptide with an amino acid sequence selected from the group consisting of SEQ ID NO: 9 and SEQ ID NO: 10, or an immunogenic variant thereof, wherein said immunogenic variant has at least 90% sequence identity with SEQ ID NO: 9 or SEQ ID NO: 10. A peptide of group (ii) also referred to as peptide (ii) includes a peptide with an amino acid sequence selected from the group consisting of SEQ ID NO: 12 and SEQ ID NO: 13, or an immunogenic variant thereof, wherein said immunogenic variant has at least 90% sequence identity with SEQ ID NO: 12 or SEQ ID NO: 13.

Sequence identity, as known in the art and as used herein, is the relationship between two or more peptide or polypeptide (amino acid) sequences, as determined by comparing the sequences. In the art, identity also means the degree of sequence relatedness between polypeptide or polynucleotide sequences, as the case may be, as determined by the match between strings of such sequences. Identity can be readily calculated. While a number of methods exist to measure identity between two polynucleotides or two polypeptide sequences, the term is well known to skilled artisans (e.g. *Sequence Analysis in Molecular Biology*, von Heinje, G., Academic Press, 1987). Preferred methods to determine identity are designed to give the largest match between the sequences tested. Methods to determine identity are codified in computer programs. Preferred computer program methods to determine identity between two sequences include, but are not limited to, the GCG program package (Devereux, J. et al., 1984), BLASTP, BLASTN, and FASTA (Altschul, S. et al., 1990).

In preferred embodiments of aspects of the present invention,
- the immunogenic variant has at least 91%, 92%, 93%, or 94%, preferably at least 95%, more preferably at least 96%, more preferably 97%, more preferably 98%, even more preferably 99% sequence identity to the amino acid sequence of SEQ ID NO: 9; OR
- the immunogenic variant has at least 91%, 92%, 93%, or 94%, preferably at least 95%, more preferably at least 96%, more preferably 97%, more preferably 98%, even more preferably 99% sequence identity to the amino acid sequence of SEQ ID NO: 10; OR
- the immunogenic variant has at least 91%, 92%, 93%, or 94%, preferably at least 95%, more preferably at least 96%, more preferably 97%, more preferably 98%, even more preferably 99% sequence identity to the amino acid sequence of SEQ ID NO: 12; OR
- the immunogenic variant has at least 91%, 92%, 93%, or 94%, preferably at least 95%, more preferably at least 96%, more preferably 97%, more preferably 98%, even more preferably 99% sequence identity to the amino acid sequence of SEQ ID NO: 13.

According to the present invention, the peptides i) and/or ii) are comprised in an immunogenic polypeptide. The term "immunogenic" in the context of a compound or composition means that the immunogenic compound or composition has the property of inducing the production of antibodies that specifically hind an outer surface protein A (OspA) protein. In certain aspects, the immunogenic compound or composition has the property of inducing production of antibodies that specifically bind *Borrelia*. In particular aspects, the immunogenic compound or composition has the property of inducing production of antibodies that neutralize *Borrelia*. In some aspects, the antibodies are produced by an animal. In further aspects, the animal is a mammal. In even further aspects, the mammal is human.

The term "peptide" or "polypeptide" refers to a biological molecule of chains of amino acid monomers linked by peptide (amide) bonds. The covalent chemical bonds are formed when the carboxyl group of one amino acid reacts with the amino group of another. (Poly)peptides of the present invention are continuous and unbranched amino acid chains. The (poly)peptide of the present invention comprises a cysteine bond. The cysteine bond is a β-type disulfide bond, i.e. a disulfide bond between two cysteine residues at the amino acid positions corresponding to amino acids 182 and 269 of OspA serotype 2.

The immunogenic polypeptide of the present invention may comprise or consist of:
- a peptide with an amino acid sequence of SEQ ID NO: 9,
- a peptide having at least 90% sequence identity with SEQ ID NO: 9,
- a peptide with an amino acid sequence of SEQ ID NO: 10,
- a peptide having at least 90% sequence identity with SEQ ID NO: 10,
- a peptide with an amino acid sequence of SEQ ID NO: 12,
- a peptide having at least 90% sequence identity with SEQ ID NO: 12,
- a peptide with an amino acid sequence of SEQ ID NO: 13, and/or
- a peptide having at least 90% sequence identity with SEQ ID NO: 13.

The immunogenic polypeptide of the present invention may also be a fusion protein comprising or consisting of a peptide (i) and a peptide (ii) and optionally a linker to bind peptide (i) to peptide (ii). The fusion protein may comprise or consist of:
- a peptide with an amino acid sequence of SEQ ID NO: 9 or an immunogenic variant thereof as defined above AND a peptide with an amino acid sequence of SEQ ID NO: 12 or an immunogenic variant thereof as defined above,
- a peptide with an amino acid sequence of SEQ ID NO: 9 or an immunogenic variant thereof as defined above AND a peptide with an amino acid sequence of SEQ ID NO: 13 or an immunogenic variant thereof as defined above,
- a peptide with an amino acid sequence of SEQ ID NO: 10 or an immunogenic variant thereof as defined above AND a peptide with an amino acid sequence of SEQ ID NO: 12 or an immunogenic variant thereof as defined above, a peptide with an amino acid sequence of SEQ ID NO: 10 or an immunogenic variant thereof as defined above AND a peptide with an amino acid sequence of SEQ ID NO: 13 or an immunogenic variant thereof as defined above, a peptide with an amino acid sequence of SEQ ID NO: 9 or an immunogenic variant thereof as defined above AND a linker AND a peptide with an amino acid sequence of SEQ ID NO: 12 or an immunogenic variant thereof as defined above, a peptide with an amino acid sequence of SEQ ID NO: 9 or an immunogenic variant thereof as defined above AND a linker AND a peptide with an amino acid sequence of SEQ ID NO: 13 or an immunogenic variant thereof as defined above, a peptide with an amino acid sequence of SEQ ID NO: 10 or an immunogenic variant thereof as defined above AND a linker AND a peptide with an amino acid sequence of SEQ ID NO: 12 or an immunogenic variant thereof as defined above, or a peptide with an amino acid sequence of SEQ ID NO: 10 or an immunogenic variant thereof as defined above AND a linker AND a peptide with an amino acid sequence of SEQ ID NO: 13 or an immunogenic variant thereof as defined above.

In a preferred embodiment of the present invention, peptide (i) is N-terminal to peptide (ii) or peptide (ii) is N-terminal to peptide (i) in the fusion protein of the present invention. In accordance with this the above exemplary fusion protein arrangements may be understood as listing of the components (peptide (i), peptide (ii) and optionally the linker) from N-terminal to C-terminal or C-terminal to N-terminal.

As detailed above, the fusion protein may comprise a linker, which connects peptide (i) and peptide (ii). A linker is a rather short amino acid sequence employed to connect two peptides. It should be designed in order to avoid any negative impact on the peptides, their interaction in subjects to be treated or vaccinated or upon their protective capacity. Preferred are short linkers of at most 23 amino acids, particularly at most 21 amino acids, particularly at most 15 amino acids, especially at most 12 or 8 amino acids. More preferably, the one or more linkers is/are composed of small amino acids in order to reduce or minimize interactions with the peptides, such as glycine, serine and alanine. Preferably, peptide (i) and peptide (ii) are joined by a linker sequence, particularly wherein said linker sequence comprises or consists of ANNQAGQKSSGSTQATTPNLTFE (SEQ ID NO: 32). However, peptide (i), the linker and peptide (ii) may be linked to each other by short peptide bridges of at most 10, 9, 8, 7, 6 or 5 amino acids each, preferably at most 5, 4, 3, 2 or 1 amino acids. Alternatively, peptide (i), and peptide (ii) are linked to each other directly without a peptide bridge or linker.

According to the present invention, the immunogenic polypeptide may be a lipidated protein, also lipoprotein, wherein the lipid moieties, along with the glycerol group, is also referred to as "Lip". According to the invention, Lip comprises one to three lipids such as $C_{14-20}$ alkyl and/or $C_{14-20}$ alkenyl attached to a glycerol and an amino group of an N-terminal cysteine of the polypeptide of the invention, or preferably wherein Lip is a moiety of formula (I) below,

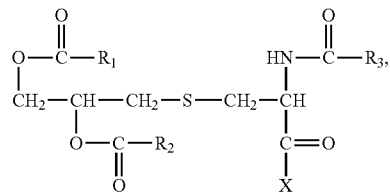

Formula (I)

In which one of $R_1$, $R_2$ or $R_3$ is $C_{14}$-$C_{20}$ alkyl or alkenyl, and each of the others, independently, is $C_{14}$-$C_{20}$ alkyl or $C_{14}$-$C_{20}$ alkenyl, and X is an amino acid sequence attached to the cysteine residue shown in Formula (I). More preferably, Lip plus the N-terminal cysteine of the polypeptide is N-palmitoyl-S-(2RS)-2,3-bis-(palmitoyloxy) propyl cysteine (referred to herein as "Pam₃Cys"; see FIG. 8) and is connected via the carbonyl C of the cysteine to said amino acid sequence of the invention. In Formula (I) above, $R_1$, $R_2$ and $R_3$ would be palmitoyl moieties and X is an amino acid sequence attached to the cysteine residue.

In accordance with this, the immunogenic polypeptide according to the present invention may comprise an N-terminal lipidation signal sequence. Lipidation of a protein with an N-terminal lipidation signal sequence, such as those present on a nascent OspA polypeptide, occurs in the E. coli expression vector by the step-wise action of the enzymes diacylglyceryl transferase, signal peptidase II and transacylase, respectively. The first step is the transfer of a diacylglyceride to the cysteine sulfhydryl group of the unmodified prolipoprotein, followed by the cleavage of the signal peptide by signal peptidase II and, finally, the acylation of the amino group of the N-terminal cysteine of the apolipoprotein. The result is the placement of one lipid and a glycerol group with two further lipids attached on an N-terminal cysteine residue of the polypeptide. The lipidation signal sequence, which is cleaved off during lipidation, is not present in the final polypeptide sequence. A preferred lipidation signal sequence is MKATKLVLGAVILGSTL-LAGCSS (SEQ ID NO: 30). When the lipidation signal sequence of SEQ ID NO: 30 is cleaved, the three most C-terminal residues (CSS) of SEQ ID NO: 30 remain at the N-terminal end of the polypeptide, resulting in a lipidated N-terminal cysteine residue followed by two serine residues.

For purification or detection purposes the immunogenic peptide may also comprise a marker or tag sequence. Suitable markers include without limitation a tag (e.g. 6 His (or HexaHis) tag, Strep tag, HA tag, c-myc tag or glutathione S-transferase (GST-tag). Preferably, the tag is LEHHHHHH (SEQ ID NO: 75) or HHHHHH (SEQ ID NO: 31), especially HHHHHH (SEQ ID NO: 31).

Preferred immunogenic polypeptides of the present invention include those of SEQ ID NO: 9, 10, 12 or 13, the lipidated Variants with or without C-terminal His-tag of SEQ ID NO: 15, 16, 18, 19, 21, 22, 24 or 25, the lipidated fusion protein V3-L2-V5 with or without C-terminal His-tag of SEQ ID NO: 26 or 28, respectively. The lipidated multivalent OspA fusion protein V3-L2-V5 is also referred to interchangeably herein as "Lip-V3-L2-V5".

A highly preferred immunogenic polypeptide of the present invention is a fusion protein comprising or consisting of the amino acid sequence of SEQ ID NO: 28 (Lip-V3-L2-V5). The lipidated fusion protein comprises a lipidated N-terminal CSS peptide ("LipCSS"), which remains after proteolytic processing from a lipidation signal sequence at the N-terminus (SEQ ID NO: 30), Variant 3 (SEQ ID NO: 10; indicated by underline), the linker L2 (SEQ ID NO: 32; italic font) and Variant 5 (SEQ ID NO: 12; indicated by dashed underline) as follows:

```
                                            (SEQ ID NO: 28)
LipCSSFNAKGELSEKTILRANGTRLEYTEIKSDGTGKAKEVLKDFALEG

TVAADGKVTLKVTCGTVTLSKNISKSGEITVALDDTDSSAATKKTAAWDS

GTSTLTITVNSKKTKQLVFTKEDTITVQNYDSNGTNLEGKAVEITTLKEL

CNALKGTSANNQAGQKSSGSTQATTPNLTFEKYSFNEKGELSAKTMTREN

GTKLEYTEMKSDGTGKAKEVLKNFTLEGKVANDKVTLEVKCGTVTLSKEI

AKSGEVTVALNDTNTTRATKKTGKWDSKTSTLTISVNSQKTKNLVFTKED

TITVQNYDSAGTNLEGSPAEIKDLAELCAALK
```

In a further aspect, the present invention relates to a nucleic acid encoding the immunogenic polypeptide of the present invention.

For the purposes of the invention the term "nucleic acid(s)" generally refers to any polyribonucleotide or polydeoxyribonucleotide, which may be unmodified RNA or DNA or modified RNA or DNA including single and double-stranded regions/forms.

The term "nucleic acid encoding a polypeptide" as used herein encompasses polynucleotides that include a sequence encoding a peptide or polypeptide of the invention. The term also encompasses polynucleotides that include a single continuous region or discontinuous regions encoding the peptide or polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

It will be appreciated by those of ordinary skill in the art that, as a result of the degeneracy of the genetic code, there are many nucleotide sequences that encode a polypeptide as described herein. Some of these polynucleotides bear minimal similarity to the nucleotide sequence of any native (i.e., naturally occurring) gene. Nonetheless, polynucleotides that vary due to differences in codon usage are specifically contemplated by the present invention, for example polynucleotides that are optimized for human and/or primate and/or E. coli codon selection.

Sequences encoding a desired polypeptide may be synthesized, in whole or in part, using chemical methods well known in the art (see, e.g., Caruthers, M. H. et al., 1980. Nucl. Acids Res. Symp. Ser. pp. 215-223, Horn et al., 1980. Nucl. Acids Res. Symp. Ser. pp. 225-232). Alternatively, the protein itself may be produced using chemical methods to synthesize the amino acid sequence of a polypeptide, or a portion thereof. For example, peptide synthesis can be performed using various solid-phase techniques (Roberge et al., 1995. Science 269:202-204) and automated synthesis may be achieved, for example, using the AST 431 A Peptide Synthesizer (Perkin Elmer, Palo Alto, CA).

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, change codon preference, produce splice variants, or introduce mutations, and so forth.

"Nucleic acid molecule" as used herein generally refers to any ribonucleic acid molecule or deoxyribonucleic acid molecule, which may be unmodified RNA or DNA or modified RNA or DNA. Thus, for instance, nucleic acid molecule as used herein refers to at least single- and double-stranded DNA, hybrid molecules comprising DNA and RNA that may be single-stranded or, more typically, double-stranded, or a mixture of single- and double-stranded regions. As used herein, the term nucleic acid molecule includes DNA or RNA molecules as described above that contain one or more modified bases. Thus, DNA or RNA molecules with backbones modified for stability or for other reasons are "nucleic acid molecule" as that term is intended herein. Moreover, DNA or RNA species comprising unusual bases, such as inosine, or modified bases, such as tritylated bases, to name just two examples, are also nucleic acid molecules as defined herein. It will be appreciated that a great variety of modifications have been made to DNA and RNA molecules that serve many useful purposes known to those of skill in the art. The term nucleic acid molecule as used herein embraces such chemically, enzymatically or metabolically modified forms of nucleic acid molecules, as well as the chemical forms of DNA and RNA characteristic of viruses and cells, including simple and complex cells, inter alia. The term nucleic acid molecule also encompasses short nucleic acid molecules often referred to as oligonucleotide(s). The terms "polynucleotide" and "nucleic acid" or "nucleic acid molecule" are used interchangeably herein.

The nucleic acids according to the present invention may be chemically synthesized. Alternatively, the nucleic acids can be isolated from *Borrelia* and modified by methods known to one skilled in the art. The same applies to the polypeptides according to the present invention.

Furthermore, the nucleic acid of the present invention can be functionally linked, using standard techniques such as cloning, to any desired sequence(s), whether a *Borrelia* regulatory sequence or a heterologous regulatory sequence, heterologous leader sequence, heterologous marker sequence or a heterologous coding sequence to create a fusion gene.

Nucleic acid molecules of the present invention may be in the form of RNA, such as mRNA or cRNA, or in the form of DNA, including, for instance, cDNA and genomic DNA obtained by cloning or produced by chemical synthesis techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

Preferred nucleic acids are those coding for the immunogenic polypeptides of the present invention, particularly those of SEQ ID NO: 9, 10, 12 or 13, the lipidated Variants with or without a C-terminal His-tag of SEQ ID NO: 15, 16, 18, 19, 21, 22, 24 or 25, the lipidated fusion protein V3-L2-V5 with or without a C-terminal His-tag of SEQ ID NO: 26 or 28, respectively. A highly preferred nucleic acid comprises or consists of the nucleic acid sequence of SEQ ID NO: 29.

The products of the present invention, particularly the polypeptides and nucleic acids, are preferably provided in isolated form, and may be purified to homogeneity. The term "isolated" as used herein means separated "by the hand of man" from its natural state; i.e., if it occurs in nature, it has been changed or removed from its original environment, or both. For example, a naturally-occurring nucleic acid molecule or a polypeptide naturally present in a living organism in its natural state is not "isolated", but the same nucleic acid molecule or polypeptide separated from the coexisting materials of its natural state is "isolated", as the term is employed herein. As part of or following isolation, such nucleic acid molecules can be joined to other nucleic acid molecules, such as DNA molecules, for mutagenesis, to form fusion genes, and for propagation or expression in a host, for instance. The isolated nucleic acid molecules, alone or joined to other nucleic acid molecules such as vectors, can be introduced into host cells, in culture or in whole organisms. Introduced into host cells in culture or in whole organisms, such DNA molecules still would be isolated, as the term is used herein, because they would not be in their naturally-occurring form or environment. Similarly, the nucleic acid molecules and polypeptides may occur in a composition, such as medium formulations, solutions for introduction of nucleic acid molecules or polypeptides, for example, into cells, compositions or solutions for chemical or enzymatic reactions, for instance, which are not naturally occurring compositions, and, therein remain isolated nucleic acid molecules or polypeptides within the meaning of that term as it is employed herein.

The nucleic acid of the present invention may be comprised in a vector or in a cell. The vector may comprise the above-mentioned nucleic acid in such a manner that the vector is replicable and can express the protein encoded by the nucleotide sequence in a host cell.

Accordingly, in a further aspect the present invention relates to a vector comprising a nucleic acid of the invention. It may be linked to an inducible promoter such that when the promoter is induced, a polypeptide encoded by the nucleic acid is expressed. In a preferred embodiment, the vector is pET28b(+) (http://www.addgene.org/vector-database/2566/). Preferably, said vector comprises an inducible promoter, which is activated by addition of a sufficient quantity of IPTG (Isopropyl β-D-1-thiogalactopyranoside) preferably to the growth medium. Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM. Alternatively the promoter may be induced by a change in temperature or pH.

In a still further aspect, the present invention relates to a cell, preferably a host cell, comprising a nucleic acid of the invention. For recombinant production of the polypeptides of the invention, host cells can be genetically engineered to incorporate expression systems or portions thereof of the nucleic acid of the invention. Introduction of a nucleic acid into a host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include gram negative bacterial cells, such as cells of *E. coli, Acinetobacter, Actinobacillus, Bordetella, Brucella, Campylobacter, Cyanobacteria, Enterobacter, Erwinia, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio, Yersinia*. In one embodiment, the host cell is an Escherichia coli cell. In a preferred embodiment, the host cell is an E. cob BL21(DE3) cell or an *E. coli* BL21 Star™ (DE3) cell. Preferably, the host cell is *E. coli*.

Alternatively, gram positive bacterial cells may also be used. A great variety of expression systems can be used to produce the polypeptides of the invention. In one embodiment the vector is derived from bacterial plasmids. Generally any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL (supra).

In one embodiment of the current invention, the cells are grown under selective pressure, such as in the presence of antibiotics, preferably kanamycin. In another embodiment, cells are grown in the absence of antibiotics.

A great variety of expression vectors can be used to express the polypeptides according to the present invention. Generally, any vector suitable to maintain, propagate or express nucleic acids to produce a polypeptide in a host may be used for expression in this regard. In accordance with this aspect of the invention the vector may be, for example, a plasmid vector, a single- or double-stranded phage vector or a single- or double-stranded RNA or DNA viral vector. Starting plasmids disclosed herein are either commercially available, publicly available, or can be constructed from available plasmids by routine application of well-known, published procedures. Preferred among vectors, in certain respects, are those for expression of nucleic acid molecules and the polypeptides according to the present invention. Nucleic acid constructs in host cells can be used in a conventional manner to produce the gene product encoded by the recombinant sequence. Alternatively, the polypeptides according to the present invention can be synthetically produced by conventional peptide synthesizers.

In addition, the present invention relates to a host cell comprising this vector. Representative examples of appropriate host cells include bacteria, such as streptococci, staphylococci, *E. coli, Streptomyces* and *Bacillus subtilis*; fungi, such as yeast and *Aspergillus*; insect cells such as *Drosophila* S2 and *Spodoptera* Sf9 cells; mammalian cells such as CHO, COS, HeLa, 0127, 3T3, BHK, 293 or Bowes melanoma cells; and plant cells. Preferably, the host cell is *E. coli*. Cell-free translation systems can also be employed to produce such proteins using RNA derived from the DNA construct of the present invention.

In order to express the desired amino acid sequence practically by introducing the vector according to the present invention into a host cell, the vector may contain, in addition to the nucleic acid sequence according to the present invention, other sequences for controlling the expression (e.g., promoter sequences, terminator sequences and enhancer sequences) and gene markers for selecting microorganisms, insect cells, animal culture cells, or the like (e.g., neomycin resistance genes and kanamycin resistance genes). Furthermore, the vector may contain the nucleic acid sequence according to the present invention in a repeated form (e.g., in tandem). The vector may be constructed based on procedures which are conventionally used in the field of genetic engineering.

The host cells may be cultured in an appropriate medium, and the protein according to the present invention may be obtained from the culture product. The protein according to the present invention may be recovered from the culture medium and purified in the conventional manner.

Accordingly, the present invention also relates to a process for producing a cell which expresses a immunogenic polypeptide according to the present invention, comprising transforming or transfecting a suitable host cell with the vector according to the present invention or a process for producing the immunogenic polypeptide according to the present invention, comprising expressing the nucleic acid molecule according to the present invention.

Alternatively, a method for producing the immunogenic polypeptide as defined above may be characterized by the following steps:
 a) introducing a vector encoding the immunogenic polypeptide according to the invention into a host cell,
 b) growing the host cell under conditions allowing for expression of said immunogenic polypeptide,
 c) homogenizing said host cell, and
 d) subjecting the host cell homogenate to purification steps.

The invention further relates to a method for producing a polypeptide as defined above, characterized by the following steps:
 a) introducing a nucleic acid encoding a polypeptide into a vector,
 b) introducing said vector into a host cell,
 c) growing said host cell under conditions allowing for expression of polypeptide,
 d) homogenizing said host cell,
 e) enriching polypeptide in the lipid phase by phase separation, and
 f) further purifying over a gel filtration column.

The invention further relates to a method for producing a polypeptide as defined above, characterized by the following steps:
 a) introducing a nucleic acid encoding a polypeptide into a vector,
 b) introducing said vector into a host cell,
 c) growing said host cell under conditions allowing for expression of polypeptide,
 d) homogenizing said host cell,
 e) enriching polypeptide in the lipid phase by phase separation,
 g) purifying over a gel filtration column, and
 h) optionally, further processing over a buffer exchange column.

Another aspect of the present invention relates to a pharmaceutical composition comprising
 (i) the immunogenic polypeptide according to the present invention and/or the nucleic acid according to the present invention; and
 (ii) optionally a pharmaceutically acceptable excipient.

A pharmaceutical composition is a composition intended for use in the pharmaceutical field or as pharmaceutic. It may optionally contain any pharmaceutically acceptable carrier or excipient, such as buffer substances, stabilizers or further active ingredients, especially ingredients known in connection with pharmaceutical compositions and/or vaccine production. In general, the nature of the excipients will depend on the particular mode of administration being employed. Such carriers may include, but are not limited to, saline, buffered saline, dextrose, water, glycerol, ethanol and combinations thereof. The formulation should suit the mode of administration. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically neutral carriers, pharmaceutical compositions to be administered can contain minor amounts of non-toxic auxiliary substances, such as wetting or emulsifying agents, preservatives, and pH buffering agents and the like.

A preferable carrier or excipient for the polypeptides according to the present invention in their diverse embodiments, or a nucleic acid molecule according to the present invention is an immunostimulatory compound such as an adjuvant for further stimulating the immune response to the polypeptide according to the present invention or a coding nucleic acid molecule thereof.

In one embodiment the pharmaceutical composition further comprises an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide or aluminum phosphate, but may also be other metal salts such as those of calcium, magnesium, iron or zinc, or may be an insoluble suspension of acylated tyrosine, or acylated sugars, cationically or anionically derivatized saccharides, or polyphosphazenes. In a preferred embodiment, the pharmaceutical composition is adjuvanted with aluminium hydroxide.

The use of an aluminium hydroxide and/or aluminium phosphate adjuvant is particularly preferred, and antigens are generally adsorbed to these salts. Preferably, aluminium hydroxide is present at a final concentration of 0.15%. A useful aluminium phosphate adjuvant is amorphous aluminium hydroxyphosphate with $PO_4/Al$ molar ratio between 0.84 and 0.92. Another adjuvant useful in the current invention is an aluminium salt that is able to provide an aqueous composition having less than 350 ppb heavy metal based on the weight of the aqueous composition. A further useful aluminium-based adjuvant is AS04, a combination of aluminium hydroxide and monophosphoryl lipid A (MPL).

Immunostimulatory compounds may be used in compositions of the invention. Preferably, the immunostimulatory compound in pharmaceutical compositions according to the present invention is selected from the group of polycationic substances, especially polycationic peptides, immunostimulatory nucleic acids molecules, preferably immunostimulatory dcoxynucleotides, oil-in-water or water-in-oil emulsions, MF59, aluminium salts, Freund's complete adjuvant, Freund's incomplete adjuvant, neuroactive compounds, especially human growth hormone, or combinations thereof.

As detailed above, the pharmaceutical composition may comprise a stabilizer. The term "stabilizer" refers to a substance or vaccine excipient which protects the immunogenic composition of the vaccine from adverse conditions, such as those which occur during heating or freezing, and/or prolongs the stability or shelf-life of the immunogenic composition in a stable and immunogenic condition or state. Examples of stabilizers include, but are not limited to, sugars, such as sucrose, lactose and mannose; sugar alcohols, such as mannitol; amino acids, such as glycine or glutamic acid; and proteins, such as human serum albumin or gelatin.

In one embodiment, the composition comprises between 5 mM and 50 mM sodium phosphate, between 100 and 200 mM sodium chloride, between 5 mM and 25 mM L-methionine, between 2.5% and 10% Sucrose, between 0.01% and 0.1% Tween-20 (Polysorbate-20) and between 0.1% and 0.2% (w/v) aluminium hydroxide. More preferably, the formulation comprises 10 mM sodium phosphate, 150 mM sodium chloride, 10 mM L-Methionine, 5% Sucrose, 0.05% Tween 20 and 0.15% (w/v) aluminium hydroxide at pH 6.7±0.2. Even more preferably, the formulation comprises at least one, at least two, at least three mutant OspA heterodimers according to the invention. In a further embodiment, the pharmaceutical composition comprises sodium phosphate, sodium chloride, L-methionine, sucrose and Polysorbate-20 (Tween-20) at a pH of 6.7±0.2. Preferably, the pharmaceutical composition also comprises aluminium hydroxide, preferably at a concentration of 0.15%. In another preferred embodiment, the pharmaceutically acceptable excipient comprises L-methionine.

The pharmaceutical compositions of the present invention may be administered in any effective, convenient manner including, for instance, administration by topical, oral, anal, vaginal, intravenous, intraperitoneal, intramuscular, subcutaneous, intranasal, intratracheal or intradermal routes, among others. In a preferred embodiment, the pharmaceutical compositions are administered subcutaneously or intramuscularly, most preferably intramuscularly. In therapy or as a prophylactic, the active agent of the pharmaceutical composition of the present invention may be administered to an individual as an injectable composition, for example as a sterile aqueous dispersion, preferably isotonic.

Alternatively the composition, preferably the pharmaceutical composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

The pharmaceutical composition of the invention includes kits which comprise one or more pharmaceutical formulations for administration to a subject packaged in a manner which facilitates their use for administration to subjects. In a preferred embodiment, the kits comprise the formulation in a final volume of 2 mL, more preferably in a final volume of 1 mL.

In a specific embodiment, the invention includes kits for producing a single dose administration unit. The kits, in various aspects, each contain both a first container having a dried protein and a second container having an aqueous formulation. Also included within the scope of this invention are kits containing single and multi-chambered pre-filled syringes (e.g., liquid syringes and lyosyringes).

In another embodiment, such a kit includes a pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In one aspect, the kit contains a first container having a therapeutic protein or peptide composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations. In a further aspect, the pharmaceutical composition of the invention may be pre-mixed in a vial, preferably in a syringe.

In a preferred embodiment, the pharmaceutical composition comprises the immunogenic polypeptide comprising or consisting of the sequence of SEQ ID NO: 28 (Lip-V3-L2-V5) and optionally a pharmaceutically acceptable excipient.

The pharmaceutical composition can contain a range of different antigens. Examples of antigens are whole-killed or attenuated organisms, sub-fractions of these organisms, proteins, or, in their most simple form, peptides. Antigens can also be recognized by the immune system in the form of glycosylated proteins or peptides and may also be or contain polysaccharides or lipids. Short peptides can be used, since cytotoxic T cells (CTL) recognize antigens in the form of short, usually 8-11 amino acids long, peptides in conjunction with major histocompatibility complex (MHC). B cells can recognize linear epitopes as short as 4 to 5 amino acids, as well as three-dimensional structures (conformational epitopes).

In one embodiment of the invention, the pharmaceutical composition further comprises at least one additional antigen from *Borrelia* or a pathogen other than *Borrelia* (herein referred to generically as "combination pharmaceutical composition or vaccine"). In a preferred embodiment, the at least one additional antigen is derived from a *Borrelia* species causing Lyme borreliosis. In various aspects, the at least one additional antigen is derived from another pathogen, preferably a tick-borne pathogen. In a further aspect, the pathogen causes Rocky Mountain spotted fever, Human granulocytic ehrlichiosis (HGE), Sennetsu Fever, Human Monocytic Ehrlichiosis (HME), Anaplasmosis, Boutonneuse fever, *Rickettsia parkeri* Rickettsiosis, Southern Tick-Associated Rash Illness (START), Helvetica Spotted fever, 364D Rickettsiosis, African spotted fever, Relapsing fever, Tularemia, Colorado tick fever, Tick-borne encephalitis (TBE, also known as FSME), Crimean-Congo hemorrhagic fever, Q fever, Omsk hemorrhagic fever, Kyasanur forest disease, Powassan encephalitis, Heartland virus disease or Babesiosis. In a further aspect, the disease is Japanese encephalitis.

In a further embodiment, the at least one additional antigen is derived from a vector-borne, preferably a tick-borne pathogen. Preferably, the additional antigen is from a tick-borne pathogen, particularly wherein the tick-borne pathogen is selected from the group comprising *Borrelia hermsii, Borrelia parkeri, Borrelia duttoni, Borrelia miyamotoi, Borrelia turicatae, Rickettsia rickettsii, Rickettsia*

*australis, Rickettsia conorii, Rickettsia helvetica, Rickettsia parkeri, Francisella tularensis, Anaplasma phagocytophilum, Ehrlichia sennetsu, Ehrlichia chaffeensis, Coxiella burnetii* and *Borrelia lonestari*, Tick-borne encephalitis virus (TBEV), Colorado tick fever virus (CTFV), Crimean-Congo hemorrhagic fever virus (CCHFV), Kyasanur forest disease virus (KFDV), Powassan virus, Heartland virus, Omsk Hemorrhagic Fever virus (OHFV) and *Babesia* spp.

In a preferred embodiment, the invention relates to a pharmaceutical composition of the present invention and an additional antigen as defined above, wherein the at least one additional antigen is comprised in a second composition, particularly wherein the second composition is a vaccine, preferably a tick-borne encephalitis vaccine, a Japanese encephalitis vaccine or a Rocky Mountain spotted fever vaccine. The first composition may be a vaccine as well. The combination pharmaceutical composition or vaccine of the invention comprises any composition discussed herein in combination with at least a second (vaccine) composition. In some aspects, the second vaccine composition protects against a vector-borne disease, preferably a tick-borne disease. In various aspects, the second vaccine composition has a seasonal immunization schedule compatible with immunization against *Borrelia* infection or Lyme borreliosis. In other aspects, combination vaccines are useful in the prevention of multiple diseases for use in geographical locations where these diseases are prevalent.

In one aspect, the second composition is a vaccine selected from the group consisting of a tick-borne encephalitis vaccine, a Japanese encephalitis vaccine, and a Rocky Mountain Spotted Fever vaccine. In a preferred aspect, the vaccine composition is FSME-IMMUN® (Baxter), Encepur® (GSK Vaccines), EnceVir® (Microgen NPO) or TBE Moscow Vaccine'® (Chumakov Institute of Poliomyelitis and Viral Encephalitides of Russian Academy of Medical Sciences). In another preferred aspect, the vaccine composition is IXIARO®/JESPECT® (Valneva SE), JEEV® (Biological E, Ltd.) or IMOJEV® (Sanofi Pasteur).

In another preferred embodiment, the pharmaceutical composition of the present invention further comprises an immunostimulatory substance, preferably selected from the group consisting of polycationic polymers, especially polycationic peptides, immunostimulatory oligodeoxynucleotides (ODNs), especially oligo(dIdC)$_{13}$ (SEQ ID NO: 40), peptides containing at least two LysLeuLys motifs, especially peptide KLKLLLLLKLK (SEQ ID NO: 39), neuroactive compounds, especially human growth hormone, aluminium hydroxide or aluminium phosphate, Freund's complete or incomplete adjuvants, or combinations thereof. Preferably, the immunostimulatory substance is a combination of either a polycationic polymer and immunostimulatory deoxynucleotides or of a peptide containing at least two LysLeuLys motifs and immunostimulatory deoxynucleotides, preferably a combination of KLKLLLLLKLK (SEQ ID NO: 39) and oligo(dIdC)$_{13}$ (SEQ ID NO: 40). More preferably, said polycationic peptide is polyarginine.

In a preferred embodiment, the pharmaceutical composition which is a vaccine, this vaccine may further comprise a pharmaceutically acceptable excipient. In a preferred embodiment, the excipient is L-methionine.

In another aspect, the present invention relates to the immunogenic polypeptide of the invention, the nucleic acid of the invention or the pharmaceutical composition of the invention for use as a medicament, particularly as a vaccine.

The vaccine preparations containing pharmaceutical compositions of the present invention may be used to protect a mammal, especially a human, susceptible to *Borrelia* infection or treat a mammal, especially a human, with a *Borrelia* infection, by means of administering said vaccine via a systemic or mucosal route. These administrations may include injection via the intramuscular, intraperitoneal, intradermal or subcutaneous routes; or via mucosal administration to the oral/alimentary, respiratory or genitourinary tracts. Although the vaccine of the invention may be administered as a single dose, components thereof may also be co-administered together at the same time or at different times.

In a preferred embodiment the pharmaceutical composition is a vaccine composition. Preferably, such vaccine composition is conveniently in injectable form. Conventional adjuvants may be employed to enhance the immune response. A suitable unit dose for vaccination with a protein antigen is for adults between 0.02 µg and 3 µg antigen per kg body weight and for children between 0.2 µg and 10 µg antigen per kg body weight, and such dose is preferably administered 1 to 3 times at intervals of 2 to 24 weeks.

At the indicated dose range, no adverse toxicological effects are expected with the compounds of the invention, which would preclude their administration to suitable individuals.

In still another aspect, the present invention relates to the immunogenic polypeptide of the invention, the nucleic acid of the invention or the pharmaceutical composition of the invention for use in a method of treating or preventing a *Borrelia* infection, particularly a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. iurdi* or *B. sinica* infection, preferably a *B. burgdorferi* s.s., *B. afzelii* or *B. garinii* infection.

In connection therewith, it should be noted that the various *Borrelia* species, including *B. burgdorferi* s.l., comprise several species and strains including those disclosed herein. A disease related, caused or associated with the bacterial infection to be prevented and/or treated according to the present invention includes Lyme borreliosis (Lyme disease). Further aspects, symptoms, stages and subgroups of Lyme borreliosis as well as specific groups of patients suffering from such disease as also disclosed herein, including in the introductory part, are incorporated herein by reference. More specifically, Lyme borreliosis generally occurs in stages, with remission and exacerbations with different clinical manifestation at each stage. Early infection stage 1 consists of localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis.

Alternatively, the present invention relates to the use of the immunogenic polypeptide of the invention, the nucleic acid of the invention or the pharmaceutical composition of the invention in the manufacture of a medicament for use in a method of treating or preventing a *Borrelia* infection, wherein the infection is a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, preferably a *B. burgdorferi* s.s., *B. afzelii* or *B. garinii* infection.

Treatment or treating is the attempted remediation of a health problem, usually following a diagnosis. A treatment treats a problem, and may lead to its cure, but treatments often ameliorate a problem only for as long as the treatment is continued, especially in chronic diseases. Cures are a subset of treatments that reverse illnesses completely or end medical problems permanently. Prevention or preventing is a way to avoid an injury, sickness, or disease in the first place, and generally it will not help someone who is already ill (though there are exceptions). A treatment or cure is applied after a medical problem has already started, whereas prevention is applied before the medical problem is detectable. The treatment or prevention may be in any subject, particularly a mammal such as cat, dog, rat, mouse, cow, horse, rabbit, or primate, especially in a human.

Prevention or preventing refers to measures taken to prevent diseases, rather than curing them or treating their symptoms. The term contrasts in method with curative and palliative medicine. In the context of the present invention prevention of Lyme borreliosis means that the development of Lyme borreliosis is prevented before any signs or symptoms of the disease arc detectable, i.e. at a stage in which the subject is still healthy with respect to Lyme borreliosis.

In the context of *Borrelia* infection, preventing Lyme borreliosis relates to a situation in which e.g. *Borrelia* invasion into the host, the survival of *Borrelia* in the infected host and/or the migration of *Borrelia* to secondary organs etc. is inhibited or prevented, whereas treatment relates to a situation in which the *Borrelia* spirochete has entered the host and replicated, but wherein further replication of the *Borrelia* spirochete is inhibited. In the context of Lyme borreliosis, prevention relates to a situation in which the manifestation of the disease in an infected subject or patient is prevented or inhibited, whereas treatment relates to a situation in which the subject or patient shows signs and symptoms of Lyme borreliosis, which are subsequently ameliorated.

Furthermore, the present invention relates to a method of treating or preventing a *Borrelia* infection in a subject in need thereof comprising the step of administering to the subject a therapeutically-effective amount of the immunogenic polypeptide of the invention, the nucleic acid of the invention or the pharmaceutical composition of the invention. In various aspects, such methods comprise the step of administering any of the vaccine compositions discussed herein or any of the combination vaccines discussed herein to the subject in an amount effective to prevent or treat *Borrelia* infection or Lyme borreliosis.

The term "subject" is used throughout the specification to describe an animal, preferably a mammal, more preferably a human, to whom a treatment or a method according to the present invention is provided. For treatment of those infections, conditions or disease states which are specific for a specific animal such as a human patient, the term patient refers to that specific animal. Preferably, the subject is a human; however, the medical use of the composition may also include animals such as poultry including chicken, turkey, duck or goose, livestock such as horse, cow or sheep, or companion animals such as dogs or cats.

The term "effective amount" is used throughout the specification to describe an amount of the present pharmaceutical composition which may be used to produce an intended result when used in the method of the present invention. In numerous aspects of the present invention, the term effective amount is used in conjunction with treatment or prevention. In other aspects, the term effective amount simply refers to an amount of an agent which produces a result which is seen as being beneficial or useful, including in methods according to the present invention where the treatment or prevention of a *Borrelia* infection is sought.

The term effective amount with respect to the presently described compounds and compositions is used throughout the specification to describe that amount of the compound according to the present invention which is administered to a mammalian patient, especially including a human patient, suffering from a *Borrelia*-associated disease, to reduce, protect from or inhibit a *Borrelia* infection.

A further aspect of the invention is a method for immunizing an animal or human against infection with a *Borrelia* organism, comprising the step of administering to said animal or human an effective amount of the immunogenic polypeptide of the invention, the nucleic acid of the invention or the pharmaceutical composition of the invention, wherein the effective amount is suitable to elicit an immune response in said animal or human. In various aspects, such methods comprise the step of administering any of the immunogenic compositions or vaccine compositions discussed herein to the subject in an amount effective to induce an immunological response. In certain aspects, the immunological response comprises production of an anti-OspA antibody. The method comprises inducing an immunological response in an individual through gene therapy or otherwise, e.g. vaccination, by administering a polypeptide or nucleic acid according to the present invention in vivo in order to stimulate an immunological response to produce antibodies or a cell-mediated T cell response, either cytokine-producing T cells or cytotoxic T cells, to protect said individual from disease, whether or not that disease is already established within the individual.

A further aspect of the invention is a method for stimulating an immune response in an animal or human against a *Borrelia* organism, comprising the step of administering to said animal or human an effective amount of to the immunogenic polypeptide of the invention, the nucleic acid of the invention, the vector of the invention or the pharmaceutical composition of the invention, wherein the effective amount is suitable to stimulate the immune response in said animal or human.

In preferred methods, the *Borrelia* organism is selected from the group comprising *B. burgdorferi*, particularly *B. burgdorferi* s.s., *B. garinii*, *B. afzelii*, *B. andersoni*, *B. bavariensis*, *B. bissettii*, *B. valaisiana*, *B. lusitaniae*, *B. spielmanii*, *B. mayonii*, *B. japonica*, *B. tanukii*, *B. turdi* or *B. sinica*, Preferably *B. burgdorferi* s.s., *B. afzelii* or *B. garinii*.

Specific embodiments of the present invention are summarized in the following. The above definitions and embodiments apply as well:

1. An immunogenic polypeptide comprising peptide (i) and/or peptide (ii), wherein
   peptide (i) is a peptide with an amino acid sequence selected from the group consisting of SEQ ID NO: 9 and SEQ ID NO: 10, or an immunogenic variant thereof, wherein said immunogenic variant has at least 90% sequence identity with SEQ ID NO: 9 or SEQ ID NO: 10; and
   peptide (ii) is a peptide with an amino acid sequence selected from the group consisting of SEQ ID NO: 12 and SEQ ID NO: 13, or an immunogenic variant thereof, wherein said immunogenic variant has at least 90% sequence identity with SEQ ID NO: 12 or SEQ ID NO: 13.

2. An immunogenic polypeptide comprising peptide (i) and peptide (ii), wherein
   peptide (i) is a peptide with an amino acid sequence selected from the group consisting of SEQ ID NO: 9 and SEQ ID NO: 10, or an immunogenic variant thereof, wherein said immunogenic variant has at least 90% sequence identity with SEQ ID NO: 9 or SEQ ID NO: 10; and peptide (ii) is a peptide with an amino acid sequence selected from the group consisting of SEQ ID NO: 12 and SEQ ID NO: 13, or an immunogenic variant thereof, wherein said immunogenic variant has at least 90% sequence identity with SEQ ID NO: 12 or SEQ ID NO: 13.

3. The immunogenic polypeptide of embodiment 2, wherein peptide (i) is N-terminal to peptide (ii).

4. The immunogenic polypeptide of embodiment 2, wherein peptide (ii) is N-terminal to peptide (i).

5. The immunogenic polypeptide of embodiment 2 or 3, wherein peptide (i) and peptide (ii) are joined by a linker sequence.

6. The immunogenic polypeptide of embodiment 5, wherein said linker comprises or consists of ANNQAGQKSSGSTQATTPNLTFE (SEQ ID NO: 32).

7. The immunogenic polypeptide of any of embodiments 1 to 6, further comprising an N-terminal lipidation signal sequence.

8. The immunogenic polypeptide of embodiment 7, wherein the lipidation signal sequence is MKATKLVL-GAVILGSTLLAGCSS (SEQ ID NO: 30).

9. The immunogenic polypeptide of any of embodiments 2 to 8, wherein said immunogenic polypeptide comprises or consists of SEQ ID NO: 28 (Lip-V3-L2-V5).

10. A nucleic acid encoding the immunogenic polypeptide of any of embodiments 1 to 9.

11. The nucleic acid of embodiment 10, wherein said nucleic acid is defined by SEQ ID NO: 29.

12. A vector comprising a nucleic acid molecule according to embodiment 10 or 11.

13. A host cell comprising the nucleic acid of embodiment 10 or 11 or the vector of embodiment 12, wherein said host cell is preferably *E. coli*.

14. A process for producing a cell which expresses the immunogenic polypeptide of any of embodiments 1 to 9, comprising transforming or transfecting a suitable host cell with the vector of embodiment 12.

15. A process for producing the immunogenic polypeptide of any of embodiments 1 to 9, comprising expressing the nucleic acid molecule of embodiment 10 or 11.

16. A method for producing the immunogenic polypeptide of any of embodiments 1 to 9, characterized by the following steps:
  a) introducing a vector encoding the immunogenic polypeptide of any of embodiments 1 to 9 into a host cell,
  b) growing the host cell under conditions allowing for expression of said immunogenic polypeptide,
  c) homogenizing said host cell, and
  d) subjecting the host cell homogenate to purification steps.

17. A pharmaceutical composition comprising the immunogenic polypeptide of any of embodiments 1 to 9 and/or the nucleic acid of embodiment 10 or 11 and optionally a pharmaceutically acceptable excipient.

18. A pharmaceutical composition comprising the immunogenic polypeptide comprising or consisting of the sequence of SEQ ID NO: 28 (Lip-V3-L2-V5) and optionally a pharmaceutically acceptable excipient.

19. The pharmaceutical composition according to embodiment 17 or 18, wherein the pharmaceutically acceptable excipient comprises L-methionine.

20. The pharmaceutical composition according to any of embodiments 17 to 19 further comprising at least one additional antigen from *Borrelia* or a pathogen other than *Borrelia*.

21. The pharmaceutical composition of embodiment 20, wherein the additional antigen is from a tick-borne pathogen.

22. The pharmaceutical composition of embodiment 21, wherein the tick-borne pathogen is selected from the group comprising *Borrelia hermsii, Borrelia parkeri, Borrelia duttoni, Borrelia miyamotoi, Borrelia turicatae, Rickettsia rickettsii, Rickettsia australis, Rickettsia conorii, Rickettsia helvetica, Rickettsia parkeri, Francisella tularensis, Anaplasma phagocytophilum, Ehrlichia sennetsu, Ehrlichia chaffeensis, Coxiella burnetii* and *Borrelia lonestari*, Tick-borne encephalitis virus (TBEV), Colorado tick fever virus (CTFV), Crimean-Congo hemorrhagic fever virus (CCHFV), Kyasanur forest disease virus (KFDV), Powassan virus, Heartland virus, Omsk Hemorrhagic Fever virus (OHFV) and *Babesia* spp.

23. The pharmaceutical composition of any of embodiments 20 to 22, wherein the at least one additional antigen is comprised in a second vaccine composition.

24. The pharmaceutical composition of embodiment 23, wherein the second vaccine composition is preferably a tick-borne encephalitis vaccine, a Japanese encephalitis vaccine or a Rocky Mountain spotted fever vaccine.

25. A pharmaceutical composition of any of embodiments 17 to 24, characterized in that it further comprises an immunostimulatory substance, preferably selected from the group consisting of polycationic polymers, especially polycationic peptides, immunostimulatory oligodeoxynucleotides (ODNs), especially oligo(dIdC)$_{13}$ (SEQ ID NO: 40) peptides containing at least two LysLeuLys motifs, especially peptide KLKLLLLLKLK (SEQ ID NO: 39), neuroactive compounds, especially human growth hormone, aluminium hydroxide or aluminium phosphate, Freund's complete or incomplete adjuvant, or combinations thereof.

26. The pharmaceutical composition of embodiment 25, wherein said immunostimulatory substance is a combination of either a polycationic polymer and immunostimulatory deoxynucleotides or of a peptide containing at least two LysLeuLys motifs and immunostimulatory deoxynucleotides, preferably a combination of KLKLLLLLKLK (SEQ ID NO: 39) and oligo(dIdC)$_{13}$ (SEQ TD NO: 40).

27. The pharmaceutical composition of embodiment 25, wherein said polycationic peptide is polyarginine.

28. The pharmaceutical composition of any one of embodiments 17 to 27, wherein said pharmaceutical composition is a vaccine.

29. The immunogenic polypeptide of any of embodiments 1 to 9, the nucleic acid of embodiment 10 or 11 or the pharmaceutical composition of any of embodiments 17 to 28 for use as a medicament, particularly as a vaccine.

30. The immunogenic polypeptide of any of embodiments 1 to 9, the nucleic acid of embodiment 10 or 11 or the pharmaceutical composition of any of embodiments 17 to 28 for use in a method of treating or preventing a *Borrelia* infection, particularly a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, preferably a *B. burgdorferi* s.s., *B. afzelii* or *B. garinii* infection.

31. Use of the immunogenic polypeptide of any of embodiments 1 to 9, the nucleic acid of embodiment 10 or 11 or the pharmaceutical composition of any of embodiments 17 to 28 in the manufacture of a medicament for use in a method of treating or preventing a *Borrelia* infection, wherein the infection is a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B.*

*tanukii, B. torch* or *B. sinica* infection, preferably a *B. burgdorferi* s.s., *B. afzelii* or *B. garinii* infection.

32. A method of treating or preventing a *Borrelia* infection in a subject in need thereof comprising the step of administering to the subject a therapeutically-effective amount of the immunogenic polypeptide of any of embodiments 1 to 9, the nucleic acid of embodiment 10 or 11 or the pharmaceutical composition of any of embodiments 17 to 28, or a method of immunizing a subject in need thereof comprising the step of administering to the subject a therapeutically-effective amount of the immunogenic polypeptide of any of embodiments 1 to 9, the nucleic acid of embodiment 10 or 11 or the pharmaceutical composition of any of embodiments 17 to 28.

33. A method for immunizing an animal or human against infection with a *Borrelia* organism, comprising the step of administering to said animal or human an effective amount of the immunogenic polypeptide of any of embodiments 1 to 9, the nucleic acid of embodiment 10 or 11 or the pharmaceutical composition of any of embodiments 17 to 28, wherein the effective amount is suitable to elicit an immune response in said animal or human.

34. A method for stimulating an immune response in an animal or human against a *Borrelia* organism, comprising the step of administering to said animal or human an effective amount of the immunogenic polypeptide of any of embodiments 1 to 9, the nucleic acid of embodiment 10 or 11, the vector of embodiment 12 or the pharmaceutical composition of any of embodiments 17 to 28, wherein said effective amount is suitable to stimulate the immune response in said animal or human.

35. The method according to embodiment 33 or 34, wherein the *Borrelia* organism is selected from the group comprising *B. burgdorferi* s.l., particularly *B. burgdorferi* s.s., *B. garinii*, *B. afzelii*, *B. andersoni*, *B. bavariensis*, *B. bissettii*, *B. valaisiana*, *B. lusitaniae*, *B. spielmanii*, *B. mayonii*, *B. japonica*, *B. tanukii*, *B. turdi* or *B. sinica*, preferably *B. burgdorferi* s.s., *B. afzelii* or *B. garinii*.

36. A method of designing a multivalent OspA antigen, said method comprising the steps of:
a) providing a structural scaffold comprising the amino acid sequence of an OspA protein or fragment thereof;
b) identifying potential immunogenic epitopes on the surface of said structural scaffold by in silico modelling based on the crystal structure of ST1 OspA (PDB accession 1OSP);
c) altering the surface amino acids within one or more of said potential immunogenic epitopes on said structural scaffold to match the sequence of one or more different serotypes of *Borrelia*.

The terms "comprising", "comprise" and "comprises" herein are intended by the inventors to be optionally substitutable with the terms "consisting of", "consist of" and "consists of", respectively, in every instance. The term "comprises" means "includes". Thus, unless the context requires otherwise, the word "comprises", and variations such as "comprise" and "comprising" will be understood to imply the inclusion of a stated compound or composition (e.g., nucleic acid, polypeptide, antibody) or step, or group of compounds or steps, but not to the exclusion of any other compounds, compositions, steps, or groups thereof. Similarly, the words "comprise", "contain" and "encompass" are to be interpreted inclusively rather than exclusively. The abbreviation "e.g." is derived from the Latin exempli gratia, and is used herein to indicate a non-limiting example. Thus, the abbreviation "e.g." is synonymous with the term "for example".

The invention is not limited to the particular methodology, protocols and reagents described herein because they may vary. Furthermore, the terminology used herein is for the purpose of describing particular embodiments only and is not intended to limit the scope of the present invention. As used herein and in the appended claims, the singular forms "a", "an", and "the" include plural reference unless the context clearly dictates otherwise.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The present invention is further illustrated by the following Figures, Tables, Examples and the Sequence listing, from which further features, embodiments and advantages may be taken. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

FIGURES

FIG. 1 (A) Schematic representation of the partitioning of the molecular surface in multivalent OspA antigens of the invention, here modelled in the context of the crystal structure of the C-terminal region (domain) of serotype 1 (PDB accession 1OSP). Taking advantage of the high fold conservation among OspA serotypes 1-6, all Variants (Variants 1-6) in the study were constructed using the C-terminal region of *B. afzelii* OspA ST2 as a structural scaffold (aa 126-273, SEQ ID NO: 7). Surface modifications followed a scheme with two different layouts ("Layout 1" and "Layout 2") of surface partitioning defining areas (a.k.a. "patches") which were each modified to present surface residues of the respective serotype. Layout 1 comprises patches A, B, C, D and E, which in serotype 1 OspA contain binding sites (i.e., epitopes or partial epitopes) of monoclonal antibodies LA-2 (patch A), 336 (patch B), 105.5 (patch C), essential residues of the epitope for monoclonal antibody 4C10C2 as well as a linear epitope [LE] based on binding of antibodies from patient sera (patch D) and a combination of the monoclonal antibody C11178 binding site and the tick gut binding domain (TGBD) of OspA (patch E). Layout 2 comprises patches A, F, G and H, which are based on the corresponding serotype 1 OspA binding residues of LA-2 (patch A), an extended form of the binding region for mAb 336 (patch F, an extended version of patch B from Layout 1), LE as parts of the binding regions of mAbs 105.5 and 4C10C2 (patch G) and an extended form of the TGBD (patch H, an extended version of patch E of Layout 1). (B) Variants 1-4 are based on Layout 2. On the surface of patch A, residues were mutated to represent ST1, and on patch F to represent ST5 in all four Variants. Patch G was populated with surface residues of ST5 in Variants 1 and 2 and with surface residues for ST4 in Variants 3 and 4. Patch H was populated with surface residues of ST4 in Variants 1 and 2 and ST5 in Variants 3 and 4. Variants 1 and 4 were stabilized by the introduction of an "alpha-type" disulfide bond; i.e., amino acids 244 and 259 were replaced with cysteine residues. Variants 2 and 3 were stabilized by the introduction of a "beta-type" disulfide bond; i.e., amino acids 182 and 269 were replaced with cysteine residues. Variants 5 and 6 are based on Layout 1. Patch A was populated with surface residues of *B. garinii* OspA ST6 in Variant 5 and *B. afzelii* OspA ST2 in Variant 6. Patches B, C, D and E were populated with surface residues for *B. garinii* OspA ST3, *B. afzelii* OspA ST2 and *B. garinii* OspA ST6 residues, respectively. Variants 5 and 6 were stabilized by the introduction of a "beta-type" disulfide bond.

FIG. 2 Sequence alignment comparing multivalent OspA antigen Variants 1 to 6 to the sequence of the *B. afzelii* OspA C-terminal fragment scaffold (OspA ST2, aa 126-273, SEQ ID NO: 7, *B. afzelii* strain K78, AJY72832.1) showing the modified amino acid residues (BLASTP). The dots represent conserved amino acids that were unchanged. The relative location of amino acids in the three-dimensional structure is shown in the line labelled "Exposure". Surface exposed amino acids "+", partially exposed "o", and buried "–". The location of the residues making up patches A-H of the two layouts is provided in the lines labelled "Layout 1" and "Layout 2". The location of the introduced cysteine residues are shown in the lines labelled "Type alpha" and "Type beta". Also provided is the amino acid sequence of the ST1 OspA fragment, the three dimensional structure of which was used as a reference.

FIG. 3 (A) Linear schematic representation of the lipidated multivalent OspA fusion antigen Lip-V3-L2-V5 of the invention. The V3-L2-V5 polypeptide comprises a fusion of Variants 3 (V3; SEQ ID NO: 10) and 5 (V5; SEQ ID NO: 12) linked together with a 23 amino acid linker sequence (L2; SEQ ID NO: 32) derived from a loop region of protein P66 from *B. garinii* strain PBr. The multivalent OspA antigen also comprises an N-terminal lipidation signal sequence from the *E. coli* major outer membrane lipoprotein to facilitate lipidation of the N-terminus (indicated as the post-processed "Lip-CSS") and an optional C-terminal histidine tag (6H) for purification purposes. Shown are patches A-H as depicted in FIGS. 1 and 2. Placement of the introduced stabilizing cysteine bonds in Variants 3 and 5 is also shown schematically. (B) Sequence alignment of Variants 3 and 5 with the ST2 structural scaffold sequence of the *B. afzelii* K78 OspA C-terminal domain (aa 126-273 from AJY72832.1, SEQ ID NO: 7) showing the modified amino acid residues (BLASTP). The position of the patches and introduced cysteines are shown as described in FIG. 2. Additionally, the sequence of linker L2, derived from a loop region of P66 from *B. garinii* strain PBr, is included (SEQ ID NO: 18).

FIG. 4 Measurement of the antibody response to lipidated multivalent vaccine candidates by ELISA. The immunogenicity of individual multivalent proteins V1-V6 when administered three times at two week intervals at a dose of 5 µg and formulated with 0.15% aluminium hydroxide was assessed. Immune sera collected from mice two weeks after the final immunization were serially diluted and tested in duplicate. The plates were coated with C-terminal fragments of the respective OspA ST and the immune response to the multivalent OspA candidates was compared to the response to FL-OspA of the respective serotypes. The results are presented as half-max geometric mean titres (GMT) with a 95% confidence interval and the dotted lines represent the detection limit.

Figure 5:
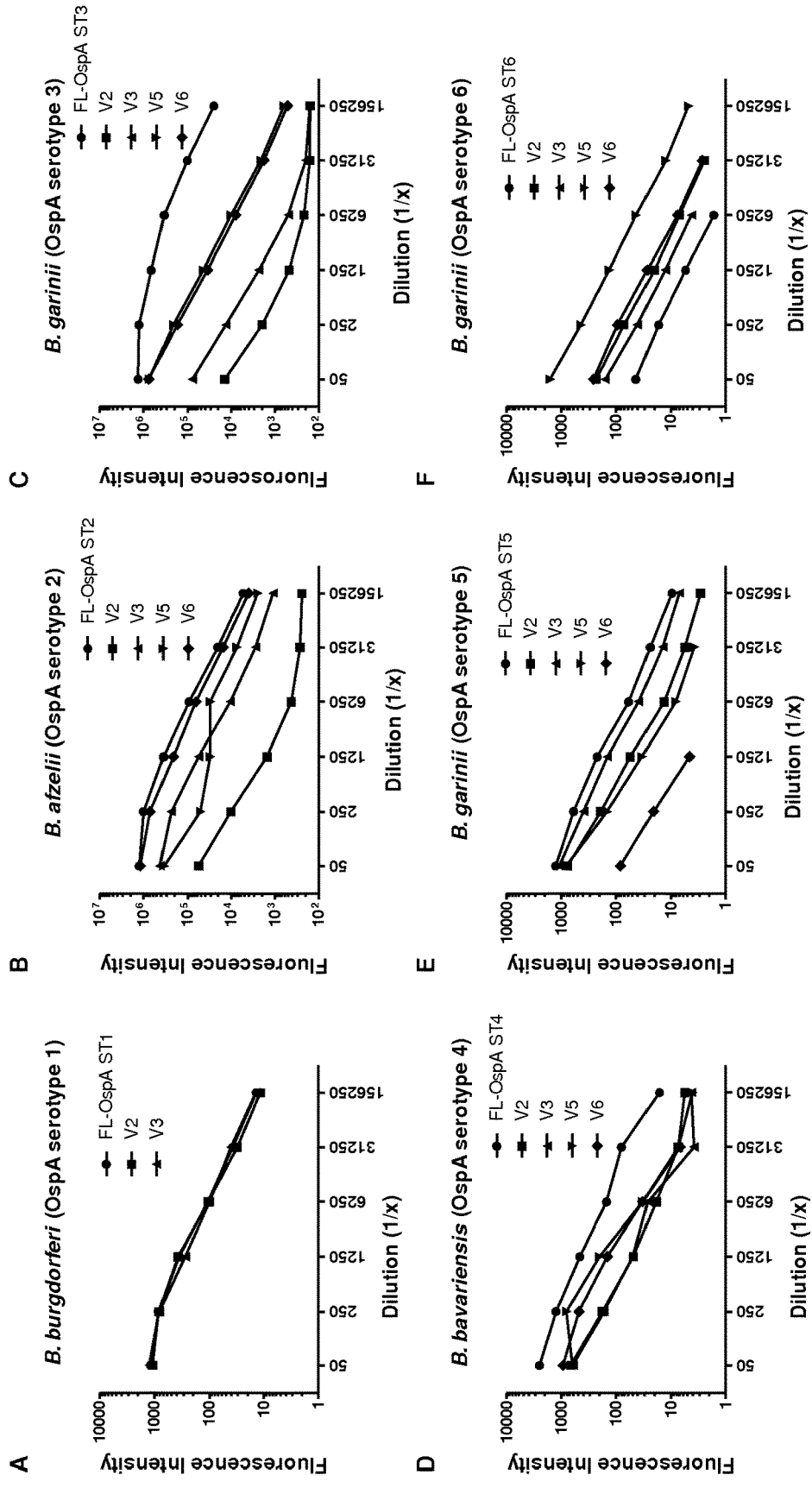

FIG. 5 *Borrelia* surface binding studies to determine vaccine induced functional antibodies. The functionality of the antibodies generated by vaccination with the lipidated multivalent vaccine candidates V2, V3, V5 and V6, as outlined in FIG. 4 above, was tested in a *Borrelia* surface binding assay. The binding of vaccine induced antibodies to OspA of the corresponding serotype was compared to the antibodies generated by the respective FL-OspA. The surface binding assay was performed with *B. burgdorferi* OspA ST1 ZS7, *B. afzelii* OspA ST2 Pra10, *B. bavariensis* OspA ST4 Win, *B. garinii* OspA ST5 PHei, and OspA ST6 KL11. The results are presented as fluorescence intensity.

Figure 6:
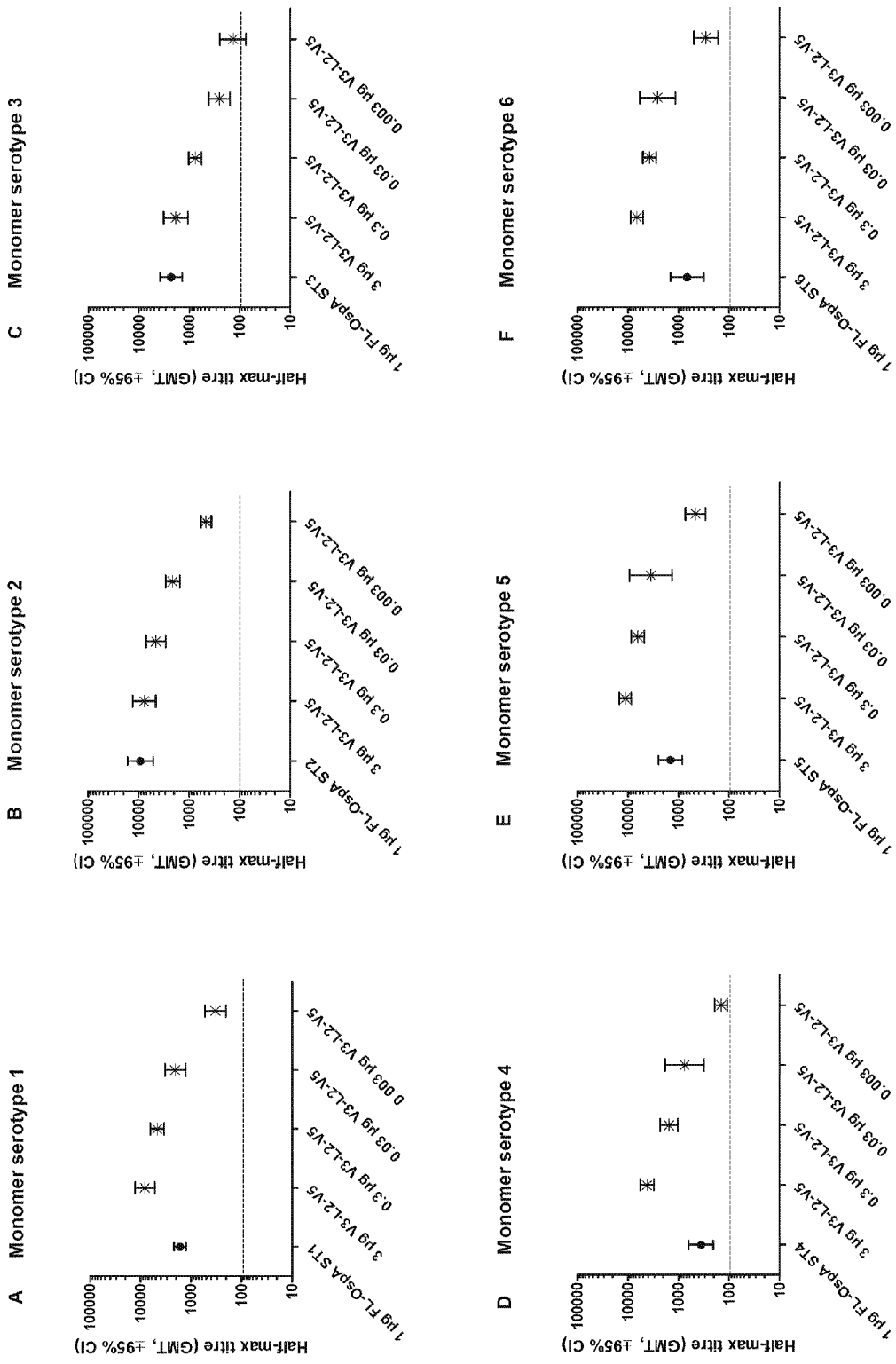

FIG. 6 Serotype-specific antibody responses to the lipidated multivalent fusion antigen Lip-V3-L2-V5 were compared with responses to full-length lipidated OspA proteins from serotypes 1-6 (FL-OspA ST1-6). Groups of 5-8 week old female C3H/HeNRj mice were immunized subcutaneously with V3-L2-V5 (SEQ ID NO: 26; 3 µg; 0.3 µg; 0.03 µg and 0.003 µg) or with individual full-length OspA proteins (SEQ ID NOs: 1-6; 1 µg) three times at two week intervals. All antigens were formulated with 0.15% aluminium hydroxide Immune sera were collected one week after the final immunization for quantification of anti-OspA IgG antibodies by ELISA. Truncated C-terminal OspA proteins of the respective serotypes were used as coating antigens (monomer serotypes 1-6; SEQ ID NOs: 33-38). Immunization with V3-L2-V5 elicited higher antibody titers than immunization with FL-OspA ST1 (A), ST4 (D), ST5 (E) or ST6 (F) and equivalent antibody titers when compared with FL-OspA ST2 (B) and FL-OspA ST3 (C) in the highest immunization dose of 3 µg. Antibody titers elicited by V3-L2-V5 decreased dose-dependently.

Figure 7:
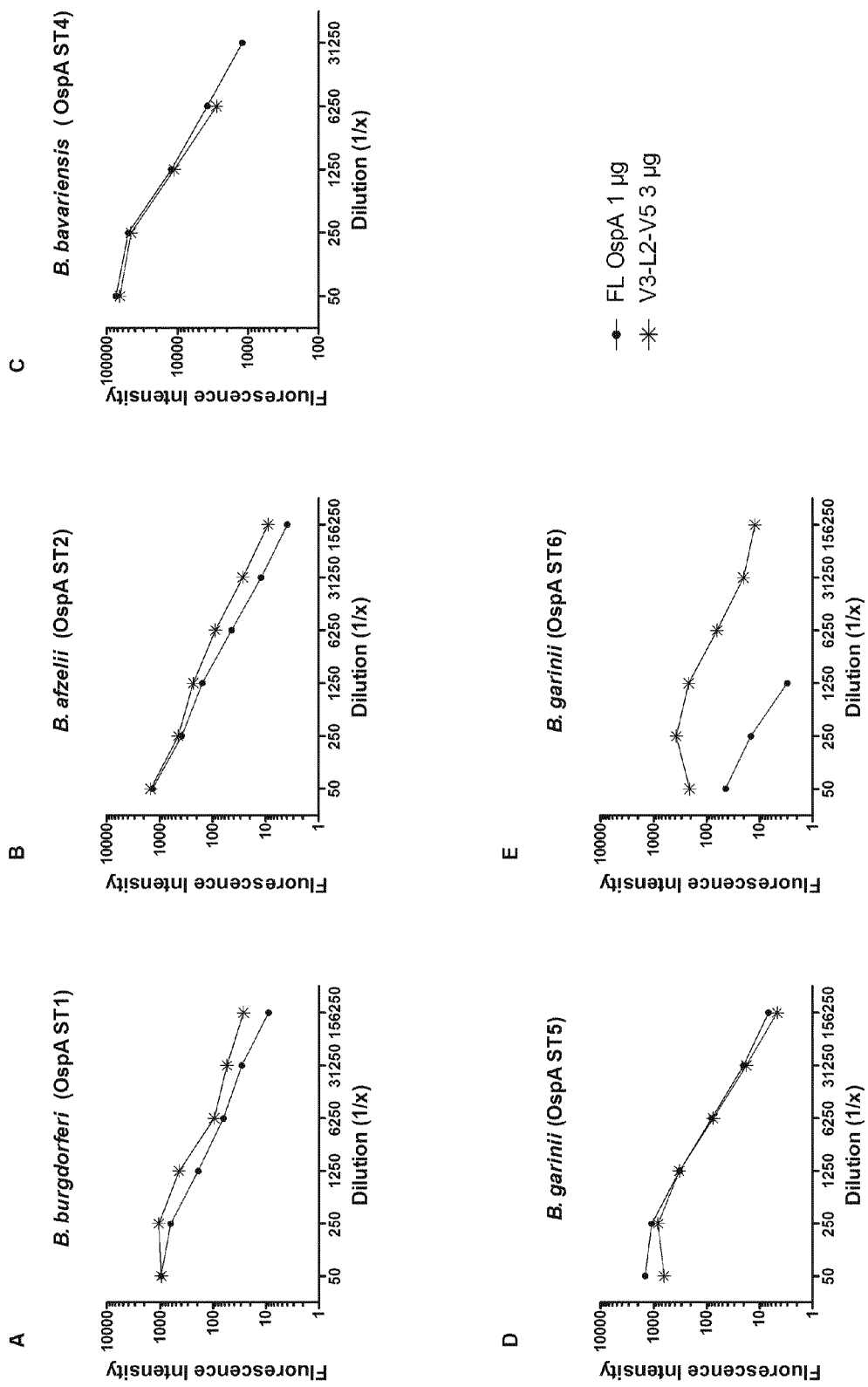

FIG. 7 Comparison of functional antibodies elicited by immunization with the lipidated multivalent fusion antigen Lip-V3-L2-V5 versus full-length lipidated OspA proteins of five different serotypes in mice. The ability of V3-L2-V5 to generate functional antibodies was assessed by a *Borrelia* surface binding assay. For these in vitro assays, sera from mice immunized three times with the highest dose of V3-L2-V5 (3 µg) were used for comparison with sera from mice immunized three times with 1 µg of the full-length OspA of the respective serotypes Immunization with V3-L2-V5 generated comparable surface binding to spirochetes expressing OspA of ST1 (A), ST2 (B), ST4 (C) and ST5 (D) as compared with the corresponding FL OspA proteins. The surface binding of V3-L2-V5 serum antibodies to spirochetes expressing OspA of ST6 (E) was higher than the binding of the FL-OspA ST6 (E) serum antibodies.

Figure 8:
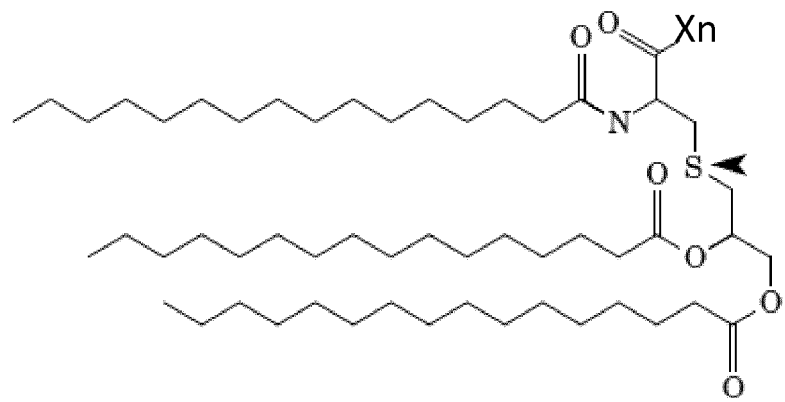

FIG. 8 The chemical structure of Pam3Cys, an example of a fatty acid substituted cysteine, such as would be found at the N-terminus of lipidated polypeptides of the current invention.

Figure 9:
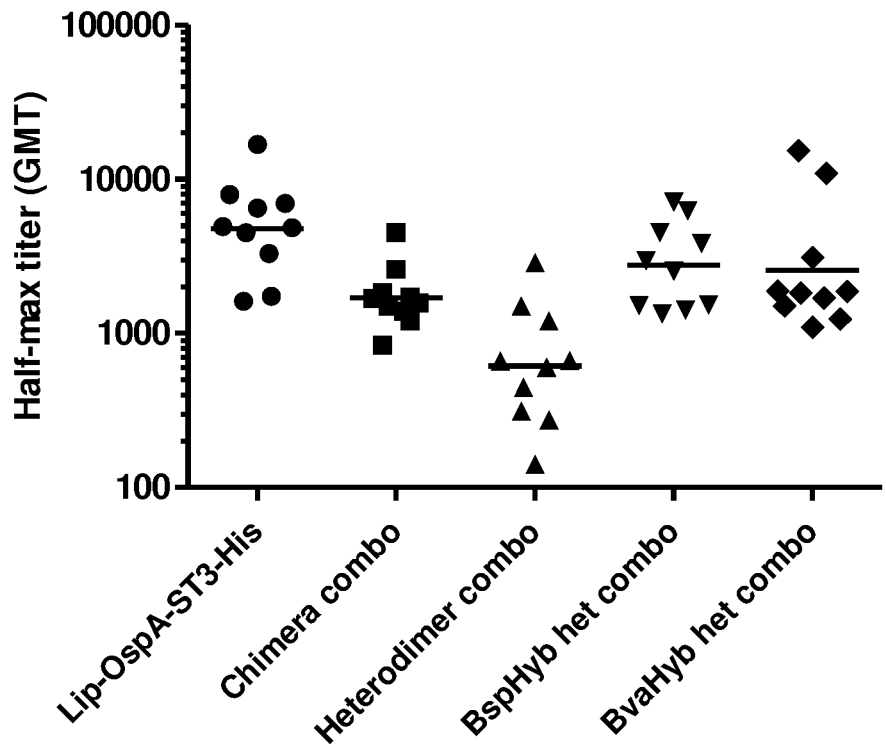

FIG. 9 Antibody titers generated to serotype 3 OspA protein following immunization with multivalent OspA vaccines (see also Table 5). Mice were immunized three times at two week intervals with full-length His-tagged ST3 OspA (1 µg/dose of Lip-OspA-ST3-His; SEQ ID NO: 3); with the Chimera combination vaccine ("Chimera combo": 1 µg/dose each of Lip-Chimeric OspA ST1/ST2-His, Lip-Chimeric OspA ST5/ST3-His and Lip-Chimeric OspA ST6/ST4-His); with the Heterodimer combination vaccine ("Heterodimer combo"; 1 µg/dose each of Lip-S1D1-S2D1, Lip-S4D1-S3D1 and Lip-S5D1-S6D1); with the BspHyb heterodimer combination vaccine ("BspHyb het combo"; 1 µg/dose each of Lip-S1D1-S2D1, Lip-S4D1-S3BspHybD1 and Lip-S5D1-S6D1) or with the BvaHyb heterodimer combination vaccine ("BvaHyb het combo"; 1 µg/dose each of Lip-SID1-S2D1, Lip-S4DI-S3BvaHybD1 and Lip-S5D1-S6D1). All immunogens were formulated with 0.15% aluminium hydroxide. Sera were collected one week after the last dose. Titers of IgG antibodies to full-length ST3 protein were determined by ELISA.

Figure 10:
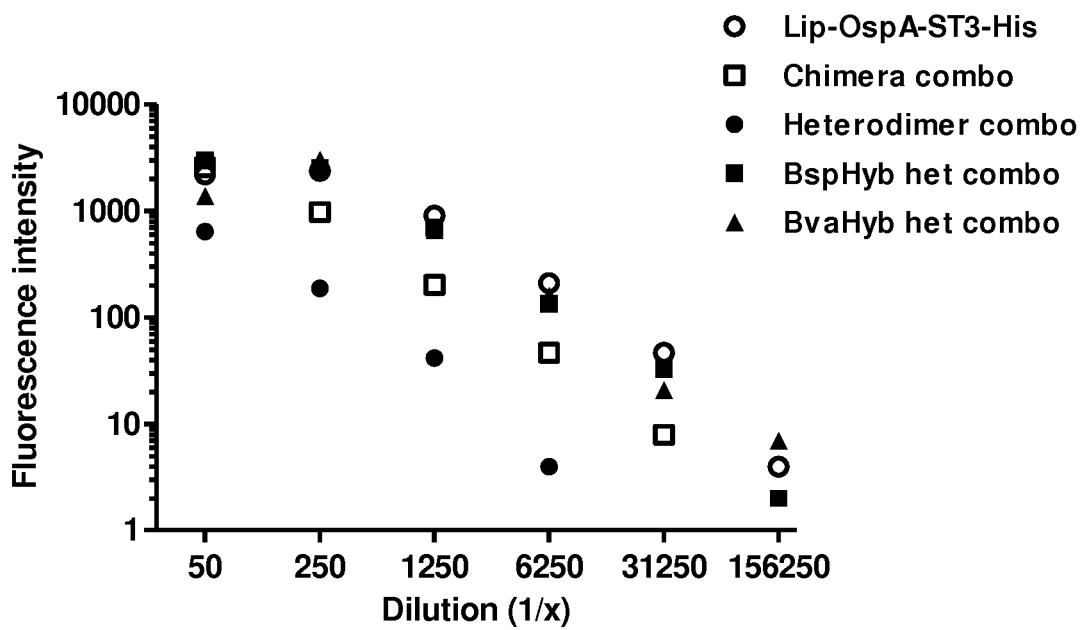

FIG. 10 Functionality of antibodies from mice immunized with multivalent OspA vaccines as measured by cell surface binding. Mice were immunized as in FIG. 9 above (see also Table 5) and sera were collected and pooled at one week after the last dose. Serial dilutions of the sera were tested for in vitro binding to Borrelia via cell staining followed by flow cytometry. Fluorescence intensity values measured following staining with sera collected from control mice immunized with Al(OH)$_3$ adjuvant alone were subtracted to account for non-specific binding. Spirochetes used in the binding assay were B. garinii, OspA serotype 3, strain Fr.

EXAMPLES

Materials and Methods

Ethics statement: The animal experiments in the study were conducted in compliance with Austrian law (Tierversuchsgesetz 2012, BGB1. I Nr. 114/2012) and approved by 'Magistratsabteilung 58'. Furthermore, in accordance with the 3R principle, the number of animals used in the study was curtailed.

Design of chimeric constructs. The protein surface of OspA ST1 (crystal structure (PDB 1OSP) (Li et al., PNAS, 1997. 94(8):3584-9) was analyzed and the residues classified into surface accessible, partially accessible and buried (FIG. 2). Surface areas were defined in analogy to known epitopes to best represent potential binding sites (from ST1, FIG. 1). Homology models of the C-terminal domain (ST1-6, modified by disulfide-bond "beta") were relaxed in short molecular mechanics simulations (Gromacs/OPLS-AA) to verify structural integrity (Open-source PyMol, http://sourceforge.net/projects/pymol/, DeLano, W. L., The PyMOL Molecular Graphics System, DeLano Scientific, San Carlos, CA, USA. Available: http://www.pymol.org. 2002; Kiefer, F., et al., The SWISS-MODEL Repository and associated resources. Nucleic Acids Res, 2009. 37(Database issue): p. D387-92.; Hess, B., et al., GROMACS 4: Algorithms for Highly Efficient, Load-Balanced, and Scalable Molecular Simulation. J Chem Theory Comput, 2008. 4(3): p. 435-47; Kaminski, G. A., et al., Evaluation and Reparametrization of the OPLS-AA Force Field for Proteins via Comparison with Accurate Quantum Chemical Calculations on Peptides. The Journal of Physical Chemistry B, 2001. 105(28): p. 6474-648743). All models showed high fold conservation was observed which is a prerequisite to be able to choose the ST2 C-terminal fragment of B. afzelii OspA ST2, consisting of amino acids 126-273 (SEQ ID NO: 7) as a structural scaffold for the surface shaping approach. The serotypes on the patches (potential antibody binding sites; i.e., epitopes) were assigned by replacing exposed residues belonging to the targeted patch to the respective serotype (e.g. FIG. 1B).

Many combinations of layouts, and patch attribution combinations are possible. Preferably the interference of near residues on an adjacent patch mismatching the actual assignment of a patch is low. Programmatically, a score was determined by calculating the residue distance (as defined by the $C_{alpha}$-$C_{alpha}$ distance) of interfering residues. Penalty contributions for each non-ST2 residue in a patch were scaled with the distance of interfering residues (0.5 nm plus 0.3 nm switching region) and by their position in the three dimensional structure; i.e. buried, partially exposed or exposed, the amino acid residues were given a factor of 0, 0.5 and 1, respectively and summed up. This is repeated for each patch in a given layout to give a score for one combination. Scoring is repeated for each possible combination and used for a ranking of possible patch population to facilitate the choice. Finally, the surface exposed amino acid residues for a chosen combination patch layout and assignments were substituted represent the OspA serotypes of choice within the single patches of the candidate Variant.

Molecular Cloning: The OspA amino acid sequences used for designing the chimeric vaccines were derived from B. burgdorferi serotype 1 (aa 126-273, strain B31, NP_045688.1), B. afzelii serotype 2 (aa 126-273, strain K78, AJY72832.1), B. garinii serotype 3 (aa 126-274, strain PBr, YP_002476925.1), B. bavariensis serotype 4 (aa 126-273, strain PBi, YP_063283.1), B. garinii serotype 5 (aa 126-273, strain PHei, CAA56544.1) and B. garinii serotype 6 (aa 126-274, strain DK29, CAA45010). The sequence alignment of the multivalent Variants as compared to the C-terminal domain of B. afzelii OspA ST2 (structural scaffold) is shown, with identical amino acids depicted as dots and substituted amino acids indicated (FIG. 2). The nucleotide sequence of each of the hybrid constructs was codon optimized and synthesized (Eurofins Scientific and GeneArt Gene Synthesis, Thermo Fisher Scientific). The constructs were digested with HindIII and XhoI and cloned into the expression vector pET28b(+) (Merck Millipore, USA) with an inclusion of an N-terminal 23 amino acid signal sequence for lipidation (MKATKLVLGAVILGSTLLAGCSS; SEQ ID NO: 30) from E. coli major outer membrane lipoprotein and a C-terminal histidine tag (6×1-1). Two chimeric Variants, Variant 3 and Variant 5, were fused together with a 23 amino acid linker sequence (L2; ANNQAGQKSSGSTQAT-TPNLTFE; SEQ ID NO: 32) to form the multivalent OspA heterodimer denoted as V3-L2-V5. The linker sequence was derived from a loop region of P66 (a major Borrelia porin) from B. garinii strain PBr (EED29356.1). For the generation of the final multivalent fusion vaccine (V3-L2-V5), Variant 3 was inserted (immediately after the lipidation signal sequence) into the pET28b (+) vector using the HindIII and SpeI restriction sites, followed by the linker sequence using SpeI and ScaI restriction sites and finally inserting Variant 5 using the ScaI and XhoI restriction sites.

Protein expression and purification: Protein expression and purification up to the step of phase separation with Triton X-114 was performed as described by Comstedt and coworkers (Comstedt et al., 2015, Vaccine, 33(44):5982-8). Briefly, induction of protein expression was performed at 25° C. with 0.1 mM IPTG. A protease Inhibitor Cocktail II (PIC II: 2 mL Bestatin+2 mL AEBSF+2 mL E-64) was added to the lysis buffer (50 mM Tris-HCl; 500 mM NaCl; 5 mM EDTA at pH 8.0) and cell lysis was carried out with a high pressure homogenizer (PANDA 2K). Triton X-114 was added to the crude lysate (at 0.06 times the volume of crude lysate) and the solution was incubated at 4° C. under gentle stirring overnight and then centrifuged at 7000×g for 1 hour at 4° C. The supernatant was incubated at 28° C. for 30 minutes. The lipid phase was recovered by centrifugation at 7000×g for 40 minutes at 28° C. The His-tagged chimeric proteins were purified by Immobilized Metal Ion Affinity Chromatography (IMAC). Briefly, the lipid phase was diluted 1:20 in lipid phase dilution buffer (50 mM Tris-HCl (pH 8); 500 mM NaCl; 0.05% Tween 20; 10% Ethanol) and loaded onto a column with $Ni^{2+}$-Sepharose beads (GE Healthcare; Ni Sepharose™ 6 Fast Flow) equilibrated with lipid phase dilution buffer. The bound His-tagged proteins were eluted with an imidazole elution buffer (50 mM Tris-HCl; 500 mM NaCl; 0.05% Tween-20; 100 mM Imidazole) with increasing imidazole concentrations (100 mM, 250 mM and 500 mM). The PyroGene™ Recombinant Factor-C Kit (Lonza) was used to determine the concentration of endotoxin in the purified lipidated chimeric proteins.

Immunization and challenge: The immunization and challenge studies were performed as described by Comstedt and coworkers (Comstedt et al., 2014, Plos One 9(11):e113294; Comstedt et al., 2015, Vaccine, 33(44):5982-8). The purified lipidated chimeric proteins were formulated with 0.15% aluminium hydroxide (Alhydrogel, Brenntag) as an adjuvant. Groups of 10 female C3H/HeNRj mice per antigen were immunized sub-cutaneously with 5 μg of individual vaccine candidates. 5 μg of full-length OspA protein was used as a positive control and the placebo group was injected with adjuvant alone. Three immunizations were performed at two week intervals and immune sera were collected at day 7 after the final immunization. Two weeks following the final immunization, mice were challenged with Borrelia by either subcutaneous injection or tick challenge. For challenge with B. burgdorferi (ST1) and B. garinii (ST5 and ST6), in vitro grown spirochetes expressing OspA (Comstedt et al., 2014, Plos One, supra; Comstedt et al., 2015, Vaccine, supra) were delivered subcutaneously at a dose of $5 \times 10^4$ spirochetes in 100 μL per mouse. OspA expression was confirmed by flow cytometry and only cultures with at least 80% of the spirochetes expressing OspA on their surface were used for challenge.

Ticks infected with B. afzelii (strain IS1), B. burgdorferi (strains Pra1) and B. bavariensis (strain Marx1) were used to challenge mice as described elsewhere (Comstedt et al., 2014, Plos One, supra). For the IS1 and Marx1 strains, two ticks and for the Pra1 strain, three ticks were applied on each mouse. Mice with at least one (IS1 and Marx1) or two (Pra1) fully-fed tick(s) were included in the subsequent read outs. Mice were anesthetized with isoflurane prior to terminal bleeding and sacrificed by cervical dislocation. The urinary bladder and both ears were collected from each mouse. The infectious status of individual mice was determined by VIsE ELISA and qPCR (for selected experiments) as described below.

OspA ELISA: Immune sera derived from mice after the third immunization were analyzed for specific IgG titers. Indirect ELISA was performed using the truncated OspA protein of respective serotypes as the coating antigen. The ELISA was performed as previously described (Comstedt et al., 2014, Plos One, supra). Briefly, 96-well plates were coated with 0.05 μg of protein in 50 μL PBS per well overnight at 4° C. The plates were blocked with 100 μL per well with blocking buffer (PBS with 0.05% Tween-20 [PBST]) for one hour at room temperature. Serum samples were serially diluted and tested in duplicate by incubating for one hour at room temperature after addition to the prepared plates. An HRP-conjugated polyclonal rabbit anti-mouse IgG (DAKO) was used as secondary antibody, ABTS (2,2'-azino-bis(3-ethylbenzothiazoline-6-sulphonic acid)) was used as substrate and the reaction was stopped with SDS. Absorbance was read at 405 nm. Antibody titers are presented as half-max titers, which represents the reciprocal of the serum dilution corresponding to the mean absorbance between the highest and the lowest dilution.

Surface staining of Borrelia: Spirochetes were stained to determine OspA expression as described previously (Comstedt et al., 2014, Plos One, supra). Briefly, spirochetes were fixed by the addition of an equal volume of 4% paraformaldehyde. Heat-inactivated serum pools were serially diluted (1:5) in washing buffer in a separate dilution plate. Diluted sera were added to the fixed spirochetes and incubated for 45 minutes at RT. PE-conjugated goat anti-mouse IgG (Beckman Coulter, USA) was used as secondary antibody and LDS 751 (Life Technologies, USA) was used to stain the DNA of the spirochetes. The stained spirochetes were analyzed with a flow cytometer (FC 500 Cytomics, Beckman Coulter) by gating for positive LDS 751 events.

Growth Inhibition of Borrelia: A growth inhibition assay was used as a functional assay for serum antibodies (Comstedt et al., Plos One, 2014, supra). The heat inactivated immune serum pools were serially diluted (1:5) and incubated with spirochetes (1.0E+03 to 1.0E+04/well) and 1% guinea pig complement in 96-well plates for 3-5 days at 35° C. with 5% $CO_2$. Surviving spirochetes were stained with LDS 751 (Life Technologies). The amount of surviving spirochetes was determined by flow cytometry (FC 500 Cytomics, Beckman Coulter). The values are represented as growth inhibition titer which is defined as the reciprocal of the serum dilution with at least 50% reduction in growth.

VIsE ELISA: The ELISA with the invariable region 6 (IR6) of the variable major protein like sequence E protein (VIsE) was performed as described before (Comstedt et al., 2014, Plos One, supra and WO14/006226). Briefly, 96-well streptavidin pre-coated plates were coated with the 25 amino acid long biotinylated IR6 peptide (MKKDDQIAAAMVLRGMAKDGQFALK). Sera were diluted (1:2) and tested in duplicate, using HRP-conjugated polyclonal rabbit anti-mouse IgG (DAKO) as a secondary antibody. ABTS was added as a substrate and the reaction was continued for 30 minutes. Absorbance was read at 450 nm.

Quantitative PCR: Detection of spirochete DNA was done by PCR amplification of a part of the recA gene as described previously (Comstedt et al., Plos One 2014, supra and WO14/006226; forward primer: CATGCTCTT-GATCCTGTTTA, reverse primer: CCCATTTCTCCATC-TATCTC). DNA from bladders was isolated using the DNeasy Blood and Tissue Kit from Qiagen (Germany) according to manufacturer's instructions. The recA gene fragment from B. burgdorferi strain N40 was serially diluted and used as standard in each reaction.

Statistics: The infection status of the mice was based on VIsE ELISA and quantitative PCR as described above. All groups were compared with a placebo group for assessment of infection/protection and statistical significance was calculated with Fisher's exact test (two-tailed), *$p<0.05$, $p<0.01$ and * $p<0.001$, ns=not significant.

Example 1. Design of Chimeric Vaccines Representing Multiple OspA Serotypes on their Surface and Expressed as Single Proteins The chimeric OspA Variants disclosed herein were designed with the aim of presenting multiple OspA serotypes on a single polypeptide antigen, thereby reducing the number of proteins required to achieve broad protection against the major pathogenic Borrelia species. The surface shaping approach presented in this study uses as a structural scaffold the truncated and disulfide-bridge stabilized C-terminal domain of OspA from B. afzelii OspA ST2 (aa 126-273; SEQ TD NO: 7). The surface-exposed region of this C-terminal domain was divided into eight overlapping areas referred to as Patch A-Patch H (FIGS. 1A and B) based on known sites of binding of monoclonal antibodies to B. burgdorferi OspA (ST1). A patch as defined herein is an area on the molecule, whether continuous or discontinuous in the primary amino acid sequence, which can harbor a potential structural epitope; i.e. a site large enough to fulfill the requirements that an antibody can bind. Surface-exposed amino acid residues can then be replaced to represent the targeted surface within a patch.

In the given examples, patch A is based on the binding of the LA-2 monoclonal antibody (Ding et al., 2000, J Mol Biol, 302(5):1153-64); Patch B is based on the binding site of mAb 336 (Koide, S., et al., 2005, J Mol Biol, 350(2): 290-9); Patch C is based on the binding region of mAb 105.5 (Koide et al., supra); Patch D represents portions of the binding site of mAb 4C10C2 (Legros et al., 2000, Protein Sci, 9(5):1002-10) and parts of the linear epitope (LE) (Schubach et al., 1991, Infect Immun, 59(6):1911-5); Patch F represents an extended version of Patch B and includes the 336 epitope and parts of the 105.5 epitope; Patch G represents parts of the binding sites of mAb 105.5, mAb 4C10C2 and a linear epitope (LE) identified from patient serum samples (Schubach, et al., supra); Patch E is based on the binding regions of mAb CIII78 (Sears et al., 1991, J. Immunol., 147(6):1995-2000) and the tick gut binding domain (TGBD) (Pal et al., 2000, J. Clin. Invest., 106(4): 561-9); Patch H represents an extended version of patch E and includes a mouse T-cell epitope from OspA named B4 (Zhong et al. 1996, Eur. J. Immunol., 26(11): 2749-57). Patches A, B and C are defined as the analog surface areas which contain known binding sites of monoclonal antibodies to ST1 OspA. Furthermore, Patches D-H take advantage of less precisely-defined binding regions of mAbs and include additional epitopes (e.g., TGBD, LE and B4).

The surface exposed amino acid residues on the patches described above were replaced with residues of three out of the six major OspA serotypes (OspA ST1-ST6) in order to accommodate multiple serotypes on one protein molecule. Six chimeras, referred to as Variant 1-Variant 6, were constructed and centered on Patch A-Patch H (FIG. 1). The design of Variants 1-4 was centered on Patch A, F, G and H (Layout 2) and amino acid residues of OspA ST1, ST4 and ST5 were represented on the surface (FIG. 1B). Variants 1 and 4 were stabilized by introducing an a-type disulfide bond (i.e., disulfide bond between two introduced cysteine residues at amino acid positions corresponding to amino acids 244 and 259 of OspA serotype 2) whereas Variants 2 and 3 were stabilized by introducing a β-type disulfide bond (i.e., disulfide bond between two introduced cysteine residues at amino acid positions corresponding to amino acids 182 and 269 of OspA serotype 2) (Comstedt et al., 2014, PLoS One 9(11):e113294) in order to study the effect of different positioning of disulfide bonds on immunogenicity and efficacy of the multivalent chimeras. The difference in Variants 1-4 is represented with serotype interchanges on Patch G and H as indicated in FIG. 1B with the aim to study the difference in immunogenicity as well as efficacy of this set of chimeric candidates with respect to OspA ST4 and ST5. The design of Variants 5 and 6 is based on Patches A, B, C, D and E (i.e., Layout 1; FIG. 1A) and OspA ST2, ST3 and ST6 are represented on the surface (FIG. 1B). Variants 5 and 6 were stabilized by an introduced β-type disulfide bond. The difference in these two Variants is represented by a serotype switch on Patch A as illustrated in FIG. 1B, to determine the effect of this difference in immune response and protection generated against OspA ST2 and OspA ST6.

The design of the chimeric Variants with the surface shaping approach takes into account important protective epitopes described in the literature as defined by respective monoclonal antibodies (LA-2, CIII78, 336 and 105.5) and represents the amino acid residues of prevalent OspA serotypes on the surface. As an example, in Variants 1-4, Patch A is populated with residues from OspA ST1 (prevalent in the U.S.) and in Variants 5 and 6, with residues from OspA ST2 and ST6 (prevalent in Europe). Furthermore, assigning different serotypes to different patches in these two sets of multivalent chimeras also allows identification of potential immunogenic and protective epitopes with respect to serotypes other than OspA ST1. Overall, the use of a surface shaping approach in this study enabled the expression of multiple serotypes (as patches) on the surface of a single antigen, subsequently resulting in fewer number of antigens in the final vaccine formulation. FIG. 2 shows a sequence alignment of the multivalent OspA Variant 1-Variant 6 as compared to the conserved backbone of a *B. afzelii* K78 OspA C-terminal domain which defines the unmodified scaffold.

Example 2. Multivalent Vaccine Candidates Induce Significant Antibody Titers Against all Major OspA Serotypes OspA based vaccines are thought to protect primarily via production of circulating antibodies that are ingested by the ticks during the blood meal. In the mid-gut of the tick, these antibodies bind and neutralize the spirochetes thereby preventing pathogen transmission and subsequent infection. In this regard the generation of high titers of antibodies following immunization is of primary importance. We therefore assessed the antibody response generated by the chimeric Variants against the six major clinically relevant OspA serotypes (ST1-ST6) with ELISA. All immunizations in this study were performed with the antigens formulated with 0.15% of aluminum hydroxide. Groups of 5-8 week-old female C3H/HeNRj mice were immunized three times at two week intervals with a dose of 5 μg of individual vaccine candidates (Variant 1-Variant 6).

Since the multivalent Variants represent only the C-terminal half of OspA, the OspA ELISA plates were coated with truncated and stabilized C-terminal monomers (ST1-ST6; SEQ ID Nos: 33-38) and the immune response was compared with the response to immunization with full-length OspA of the respective serotypes (FL-OspA ST1-ST6; SEQ ID Nos: 1-6, respectively).

As shown in FIG. 4, Variant 1 with the alpha-type disulfide bond induced a significantly lower antibody response as compared to Variants 2, 3 and 4 with respect to OspA ST1 ELISA titers; however, the immunogenicity was comparable with respect to other serotypes. Variant 4, also with an alpha-type disulfide bond, induced a comparable immune response to Variants 1, 2 and 3 with respect to all serotypes included on the patches. Variants 2 and 3 induced comparable antibody titers with respect to FL-OspA ST1, FL-OspA ST4 and FL-OspA ST5 (homologous serotypes represented on their surface) and cross-reactive antibodies comparable to FL-OspA ST6, respectively. However, the immune response was lower when compared to FL-OspA ST2 and ST3. Variants 5 and 6 induced comparable titers to FL-OspA ST2, FL-OspA ST3, and FL-OspA ST6 (serotypes presented on their surface), as well as cross reactive antibodies comparable to FL-OspA ST4. However, these candidates induced a lower immune response compared with FL-OspA ST1 and FL-OspA ST5, respectively.

The results demonstrated that the immune response of the multivalent Variants varied according to distribution of serotypes on different patches represented on the surface.

Example 3. Generation of Functional Antibodies by Multivalent OspA Vaccine Candidates The multivalent Variants V2, V3, V5 and V6 were further evaluated for their ability to induce functional antibodies against the major clinically relevant OspA serotypes (ST1-

ST6). The functional assessment was based on the ability of the antibodies to bind in vitro to *Borrelia* expressing OspA ST1-ST6 on their surface as well as by testing the ability of antibodies to inhibit the growth of live spirochetes in vitro. Heat inactivated pooled serum samples from mice immunized with each Variant were tested in five-fold serial dilutions for their ability to bind to spirochetes expressing OspA of the respective serotypes. Variants 1 and 4, stabilized with disulfide bond alpha, induced very low surface binding with respect to OspA ST1, ST2, ST4, ST5 and ST6 (data not shown). As shown in FIG. 5, Variant 2, with disulfide bond beta, generated equivalent binding with respect to FL-OspA ST1 but lower binding was observed when compared with FL-OspA ST2, FL-OspA ST4 and FL-OspA ST5. Variant 3, with disulfide bond beta, induced comparable surface binding when compared with FL-OspA ST1 and FL-OspA 5 but lower surface binding was observed when compared with FL-OspA ST2 and FL-OspA 4. Variants 2 and 3 both generated strong binding when compared with FL-OspA ST6 (which in general induces low binding). Variant 5 and Variant 6, with disulfide bond beta, demonstrated surface binding similar to FL-OspA ST2 and Variant 5 induced significantly higher surface binding than FL-OspA ST6. Variants 5 and 6 induced comparable binding as FL-OspA ST4 and lower binding than FL-OspA ST5. These Variants did not induce any surface binding to *B. burgdorferi* s.s. OspA ST1. Additionally, none of the Variants induced surface binding to *B. garinii* OspA ST3.

Furthermore, the growth inhibition assay was performed with *Borrelia* expressing OspA of respective serotypes on the surface and the amount of bactericidal antibodies needed to inhibit growth of spirochetes in presence of 1% guinea pig complement was evaluated (Table 1).

TABLE 1

Functional antibodies generated by multivalent OspA vaccine candidates as determined in growth inhibition assays.

| Immune sera | ST1 | ST2 | ST3 | ST4 | ST5 | ST6 |
|---|---|---|---|---|---|---|
| FL OspA | 1250 | 6250 | 6250 | 250 | 31250 | <50 |
| Variant 1 (α) | <50 | <50 | n.d. | <50 | <50 | 50 |
| Variant 2 (β) | 1250 | <50 | <50 | <50 | 1250 | 50 |
| Variant 3 (β) | 1250 | <50 | <50 | <50 | 1250 | 50 |
| Variant 4 (α) | <50 | <50 | n.d. | <50 | 50 | 50 |
| Variant 5 (β) | <50 | 1250 | 250 | 250 | 250 | 1250 |
| Variant 6 (β) | <50 | 1250 | 50 | 250 | 50 | 50 |

Growth inhibition assay was performed with *B. burgdorferi* ZS7 (ST1), *B. afzelii* Pra10 (ST2), *B. garinii* PFr (ST3), *B. bavariensis* PFin (ST4) and *B. garinii* PHei (ST5) and KL11 (ST6) strains. The growth inhibition (GI) titer is defined as the reciprocal of the lowest dilution showing ≥50% reduction in bacterial growth. n.d. = not done.

As shown in Table 1, Variant 1 and Variant 4 failed to inhibit the growth of any of the *Borrelia* strains tested. Variant 2 and Variant 3 generated comparable growth inhibition (GI) titers compared to FL-OspA ST1 while low GI titers were generated by both the Variants as compared to FL-OspA ST2 and FL-OspA ST5. None of Variants 1 to 4 generated a GI titer against *B. bavariensis* OspA ST4. Variant 5 and Variant 6 induced equivalent GI titers when compared to FL-OspA ST4 and lower GI titers when compared to FL-OspA ST2 and FL-OspA ST5. Variant 5 induced higher GT titers when compared to all the other Variants.

Example 4. Multivalent OspA Antigens Provided Significant Protection Against Major *Borrelia* Species and OspA Serotypes Pathogenic to Humans Based on the serology data presented above, four multivalent OspA antigens (Variants 2, 3, 5 and 6) were selected for evaluation of protection against *Borrelia* strains expressing five major OspA serotypes (ST1, ST2, ST4, ST5 and ST6). Variant 1 and Variant 4 were not pursued further since they generated very low levels of functional antibodies against the majority of OspA serotypes used in the study and they also resulted in sub-optimal protein yields. For the analysis of protection, mice were immunized with individual Variants V2, V3, V5 and V6 and were challenged with *I. ricinus* ticks infected with *B. burgdorferi* OspA ST1, *B. afzelii* OspA ST2 or *B. bavariensis* OspA ST4 or subcutaneously with 5×10$^4$ in vitro grown *B. burgdorferi* OspA ST1 or *B. garinii* ST5. In the case of tick challenge, the ticks were monitored until detachment and only mice with at least one tick with respect to ST2 or at least two ticks with respect to ST1 and ST4 feeding for >48 hours were included in the final infection readout.

As shown in Table 2, Variant 2 and Variant 3 demonstrated significant protection against all four OspA serotypes tested. Variant 5 and Variant 6 exhibited partial, non-significant, protection against a challenge with ticks harboring *B. burgdorferi* (OspA ST1). However, both Variants 5 and 6 provided significant protection against challenges with ticks infected with *B. afzelii* (OspA ST2) and *B. bavariensis* (OspA ST4).

For needle challenge, mice were injected subcutaneously two weeks after the final immunization with in vitro grown ZS7 (*B. burgdorferi* OspA ST1) or PHei (*B. garinii* OspA ST5) to determine the efficacy of multivalent variants. Variant 2 and Variant 3 provided 100% protection against challenge with ZS7 (OspA ST1) (Table 2). However, V5 and V6 conferred only partial, non-significant, protection against a challenge with ZS7 (OspA ST1). With respect to protection against challenge with PHei (OspA ST5), Variant 2 and Variant 3 induced highly significant protection. Conversely, Variant 5 and Variant 6 generated partial, non-significant protection, against challenge with PHei (OspA ST5).

TABLE 2

Protective efficacy of lipidated multivalent OspA Variants compared with full-length lipidated OspA proteins in challenge experiments.

| | | | Tick challenge | | | Subcutaneous challenge | | |
|---|---|---|---|---|---|---|---|---|
| | | | | | | | *B. garinii* | |
| | | | *B. burgdorferi* (ST1) | *B. afzelii* (ST2) | *B. bavariensis* (ST4) | *B. burgdorferi* (ST1) | (ST5) (two separate experiments) | |
| Immunogen | Serotypes | Dose | Infected/Total | Infected/Total | Infected/Total | Infected/Total | Infected/Total | Infected/Total |
| FL-OspA | 1, 2, 4 or 5 | 5 μg | 3/9* | 1/7*** | 0/6*** | 0/10*** | 0/10*** | 0/10*** |
| Variant 2 | 1, 4 & 5 | 5 μg | 1/7** | 3/8* | 0/4** | 0/10*** | 3/10$^{ns}$ | 4/10** |

TABLE 2-continued

Protective efficacy of lipidated multivalent OspA Variants compared
with full-length lipidated OspA proteins in challenge experiments.

| | | | Tick challenge | | | Subcutaneous challenge | | |
| --- | --- | --- | --- | --- | --- | --- | --- | --- |
| | | | | | | | B. garinii | |
| | | | B. burgdorferi (ST1) | B. afzelii (ST2) | B. bavariensis (ST4) | B. burgdorferi (ST1) | (ST5) (two separate experiments) | |
| Variant 3 | 1, 4 & 5 | 5 µg | 0/8*** | 4/10* | 1/9*** | 0/10*** | 0/10*** | 1/10*** |
| Variant 5 | 2, 3 & 6 | 5 µg | 5/8$^{ns}$ | 1/9*** | 0/7*** | 9/10$^{ns}$ | 3/5$^{ns}$ | 8/10$^{ns}$ |
| Variant 6 | 2, 3 & 6 | 5 µg | 6/9$^{ns}$ | 1/9*** | 0/7*** | 7/10$^{ns}$ | 7/10$^{ns}$ | 9/10$^{ns}$ |
| Placebo | — | — | 12/14 | 13/14 | 9/10 | 10/10 | 8/10 | 10/10 |

For efficacy analysis three immunizations were administered at two week intervals with polypeptides (5 µg) formulated with 0.15% aluminium hydroxide or with 0.15% aluminium hydroxide alone (placebo). Fifteen days after the third immunization, the mice were challenged with laboratory reared ticks infected with B. burgdorferi (ST1; strain Pra1), B. afzelii (ST2; strain IS1) or B. bavariensis (ST4; strain Marx1) or by subcutaneous injection, with $5 \times 10^4$ in vitro grown spirochetes B. burgdorferi (ST1, strain ZS7), B. garinii (ST5; strain PHei). For the tick challenge experiments, only mice with at least one tick (ST2) or two ticks (ST1 and ST4) feeding for >48 hours were included in the readout. Statistical significance was calculated with Fisher's exact test (two-tailed),
*$p < 0.05$,
**$p < 0.01$ and
***$p < 0.001$,
$^{ns}$not significant.

Example 5. Multivalent Fusion Vaccine Generates Comparable Immune Response as Well as Functional Antibodies Against Major *Borrelia* Species and OspA Serotypes Pathogenic to Humans The multivalent OspA fragments V2, V3, V5 and V6 demonstrated high levels of protection against clinically relevant *Borrelia* species expressing five different OspA serotypes (ST1, ST2, ST4, ST5 and ST6) (Example 4, Table 2). To produce a single antigen that may provide protection against multiple major OspA serotypes, a combination of the V3+V5 multivalent monomers was selected for further analysis. Variant 3 and Variant 5 were fused together with a 23 amino acid linker sequence derived from a loop region of P66 (Bunikis J. et al. 1998, J. Bact. 180(7):1618-1623 and Ornstein K. et al. 2002, Clin. Diag. Lab. Imm. 9(6):1382-1384) from *B. garinii* strain PBr, and a lipidation signal peptide was added at the N-terminal part. The resulting construct was expressed as single lipidated fusion polypeptide referred to as V3-L2-V5 (also referred to as "Lip-V3-L2-V5"). FIG. 3 shows a linear schematic representation of V3-L2-V5 (FIG. 3A) and a sequence alignment of the Variants 3 and 5 (FIG. 3B) with the conserved backbone of a *B. afzelii* C-terminal domain (aa 126-273, SEQ ID NO: 7).

Immunogenicity of the fusion protein was assessed and compared with that of the respective full-length OspA proteins. Mice were immunized with four doses of V3-L2-V5 vaccine (3, 0.3, 0.03 and 0.003 µg/mouse) or the respective FL-OspA (ST1-ST6; 1 µg/mouse) three times at two week intervals (all with 0.15% aluminium hydroxide). Immune sera were collected one week after the final immunization for analysis of OspA IgG antibodies by ELISA as well as surface binding and growth inhibition assays. As shown in FIG. 6, the V3-L2-V5 vaccine generated higher antibody titers than each of the individual OspA proteins FL-OspA ST1, ST4, ST5 and ST6 and generated similar titers with respect to the individual OspA proteins FL-OspA ST2 and ST3.

The functionality of the antibodies stimulated by vaccination with V3-L2-V5 was assessed by surface binding to *Borrelia* in vitro as well as growth inhibition of *Borrelia*. For these in vitro assays, pooled sera from mice immunized with a dose of 3 µg V3-L2-V5 were used. As shown in FIG. 7, immunization with V3-L2-V5 generated surface binding to spirochetes expressing OspA ST1, ST2, ST4 and ST5 that was comparable with antibodies generated in response to the FL-OspA proteins (1 µg/mouse) of the respective serotype. The surface binding of V3-L2-V5 sera to spirochetes expressing OspA ST6 on the surface was higher when compared to the FL-OspA-ST6 immunized mice.

As shown in Table 3, growth inhibition titers generated by immunization with V3-L2-V5 were higher than those from the respective FL-OspA proteins for spirochetes expressing OspA ST1, ST5 and ST6, comparable with respect to spirochetes expressing OspA ST2 and lower than with respect to OspA ST4.

TABLE 3

Functional antibodies generated by chimeric OspA vaccine candidates as determined by *Borrelia* growth inhibition.

| Immune sera | ST1 | ST2 | ST3 | ST4 | ST5 | ST6 |
| --- | --- | --- | --- | --- | --- | --- |
| FL-OspA | 250 | 6250 | 6250 | 31250 | 250 | <50 |
| V3-L2-V5 | 1250 | 1250 | <50 | 6250 | 1250 | 250 |

Growth inhibition was analyzed with *B. burgdorferi* (ST1; strain ZS7), *B. afzelii* (ST2; strain Pra10), *B. garinii* (ST3; strain PFr), *B. bavariensis* (ST4; strain PFin), *B. garinii* (ST5; strain PHei) and KL11 (ST6) strains. The growth inhibition (GI) titer is defined as the reciprocal of the lowest dilution with ≥50% reduction in bacterial growth.

Example 6. Fusion V3-L2-V5 Vaccine Protects Against Two Major Human Pathogenic *Borrelia* Species of Global Importance The protective efficacy of the V3-L2-V5 vaccine was tested against the two most clinically relevant *Borrelia* species; i.e., *B. burgdorferi* (OspA ST1) and *B. afzelii* (OspA ST2). For this study, V3-L2-V5 was compared with the respective FL-OspA proteins in a needle challenge with in vitro grown *B. burgdorferi* (OspA ST1) and ticks infected with *B. afzelii* (OspA ST2). As shown in Table 4, the V3-L2-V5 conferred highly significant protection against *B. burgdorferi* (OspA ST1) at the three highest immunization doses.

TABLE 4

Efficacy of the V3-L2-V5 multivalent fusion vaccine in comparison with full-length OspA proteins against B. burgdorferi OspA ST1 needle challenge and B. afzelii OspA ST2 tick challenge.

|  | Serotypes | Dose/mouse (with 0.15% Alum) | Needle Challenge B. burgdorferi (ST1) Infected/Total number of mice | Tick Challenge B. afzelii (ST2) Infected/Total number of mice |
|---|---|---|---|---|
| FL-OspA | ST1 | 1 µg | 6/10$^{ns}$ | — |
| FL-OspA | ST2 | 1 µg | — | 0/18*** |
| V3-L2-V5 | ST1-6 | 3 µg | 0/10*** | 0/9*** |
|  |  | 0.3 µg | 0/10*** | 0/9*** |
|  |  | 0.03 µg | 0/10*** | 0/9*** |
|  |  | 0.003 µg | 2/10* | 6/9$^{ns}$ |
| Placebo | — | — | 8/10 | 15/16 |

Mice were challenged with ticks infected with B. afzelii (ST2; strain IS1) or were subcutaneously injected with 5 × 10$^4$ in vitro grown B. burgdorferi (ST1; strain ZS7). The infection status was assessed after four weeks with VlsE ELISA. For B. afzelii tick challenge experiments, only mice with at least one tick feeding for >48 hours were included in the readout. Statistical significance was calculated with Fisher's exact test (two-tailed),
*p < 0.05,
**p < 0.01 and
***p < 0.001,
$^{ns}$not significant.

Notably, as shown in Table 4, V3-L2-V5 demonstrated significant protection even at the lowest dose of 3 ng demonstrating a high protective efficacy against a *B. burgdorferi* (OspA ST1) challenge. For challenge with *B. afzelii* (OspA ST2) infected ticks, the same batch of ticks was used and therefore the results of two different experiments were combined. Vaccination with V3-L2-V5 provided 100% protection against challenge with *B. afzelii* (OspA ST2) infected ticks and the protection generated was comparable to that of FL-OspA2. The results indicate 100% protection of the fusion protein V3-L2-V5 vaccine in a lower antigen dose of 0.03 µg demonstrating high efficacy of the candidate, which was higher when compared to FL-OspA ST1 against a *B. burgdorferi* needle challenge and comparable to FL OspA ST2 against a *B. afzelii* tick challenge.

Example 7. Immunogenicity of Hybrid Serotype 3 C-Terminal OspA Domains in the Context of Heterodimers in a Combination Vaccine Immunization of Mice Female C3H/HeN mice were used for all studies. Prior to immunizations, groups of ten mice were bled via the facial vein and pre-immune sera were prepared and pooled. Three s.c. immunizations of 100 µL each were administered at two week intervals. Mice were immunized with 1 µg of the control full-length serotype 3 OspA protein or with 1 µg each of the respective proteins in the combination vaccines. The contents of each immunogen are detailed in Table 5 below. All vaccines were formulated with aluminium hydroxide (Al(OH)$_3$) at a final concentration of 0.15%. One week after the third immunization, blood was collected from the facial vein and immune sera prepared. In each experiment, one group immunized with PBS formulated with Al(OH)$_3$ was included as a negative control (placebo group). All animal experiments were conducted in accordance with Austrian law (BGB1 Nr. 501/1989) and approved by "Magistratsabteilung 58".

OspA ELISA

ELISA plates (Maxisorp, Nunc, Denmark) were coated with 50 ng (1 µg/mL) protein diluted in coating buffer (PBS) per well and incubated at 4° C. for 16 to 72 hours. The coating antigen was C-terminally His-tagged full-length lipidated OspA ST3 (SEQ ID NO: 3). The coating buffer was discarded and 100 µL blocking buffer (1% BSA, 0.5% Tween-20, PBS) was added and incubated at ambient temperature for 1-2 hours. Plates were washed three times with 300 µL (overflow) PBST (0.1% Tween-20, PBS). Five-fold dilutions of the sera were prepared in blocking buffer and 50 µL, were added to each well and incubated for 1 hour at ambient temperature. Plates were washed three times with 300 µL (overflow) PBST. The secondary antibody (horseradish peroxidase [HRP]-conjugated rabbit anti-mouse IgG, DAKO, Denmark) was diluted 1:2000 in blocking buffer and 50 µL was added to each well and incubated for 1 hour at ambient temperature. Plates were washed three times with 300 µL (overflow) PBST. ABTS (2,2'-azino-bis(3-ethylbenzothiazoline-6-sulfonic acid), Sigma-Aldrich, USA) was used as substrate for HRP, 50 µL of ABTS was added to each well and incubated for 15 minutes in the dark at ambient temperature. The reaction was stopped by the addition of 50 µL 1% SDS and the absorbance was read at 405 nm. A plate was regarded as valid when the absorbance of the blank was below 0.1. A sample was valid when the lowest dilution had an absorbance above 1.0 and the highest dilution was below 0.1. When these criteria were met, the half-max titer was determined. The half-max titer is the reciprocal of the dilution that corresponds to the mean absorbance between the highest and lowest dilutions.

Flow Cytometry

Spirochetes (1×10$^6$) were mixed with an equal volume of 4% paraformaldehyde and incubated for 2 hours at room temperature in a 96-well plate (Nunclon 96U, Nunc). The plate was centrifuged for 5 minutes at 2,000 g and the supernatant was discarded. Cells were washed with 150 µL HBSS with 2% BSA (HBSS-B), centrifuged as above, and the supernatant was discarded. Mouse sera were heat inactivated by incubation at 56° C. for 35 minutes. Heat-inactivated sera were diluted in HBSS-B and sterile filtered by centrifuging at 4,000 g for 3 minutes using Costar spin-X centrifuge tube filters (0.22 µm, Corning, USA). Spirochetes were dissolved in 100 µL serum and incubated for 45 minutes at room temperature. The plate was centrifuged for 15 minutes at 2,000 g and the supernatant was discarded. The cells were washed once with 150 µL HBSS-B and then resuspended in 100 µL HBSS-B. One microliter secondary antibody (PE-conjugated goat anti-mouse IgG, Beckman Coulter, USA) was added to the cells and incubated at room temperature for 45 minutes in the dark. Spirochetes were washed once with 150 μL HBSS-B and then resuspended in 200 μL HBSS containing 2.5 μM SYTO-17 DNA dye and incubated for 10 minutes at room temperature in the dark. The stained spirochetes were pelleted by centrifuging for 5 minutes at 2,000 g and subsequently resuspended in 200 μL HBSS. Labelled spirochetes were measured with an FC500 (Beckman Coulter) flow cytometer, gated for SYTO-17 positive events.

Results

Three different OspA heterodimer formulations ("het combo" and "BvaHyb het combo" and "BspHyb het combo") as well as an combination of full-length OspA chimeras ("chimera combo") were tested for immunogenicity in mice. Full-length serotype 3 OspA served as a positive control. Hyperimmune sera were analysed by ELISA for reactivity against full-length serotype 3 OspA (coating antigen) as well as for surface binding to *Borrelia* spirochetes expressing OspA serotype 3. As shown in FIG. 9, the ELISA results indicated that all vaccine combinations stimulated antibody responses to serotype 3 OspA.

As shown in FIG. 10, binding of antibodies from hyperimmune mouse sera directly to *Borrelia* spirochetes was observed in the case of *Borrelia garinii*, strain Fr, expressing serotype 3 OspA, indicating that the antibodies generated are functionally active and can bind native OspA in situ. The fluorescence intensity was linear over a large range of serum dilutions. The fluorescence intensity observed in response to the improved heterodimer combination vaccine to spirochetes was comparable to those observed in response to the heterodimer combination vaccine and the chimera combination vaccine. Again, notably, with regard to binding to serotype 3 OspA *Borrelia* spirochetes, the antibodies generated by the BvaHyb het combo and the BspHyb het combo, despite their relatively low sequence identity, were comparably functional.

TABLE 5

Combination vaccine immunization groups. All immunogens were formulated with 0.15% aluminium hydroxide.

| Immunogen | Dose at 2-week intervals |
| --- | --- |
| Full-length lipidated serotype 3 OspA Lip-OspA3-His (SEQ ID NO: 3) | 3 × 1.0 μg |
| Chimera combination vaccine (Chimera combo) Lip-Chimeric OspA ST1/ST2-His (Seq ID No: 69) Lip-Chimeric OspA ST5/ST3-His (Seq TD No: 70) Lip-Chimeric OspA ST6/ST4-His (Seq ID No: 71) | 3 × 3 μg (1.0 μg each) |
| Heterodimer combination vaccine (Het combo) Lip-S1D1-S2D1 (Seq ID No: 50) Lip-S4D1-S3D1 (Seq ID No: 52) Lip-S5D1-S6D1 (Seq ID No: 54) | 3 × 3 μg (1.0 μg each) |
| BvaHyb heterodimer combination vaccine (BvaHyb het combo) Lip-S1D1-S2D1 (Seq ID No: 50) Lip-S4D1-S3hybD1-Bva (Seq ID No: 48) Lip-S5D1-S6D1 (Seq ID No: 54) | 3 × 3 μg (1.0 μg each) |
| BspHyb heterodimer combination vaccine (BspHyb combo) Lip-S1D1-S2D1 (Seq ID No: 50) Lip-S4Dl-S3hybD1-Bsp (Seq ID No: 72) Lip-S5D1-S6D1 (Seq ID No: 54) | 3 × 3 μg (1.0 μg each) |

CONCLUSIONS

The herein described analysis of the multivalent OspA fragment Variants demonstrated that a reduction of the number of proteins in the final vaccine formulation could be achieved without compromising on broad protection against the most clinically relevant strains of pathogenic *Borrelia* species and OspA serotypes. With a single vaccine formulation, the cost and complexity of the OspA vaccine production can be reduced significantly, as long as the production yield is maintained.

Variant 1 and Variant 4, with a-type disulfide bonds were difficult to produce, having low levels of protein expression and yield. Furthermore, it was observed that these Variants generated functional antibodies only at levels much lower than those observed with Variant 2 and Variant 3, which are stabilized with the β-type disulfide bond. Although none of the Variants showed growth inhibition against *B. bavariensis* OspA ST4, the titers of Variant 2 and Variant 3 were significantly higher with respect to *B. burgdorferi* OspA ST1 and *B. garinii* OspA ST5. These results underscore the importance of the position of the disulfide bond on expression, yield and immunogenicity of the chimeric candidates and that preservation of proper protein folding in physiological temperatures is important.

Based on these results, Variant 2 and Variant 3 were selected further for studying the efficacy against challenge with major human pathogenic *Borrelia* species and serotypes. In Variant 2 and Variant 3, OspA ST5 and OspA ST4 were interchanged between patch G and H to study the effect on immunogenicity as well as protection generated against these serotypes. However, no significant difference in either immunogenicity or protection with respect to tick challenge with *B. bavariensis* OspA ST4 or needle challenge with *B. garinii* OspA ST5 was observed between these two Variants.

Variant 5 and Variant 6 stabilized with the n-type disulfide bond were designed with a serotype switch on patch A (i.e. ST6 on Variant 5 and ST2 on Variant 6) to study the effect on immunogenicity as well as protection generated against these two serotypes. With respect to immunogenicity, both variants generated similar immune responses to FL-OspA ST2 but the immune response to Variant 5 was higher as compared to Variant 6 against FL OspA ST6. In addition, Variant 5 and Variant 6 also generated comparable surface binding and growth inhibition titer against *B. afzelii* OspA ST2.

Variant 2 and Variant 3 generated significantly lower antibody titers and functional antibodies against *B. afzelii* OspA ST2 as compared with Variant 5 and Variant 6, but provided significant protection against challenge with *B. afzelii* OspA ST2 infected ticks. These data suggest that, even if the immune response generated was lower, significant cross-protection may be conferred. Additionally, comparing Variant 2 and Variant 3 with respect to OspA ST2, the functional antibodies and protection generated by Variant 3 was slightly better than that of Variant 2. This also suggests an effect of serotype interchange between these Variants, although OspA ST2 was not the serotype in question. Variant 2 and Variant 3 generated antibody titers to the level of Variant 5 and Variant 6 with respect to *B. garinii* OspA ST6. Therefore, Variant 2 and Variant 3 were cross-reactive with *B. garinii* OspA ST6 despite not having ST6 serotype specific amino acid residues on their surfaces. Furthermore, Variant 5 and Variant 6, when compared with Variant 2 and Variant 3, generated significantly lower antibody titers and functional antibodies with respect to *B. burgdorferi* s.s. OspA ST1 and *B. garinii* OspA ST5. Similarly, Variant 5 and Variant 6 did not demonstrate significant protection against a needle challenge with OspA ST1 and ST5 or tick challenge against OspA ST1. Since Variant 5 and Variant 6 do not include OspA ST1 or ST5 serotype specific residues on their surface, very low cross-reaction and partial non-significant protection was observed against these serotypes. Conversely, Variant 5 and Variant 6 despite not presenting *B. bavariensis* OspA ST4 residues on the surface generated similar antibody titers and higher functional antibodies as compared with Variant 2 and Variant 3. Variant 5 and Variant 6 also demonstrated highly significant protection against challenge with *B. bavariensis* OspA ST4 infected ticks, which suggest that these Variants are highly cross-reactive and protective against *B. bavariensis* OspA ST4. With respect to *B. garinii* OspA ST3, Variant 2 and Variant 3 demonstrated a lower immune response as compared with Variant 5 and Variant 6. Probably because Variant 2 and 3 did not represent OspA ST3 amino acid residues on any of their patches, very low cross-reacting antibodies were generated.

Variant 3 and Variant 5 as individual candidates were observed to have slightly higher immunogenicity with respect to OspA ST2 and OspA ST6 than Variant 2 or Variant 6. Therefore, the V3 and V5 OspA fragment Variants were linked together with a short and flexible sequence (23 amino acids) to produce a single lipidated fusion protein named V3-L2-V5. The linker sequence used in V3-L2-V5 is a short 23 amino acid long sequence (SEQ ID NO: 32), which is derived from P66 protein of *B. garinii* strain PBr. The loop sequence is reported to be immunogenic in humans (Bunikis J. et al. 1998, supra and Ornstein K. et al. 2002, supra). OspA based vaccines are protective through circulating antibodies that neutralize the spirochetes in the mid-gut of the tick. Therefore, antibodies recognizing the P66 linker could potentially target spirochetes which may not have been neutralized by OspA antibodies in the tissue of the host to further enhance the efficacy of the fusion protein vaccine.

The multivalent lipidated fusion antigen V3-L2-V5 generated higher antibody titers than the FL-OspA proteins of OspA ST1, ST4, ST5 and ST6 and comparable antibody titers to FL-OspA ST2 and ST3. These results demonstrate that the single multivalent lipidated V3-L2-V5 antigen has the potential to generate protective antibodies against all major clinically-relevant OspA serotypes. This data is further substantiated by the functional assays (surface staining and growth inhibition) where the fusion vaccine generated was able to induce high titers of functional antibodies that could bind and inhibit the growth of live spirochetes in vitro. The V3-L2-V5 vaccine demonstrated 100% protection against needle challenge with in vitro grown *B. burgdorferi* s.s. OspA ST1 and tick challenge with *B. afzelii* OspA ST2 in the first three immunization doses investigated. Intriguingly, V3-L2-V5 was highly potent since protection was observed even with a dose of 3 ng against a challenge with in vitro grown *B. burgdorferi* s.s. OspA ST1 and a dose of 30 ng against a challenge with *B. afzelii* OspA ST2 infected ticks. The efficacy of the new vaccine was higher than that of FL-OspA ST1 protein and comparable to the FL-OspA ST2 in the respective challenge models. The results presented herein show a high pre-clinical efficacy and proof-of-principle of a new multivalent Lyme borreliosis vaccine with a potential to achieve broad protection with a single protein, with the potential to simplify the process of OspA vaccine production and making it more cost-effective.

```
SEQUENCES
Lip-FL-OspA1 full-length OspA from Borrelia burgdorferi
B31 with C-terminal His-tag (LEHHHHHH) and lipidated
N-terminal CSS peptide
                                                     SEQ ID NO: 1
LipCSSFKQNVSSLDEKNSVSVDLPGEMKVLVSKEKNKDGKYDLIATVDKLELKGTSDKNNGSGVLEGVK

ADKSKVKLTISDDLGQTTLEVFKEDGKTLVSKKVTSKDKSSTEEKFNEKGEVSEKIITRADGTRLEYTGI

KSDGSGKAKEVLKGYVLEGTLTAEKTTLVVKEGTVTLSKNISKSGEVSVELNDTDSSAATKKTAAWNSGT

STLTITVNSKKTKDLVFTKENTITVQQYDSNGTKLEGSAVEITKLDEIKNALKLEHHHHHH

Lip-FL-OspA2 full-length OspA from Borrelia afzelii
K78 with C-terminal His-tag (LEHHHHHH) and lipidated
N-terminal CSS peptide
                                                     SEQ ID NO: 2
LipCSSFKQNVSSLDEKNSASVDLPGEMKVLVSKEKDKDGKYSLKATVDKIELKGTSDKDNGSGVLEGTK

DDKSKAKLTIADDLSKTTFELFKEDGKTLVSRKVSSKDKTSTDEMFNEKGELSAKTMTRENGTKLEYTEM

KSDGTGKAKEVLKNFTLEGKVANDKVTLEVKEGTVTLSKEIAKSGEVTVALNDTNTTQATKKTGAWDSKT

STLTISVNSKKTTQLVFTKQDTITVQKYDSAGTNLEGTAVEIKTLDELKNALKLEHHHHHH
```

-continued

Lip-FL-OspA3 full-length OspA from *Borrelia garinii*
PBr with C-terminal His-tag (LEHHHHHH) and lipidated
N-terminal CSS peptide

SEQ ID NO: 3

LipCSSFKQNVSSLDEKNSVSVDLPGGMKVLVSKEKDKDGKYSLMATVEKLELKGTSDKSNGSGVLEGEK

ADKSKAKLTISQDLNQTTFEIFKEDGKTLVSRKVNSKDKSSTEEKFNDKGKLSEKVVTRANGTRLEYTEI

KNDGSGKAKEVLKGFALEGTLTDGGETKLTVTEGTVTLSKNISKSGEITVALNDTETTPADKKTGEWKSD

TSTLTISKNSQKTKQLVFTKENTITVQNYNRAGNALEGSPAEIKDLAELKAALKLEHHHHHH

Lip-FL-OspA4 full-length OspA from *Borrelia bavariensis*
PBi with C-terminal His-tag (LEHHHHHH) and lipidated
N-terminal CSS peptide

SEQ ID NO: 4

LipCSSFKQNVSSLDEKNSVSVDLPGEMKVLVSKEKDKDGKYSLMATVDKLELKGTSDKSNGSGTLEGEK

SDKSKAKLTISEDLSKTTFEIFKEDGKTLVSKKVNSKDKSSIEEKFNAKGELSEKTILRANGTRLEYTEI

KSDGTGKAKEVLKDFALEGTLAADKTTLKVTEGTVVLSKHIPNSGEITVELNDSNSTQATKKTGKWDSNT

STLTISVNSKKTKNIVFTKEDTITVQKYDSAGTNLEGNAVEIKTLDELKNALKLEHHHHHH

Lip-FL-OspA5 full-length OspA from *Borrelia garinii*
PHei with C-terminal His-tag (LEHHHHHH) and lipidated
N-terminal CSS peptide

SEQ ID NO: 5

LipCSSFKQNVSSLDEKNSVSVDLPGGMKVLVSKEKDKDGKYSLMATVEKLELKGTSDKNNGSGTLEGEK

TDKSKVKLTIAEDLSKTTFEIFKEDGKTLVSKKVTLKDKSSTEEKFNEKGEISEKTIVRANGTRLEYTDI

KSDKTGKAKEVLKDFTLEGTLAADKTTLKVTEGTVTLSKNISKSGEITVALDDTDSSGNKKSGTWDSGT

STLTISKNRTKTKQLVFTKEDTITVQNYDSAGTNLEGKAVEITTLKELKNALKLEHHHHHH

Lip-FL-OspA6 full-length OspA from *Borrelia garinii*
DK29 with C-terminal His-tag (LEHHHHHH) and lipidated
N-terminal CSS peptide

SEQ ID NO: 6

LipCSSFKQNVSSLDEKNSVSVDLPGGMTVLVSKEKDKDGKYSLEATVDKLELKGTSDKNNGSGTLEGEK

TDKSKVKSTIADDLSQTKFEIFKEDGKTLVSKKVTLKDKSSTEEKFNGKGETSEKTIVRANGTRLEYTDI

KSDGSGKAKEVLKDFTLEGTLAADKTTLKVTEGTVVLSKNILKSGEITAALDDSDTTRATKKTGKWDSK

TSTLTISVNSQKTKNLVFTKEDTITVQRYDSAGTNLEGKAVEITTLKELKNALKLEHHHHHH

Conserved amino acid "scaffold" sequence of
*B. afzelii* OspA ST2 (K78)

SEQ ID NO: 7

FNEKGELSAKTMTRENGTKLEYTEMKSDGTGKAKEVLKNFTLEGKVANDKVTLEVKEGTVTLSKEIAKSG

EVTVALNDTNTTQATKKTGAWDSKTSTLTISVNSKKTTQLVFTQKDTITVKQYDSAGTNLEGTAVEIKTL

DELKNALK

Variant 1 (ST1, 4, 5) with alpha-type bond

SEQ ID NO: 8

FNEKGEISEKTIVRANGTRLEYTDIKSDKTGKAKEVLKDFTLEGTVAADKVTLKVTEGTVTLSKHIPNSG

EITVELDDTDSSAATKKTAAWDSNTSTLTITVNSKKTKNLVFTKEDTICVQNYDSNGTNLEGKCVEITTL

KELKNALK

Variant 2 (ST1, 4, 5) with beta-type bond

SEQ ID NO: 9

FNEKGEISEKTIVRANGTRLEYTDIKSDKTGKAKEVLKDFTLEGTVAADKVTLKVTCGTVTLSKHIPNSG

EITVELDDTDSSAATKKTAAWDSNTSTLTITVNSKKTKNLVFTKEDTITVQNYDSNGTNLEGKAVEITTL

KELCNALK

Variant 3 (ST1, 4, 5) with p-type bond

SEQ ID NO: 10

FNAKGELSEKTILRANGTRLEYTEIKSDGTGKAKEVLKDFALEGTVAADGKVTLKVTCGTVTLSKNISKS

GEITVALDDTDSSAATKKTAAWDSGTSTLTITVNSKKTKQLVFTKEDTITVQNYDSNGTNLEGKAVEITT

LKELCNALK

-continued

Variant 4 (ST1, 4, 5) with beta-type bond
SEQ ID NO: 11
FNAKGELSEKTILRANGTRLEYTEIKSDGTGKAKEVLKDFALEGTVAADGKVTLKVTEGTVTLSKNISKS
GEITVALDDTDSSAATKKTAAWDSGTSTLTITVNSKKTKQLVFTKEDTICVQNYDSNGTNLEGKCVEITT
LKELKNALK Variant 5 (ST2, 3, 6) with beta-type bond
SEQ ID NO: 12
FNEKGELSAKTMTRENGTKLEYTEMKSDGTGKAKEVLKNFTLEGKVANDKVTLEVKCGTVTLSKEIAKSG
EVTVALNDTNTTRATKKTGKWDSKTSTLTISVNSQKTKNLVFTKEDTITVQNYDSAGTNLEGSPAEIKDL
AELCAALK Variant 6 (ST2, 3, 6) with beta-type bond
SEQ ID NO: 13
FNEKGELSAKTMTRENGTKLEYTEMKSDGTGKAKEVLKNFTLEGKVANDKVTLEVKCGTVTLSKEIAKSG
EVTVALNDTNTTQATKKTGAWDSKTSTLTISVNSKKTKNLVFTKEDTITVQNYDSAGTNLEGSPAEIKDL
AELCAALK Lip-Variant 1 (ST1, 4, 5) with alpha-type bond, C-terminal
His-tag (HHHHHH) and lipidated N-terminal CSS peptide
SEQ ID NO: 14
LipCSSFNEKGEISEKTIVRANGTRLEYTDIKSDKTGKAKEVLKDFTLEGTVAADKVTLKVTEGTVTLSK
HIPNSGEITVELDDTDSSAATKKTAAWDSNTSTLTITVNSKKTKNLVFTKEDTICVQNYDSNGTNLEGKC
VEITTLKELKNALKHHHHHH Lip-Variant 2 (ST1, 4, 5) with beta-type bond, C-terminal
His-tag (HHHHHH) and lipidated N-terminal CSS peptide
SEQ ID NO: 15
LipCSSFNEKGEISEKTIVRANGTRLEYTDIKSDKTGKAKEVLKDFTLEGTVAADKVTLKVTCGTVTLSK
HIPNSGEITVELDDTDSSAATKKTAAWDSNTSTLTITVNSKKTKNLVFTKEDTITVQNYDSNGTNLEGKA
VEITTLKELCNALKHHHHHH Lip-Variant 3 (ST1, 4, 5) with beta-type bond, C-terminal
His-tag (HHHHHH) and lipidated N-terminal CSS peptide
SEQ ID NO: 16
LipCSSFNAKGELSEKTILRANGTRLEYTEIKSDGTGKAKEVLKDFALEGTVAADGKVTLKVTCGTVTLS
KNISKSGEITVALDDTDSSAATKKTAAWDSGTSTLTITVNSKKTKQLVFTKEDTITVQNYDSNGTNLEGK
AVEITTLKELCNALKHHHHHH Lip-Variant 4 (ST1, 4, 5) with alpha-type bond, C-terminal
His-tag (HHHHHH) and lipidated N-terminal CSS peptide
SEQ ID NO: 17
LipCSSFNAKGELSEKTILRANGTRLEYTEIKSDGTGKAKEVLKDFALEGTVAADGKVTLKVTEGTVTLS
KNISKSGEITVALDDTDSSAATKKTAAWDSGTSTLTITVNSKKTKQLVFTKEDTICVQNYDSNGTNLEGK
CVEITTLKELKNALKHHHHHH Lip-Variant 5 (ST2, 3, 6) with beta-type bond, C-terminal
His-tag (HHHHHH) and lipidated N-terminal CSS peptide
SEQ ID NO: 18
LipCSSFNEKGELSAKTMTRENGTKLEYTEMKSDGTGKAKEVLKNFTLEGKVANDKVTLEVKCGTVTLSK
EIAKSGEVTVALNDTNTTRATKKTGKWDSKTSTLTISVNSQKTKNLVFTKEDTITVQNYDSAGTNLEGSP
AEIKDLAELCAALKHHHHHH Lip-Variant 6 (ST2, 3, 6) with beta-type bond, C-terminal
His-tag (HHHHHH) and lipidated N-terminal CSS peptide
SEQ ID NO: 19
LipCSSFNEKGELSAKTMTRENGTKLEYTEMKSDGTGKAKEVLKNFTLEGKVANDKVTLEVKCGTVTLSK
EIAKSGEVTVALNDTNTTQATKKTGAWDSKTSTLTISVNSKKTKNLVFTKEDTITVQNYDSAGTNLEGSP
AEIKDLAELCAALKHHHHHH -continued Lip-Variant 1 (ST1, 4, 5) with alpha-type bond and lipidated
N-terminal CSS peptide
SEQ ID NO: 20
LipCSSFNEKGEISEKTIVRANGTRLEYTDIKSDKTGKAKEVLKDFTLEGTVAADKVTLKVTEGTVTLSK

HIPNSGEITVELDDTDSSAATKKTAAWDSNTSTLTITVNSKKTKNLVFTKEDTICVQNYDSNGTNLEGKC

VEITTLKELKNALK

Lip-Variant 2 (ST1, 4, 5) with beta-type bond and lipidated
N-terminal CSS peptide
SEQ ID NO: 21
LipCSSFNEKGEISEKTIVRANGTRLEYTDIKSDKTGKAKEVLKDFTLEGTVAADKVTLKVTCGTVTLSK

HIPNSGEITVELDDTDSSAATKKTAAWDSNTSTLTITVNSKKTKNLVFTKEDTITVQNYDSNGTNLEGKA

VEITTLKELCNALK

Lip-Variant 3 (ST1, 4, 5) with beta-type bond and lipidated
N-terminal CSS peptide
SEQ ID NO: 22
LipCSSFNAKGELSEKTILRANGTRLEYTEIKSDGTGKAKEVLKDFALEGTVAADGKVTLKVTCGTVTLS

KNISKSGEITVALDDTDSSAATKKTAAWDSGTSTLTITVNSKKTKQLVFTKEDTITVQNYDSNGTNLEGK

AVEITTLKELCNALK

Lip-Variant 4 (ST1, 4, 5) with alpha-type bond and lipidated
N-terminal CSS peptide
SEQ ID NO: 23
LipCSSFNAKGELSEKTILRANGTRLEYTEIKSDGTGKAKEVLKDFALEGTVAADGKVTLKVTEGTVTLS

KNISKSGEITVALDDTDSSAATKKTAAWDSGTSTLTITVNSKKTKQLVFTKEDTICVQNYDSNGTNLEGK

CVEITTLKELKNALK

Lip-Variant 5 (ST2, 3, 6) with beta-type bond and lipidated
N-terminal CSS peptide
SEQ ID NO: 24
LipCSSFNEKGELSAKTMTRENGTKLEYTEMKSDGTGKAKEVLKNFTLEGKVANDKVTLEVKCGTVTLSK

EIAKSGEVTVALNDTNTTRATKKTGKWDSKTSTLTISVNSQKTKNLVFTKEDTITVQNYDSAGTNLEGSP

AEIKDLAELCAALK

Lip-Variant 6 (ST2, 3, 6) with beta-type bond and lipidated
N-terminal CSS peptide
SEQ ID NO: 25
LipCSSFNEKGELSAKTMTRENGTKLEYTEMKSDGTGKAKEVLKNFTLEGKVANDKVTLEVKCGTVTLSK

EIAKSGEVTVALNDTNTTQATKKTGAWDSKTSTLTISVNSKKTKNLVFTKEDTITVQNYDSAGTNLEGSP

AEIKDLAELCAALK

Lip-V3-L2-V5-His6 (protein sequence) with C-terminal His-tag
(LEHHHHHH) and lipidated N-terminal CSS peptide
SEQ ID NO: 26
LipCSSFNAKGELSEKTILRANGTRLEYTEIKSDGTGKAKEVLKDFALEGTVAADGKVTLKVTCGTVTLS

KNISKSGEITVALDDTDSSAATKKTAAWDSGTSTLTITVNSKKTKQLVFTKEDTITVQNYDSNGTNLEGK

AVEITTLKELCNALKGTSANNQAGQKSSGSTQATTPNLTFEKYSFNEKGELSAKTMTRENGTKLEYTEMK

SDGTGKAKEVLKNFTLEGKVANDKVTLEVKCGTVTLSKEIAKSGEVTVALNDTNTTRATKKTGKWDSKTS

TLTISVNSQKTKNLVFTKEDTITVQNYDSAGTNLEGSPAEIKDLAELCAALKLEHHHHHH

Lip-V3-L2-V5-His6 (nucleotide sequence) with C-terminal
His-tag (LEHHHHHH)
SEQ ID NO: 27
TGCTCAAGCTTCAATGCAAAAGGTGAACTGAGCGAAAAAACCATTCTGCGTGCAAATGGCACCCGTCTGG

AATATACCGAAATCAAAAGTGATGGCACCGGTAAAGCAAAAGAAGTGCTGAAAGATTTTGCACTGGAAGG

CACCGTTGCAGCAGATGGTAAAGTTACCCTGAAAGTTACCTGTGGCACCGTGACCCTGAGCAAAAACATT

AGCAAAAGCGGTGAAATTACCGTTGCCCTGGATGATACCGATAGCAGCGCAGCAACCAAAAAAACCGCAG

CATGGGATAGCGGCACCAGCACCCTGACCATTACCGTTAATAGTAAAAAAACCAAACAGCTGGTGTTTAC

-continued

CAAAGAGGATACCATTACGGTTCAGAACTATGATAGCAATGGTACGAATCTGGAAGGTAAAGCCGTTGAA

ATCACCACACTGAAAGAACTGTGTAATGCACTGAAAGGTACTAGTGCAAATAATCAGGCAGGTCAGAAAA

GCAGCGGTAGCACCCAGGCAACCACCCCGAATCTGACCTTTGAAAAGTACTCATTTAACGAGAAAGGCGA

GCTGTCAGCAAAAACCATGACCCGTGAAAATGGAACCAAACTGGAATACACGGAAATGAAATCAGATGGT

ACAGGCAAAGCCAAAGAGGTCCTGAAAAACTTCACCCTGGAAGGGAAAGTTGCCAATGATAAAGTGACAC

TGGAAGTTAAATGTGGTACAGTTACACTGAGCAAAGAAATTGCCAAATCAGGTGAAGTGACCGTGGCACT

GAATGATACAAATACCACCCGTGCCACAAAAAAAACAGGTAAATGGGATAGTAAAACGAGCACACTGACA

ATTAGTGTGAATAGCCAGAAAACGAAAAACCTGGTGTTCACGAAAGAAGATACAATCACCGTACAGAATT

ATGATTCAGCAGGCACCAACCTGGAAGGTTCACCGGCAGAAATTAAAGATCTGGCCGAACTGTGTGCAGC

CCTGAAACTCGAGCACCACCACCACCACCAC

Lip-V3-L2-V5 (protein sequence) with lipidated N-terminal
CSS peptide
                                                    SEQ ID NO: 28
LipCSSFNAKGELSEKTILRANGTRLEYTEIKSDGTGKAKEVLKDFALEGTVAADGKVTLKVTCGTVTLS

KNISKSGEITVALDDTDSSAATKKTAAWDSGTSTLTITVNSKKTKQLVFTKEDTITVQNYDSNGTNLEGK

AVEITTLKELCNALKGTSANNQAGQKSSGSTQATTPNLTFEKYSFNEKGELSAKTMTRENGTKLEYTEMK

SDGTGKAKEVLKNFTLEGKVANDKVTLEVKCGTVTLSKEIAKSGEVTVALNDTNTTRATKKTGKWDSKTS

TLTISVNSQKTKNLVFTKEDTITVQNYDSAGTNLEGSPAEIKDLAELCAALK

Lip-V3-L2-V5 (nucleotide sequence)

SEQ ID NO: 29

TGCTCAAGCTTCAATGCAAAAGGTGAACTGAGCGAAAAAACCATTCTGCGTGCAAATGGCACCCGTCTGG

AATATACCGAAATCAAAAGTGATGGCACCGGTAAAGCAAAAGAAGTGCTGAAAGATTTTGCACTGGAAGG

CACCGTTGCAGCAGATGGTAAAGTTACCCTGAAAGTTACCTGTGGCACCGTGACCCTGAGCAAAAACATT

AGCAAAAGCGGTGAAATTACCGTTGCCCTGGATGATACCGATAGCAGCGCAGCAACCAAAAAAACCGCAG

CATGGGATAGCGGCACCAGCACCCTGACCATTACCGTTAATAGTAAAAAAACCAAACAGCTGGTGTTTAC

CAAAGAGGATACCATTACGGTTCAGAACTATGATAGCAATGGTACGAATCTGGAAGGTAAAGCCGTTGAA

ATCACCACACTGAAAGAACTGTGTAATGCACTGAAAGGTACTAGTGCAAATAATCAGGCAGGTCAGAAAA

GCAGCGGTAGCACCCAGGCAACCACCCCGAATCTGACCTTTGAAAAGTACTCATTTAACGAGAAAGGCGA

GCTGTCAGCAAAAACCATGACCCGTGAAAATGGAACCAAACTGGAATACACGGAAATGAAATCAGATGGT

ACAGGCAAAGCCAAAGAGGTCCTGAAAAACTTCACCCTGGAAGGGAAAGTTGCCAATGATAAAGTGACAC

TGGAAGTTAAATGTGGTACAGTTACACTGAGCAAAGAAATTGCCAAATCAGGTGAAGTGACCGTGGCACT

GAATGATACAAATACCACCCGTGCCACAAAAAAAACAGGTAAATGGGATAGTAAAACGAGCACACTGACA

ATTAGTGTGAATAGCCAGAAAACGAAAAACCTGGTGTTCACGAAAGAAGATACAATCACCGTACAGAATT

ATGATTCAGCAGGCACCAACCTGGAAGGTTCACCGGCAGAAATTAAAGATCTGGCCGAACTGTGTGCAGC

CCTGAAA 23 amino acid signal sequence for lipidation from *E. coli* including a non-cleaved CSS peptide

SEQ ID NO: 30

MKATKLVLGAVILGSTLLAGCSS 6-histidine tag

SEQ ID NO: 31

HHHHHH 23 amino acid linker sequence (L2)

SEQ ID NO: 32

ANNQAGQKSSGSTQATTPNLTFE

-continued

Lip-Monomer ST1 (aa 126-273. strain B31, NP_045688.1) with
C-terminal His-tag (LEHHHHHH) and lipidated N-terminal CSS
peptide
SEQ ID NO: 33
LipCSSFNEKGEVSEKIITRADGTRLEYTGIKSDGSGKAKEVLKNFTLEGKVANDKTTLVVKCGTVTLSK

NISKSGEVSVELNDTDSSAATKKTAAWNSGTSTLTITVNSKKTKDLVFTKENTITVQQYDSNGTKLEGSA

VEITKLDEICNALKLEHHHHHH

Lip-Monomer ST2 (aa 126-273, strain K78, AJY72832.1) with
C-terminal His-tag (LEHHHHHH) and lipidated N-terminal CSS
peptide
SEQ ID NO: 34
LipCSSFNEKGELSAKTMTRENGTKLEYTEMKSDGTGKAKEVLKNFTLEGKVANDKVTLEVKCGTVTLSK

EIAKSGEVTVALNDTNTTQATKKTGAWDSKTSTLTISVNSKKTTQLVFTKQDTITVQKYDSAGTNLEGTA

VEIKTLDELCNALKLEHHHHHH

Lip-Monomer ST3 (aa 126-274, strain PBr, YP_002476925.1)
with C-terminal His-tag (LEHHHHHH) and lipidated N-terminal
CSS peptide
SEQ ID NO: 35
LipCSSFNDKGKLSEKVVTRANGTRLEYTEIKNDGSGKAKEVLKGFALEGTLTDGGETKLTVTCGTVTLS

KNISKSGEITVALNDTETTPADKKTGEWKSDTSTLTISKNSQKPKQLVFTKENTITVQNYNRAGNALEGS

PAEIKDLAELCAALKLEHHHHHH

Lip-Monomer ST4 (aa 126-273, strain PBI, YP_063283.1) with
C-terminal His-tag (LEHHHHHH) and lipidated N-terminal CSS
peptide
SEQ ID NO: 36
LipCSSFNAKGELSEKTILRANGTRLEYTEIKSDGTGKAKEVLKDFALEGTLAADKTTLKVTCGTVVLSK

HIPNSGEITVELNDSNSTQATKKTGKWDSNTSTLTISVNSKKTKNIVFTKEDTITVQKYDSAGTNLEGNA

VEIKTLDELCNALKLEHHHHHH

Lip-Monomer ST5 (aa 126-273, strain PHei, CAA56544.1) with
C-terminal His-tag (LEHHHHHH) and lipidated N-terminal CSS
peptide
SEQ ID NO: 37
LipCSSFNEKGEISEKTIVRANGTRLEYTDIKSDKTGKAKEVLKDFTLEGTLAADGKTTLKVTCGTVTLS

KNISKSGEITVALDDTDSSGNKKSGTWDSGTSTLTISKNRTKTKQLVFTKEDTITVQNYDSAGTNLEGKA

VEITTLKELCNALKLEHHHHHH

Lip-Monomer ST6 (aa 126-274, strain DK29, CAA45010) with
C-terminal His-tag (LEHHHHHH) and lipidated N-terminal
CSS peptide
SEQ ID NO: 38
LipCSSFNGKGETSEKTIVRANGTRLEYTDIKSDGSGKAKEVLKDFTLEGTLAADGKTTLKVTCGTVVLS

KNILKSGEITAALDDSDTTRATKKTGKWDSKTSTLTISVNSQKTKNLVFTKEDTITVQRYDSAGTNLEGK

AVEITTLKELCNALKLEHHHHHH

KLK peptide
SEQ ID NO: 39
KLKLLLLLKLK oligo(dIdC)$_{13}$
SEQ ID NO: 40
dIdC dIdC dIdC dIdC dIdC dIdC dIdC dIdC dIdC dIdC dIdC dIdC dIdC S3BvaHybD1: hybrid OspA C-terminal fragment; amino acids
of positions 125-176 from Borrelia valaisiana, strain
VS116, and amino acids 177-274 from Borrelia garinii,
strain PBr, with disulfide bond type 1 and T in
position 233
SEQ ID NO: 41
FNEKGEVSEKILTRSNGTTLEYSQMTDAENATKAVETLKNGIKLPGNLVGGKTKLTVTCGTVTLSKNISK

SGEITVALNDTETTPADKKTGEWKSDTSTLTISKNSQKTKQLVFTKENTITVQNYNRAGNALEGSPAEIK

DLAELCAALK

-continued

*B. valaisiana* (strain VS116) OspA, aa 125-176

SEQ ID NO: 42

FNEKGEVSEKILTRSNGTTLEYSQMTDAENATKAVETLKNGIKLPGNLVGGK

*B. garinii* (strain PBr, serotype 3) OspA aa 1 77-274, with
T in position 233, from full-length OspA (SEQ ID NO: 46)

SEQ ID NO: 43

TKLTVTCGTVTLSKNISKSGEITVALNDTETTPADKKTGEWKSDTSTLTISKNSQKTKQLVFTKENTITV

QNYNRAGNALEGSPAEIKDLAELCAALK

*B. valaisiana* (strain VS116) OspA

SEQ ID NO: 44

MKKYLLGIGLILALIACKQNVSSLDEKNSASVDLPGEMKVLVSKEKDKDGKYSLVATVDKVELKGTSDKN

NGSGTLEGVKDDKSKVKLTISDDLGETKLETFKEDGTLVSRKVNFKDKSFTEEKFNEKGEVSEKILTRSN

GTTLEYSQMTDAENATKAVETLKNGIKLPGNLVGGKTTLKITEGTVTLSKHIAKSGEVTVEINDTSSTPN

TKKTGKWDARNSTLTIIVDSKNKTKLVFTKQDTITVQSYNPAGNKLEGTAVEIKTLQELKNALK

*B. spielmanii* (strain AUS) OspA, Accession number: AAD16455

SEQ ID NO: 45

MKKYLLGIGLILALIACKQNVSGLDEKNSTSVDVPGELKVLVSKEKDKDGKYSLMATVDKLELKGTSDKN

DGSGVLEGVKADKSKVKLTISDHLSKTTFEVFKEDGKTLVSRNVNSKDKSSTKEKFNEKGELSEKTLVRA

NGTKLEYTEIKSDGTGKAKEVLKDFTLEGTLANEKATLTVKEGTVTLSKNIDKSGEVTVALNDTDSTAAT

KKTGAWDSKTSTLTITVNSKKTKDLVFTKQDTITVQKYDSAGTTLEGSAVEIKTLDELKNALK

*B. garinii* (strain PBr, OspA serotype 3) OspA with T in
position 233 (embl accession ACL34827.1)

SEQ ID NO: 46

MKKYLLGIGLILALIACKQNVSSLDEKNSVSVDLPGGMKVLVSKEKDKDGKYSLMATVEKLELKGTSDKS

NGSGVLEGEKADKSKAKLTISQDLNQTTFEIFKEDGKTLVSRKVNSKDKSSTEEKFNDKGKLSEKVVTRA

NGTRLEYTEIKNDGSGKAKEVLKGFALEGTLTDGGETKLTVTEGTVTLSKNISKSGEITVALNDTETTPA

DKKTGEWKSDTSTLTISKNSQKTKQLVFTKENTITVQNYNRAGNALEGSPAEIKDLAELKAALK

Lip-S4D1-S3hybD1-nt Coding sequence for intermediate and
final heterodimer fusion proteins of OspA serotype 4 and
OspA serotype 3 with disulfide bond type 1, *E. coli* Ipp
lipidation signal, LN1 linker sequence, serotype 3 OspA
fragment comprising amino acids 125-176 of *B. valaisiana*,
strain VS116 (SEQ ID NO: 42) and amino acids 177-274 of
*B. garinii*, strain PBr, serotype 3 (SEQ ID NO: 43)

SEQ ID NO: 47

ATGAAAGCTACTAAACTGGTACTGGGCGCGGTAATCCTGGGTTCTACTCTGCTGGCAGGTTGCTCAAGCT

TCAATGCTAAGGGCGAACTGAGCGAAAAAACGATCCTGCGTGCGAATGGCACCCGTCTGGAATACACCGA

AATCAAATCCGATGGTACGGGCAAAGCAAAGGAAGTCCTGAAAGATTTTGCTCTGGAAGGTACCCTGGCG

GCCGACAAAACCACGCTGAAGGTGACGTGCGGCACCGTGGTTCTGAGCAAACATATTCCGAACTCTGGTG

AAATCACCGTTGAACTGAACGATAGCAATTCTACGCAGGCAACCAAAAAGACGGGCAAATGGGACAGTAA

TACCTCCACGCTGACCATTTCAGTCAACTCGAAAAAGACCAAAAATATTGTGTTCACGAAGGAAGATACG

ATCACCGTTCAAAAATATGACTCCGCGGGCACCAACCTGGAAGGCAATGCCGTCGAAATCAAAACCCTGG

ATGAACTGTGTAACGCCCTGAAGGGTACTAGTGACAAAAACAATGGCTCTGGTAGCAAAGAGAAAAACAA

AGATGGCAAGTACTCATTCAACGAAAAAGGCGAAGTGAGCGAAAAAATTCTGACCCGTAGCAATGGCACC

ACCCTGGAATATAGCCAGATGACCGATGCAGAAAATGCAACCAAAGCAGTTGAAACCCTGAAAAACGGTA

TTAAACTGCCTGGTAATCTGGTTGGTGGTAAAACCAAACTGACCGTTACCTGTGGCACCGTTACCCTGAG

CAAAAACATTAGCAAAAGCGGTGAAATTACCGTGGCACTGAATGATACCGAAACCACACCGGCAGACAAA

AAAACCGGTGAATGGAAAAGCGATACCAGCACCCTGACCATTAGTAAAAATAGCCAGAAAACAAAACAGC

TGGTGTTTACCAAAGAAAACACCATTACCGTGCAGAATTATAACCGTGCAGGTAATGCACTGGAAGGTAG

TCCGGCAGAAATTAAAGATCTGGCAGAACTGTGTGCAGCCCTGAAATAA

Lip-S4D1-S3hybD1-aa: Heterodimer fusion protein of OspA
serotype 4 and OspA serotype 3, comprising amino acids
125-176 of *B. valaisiana*, strain VS116 (SEQ ID NO: 42)
and amino acids 177-274 of *B. garinii*, strain PBr,
serotype 3 (SEQ ID NO: 43) (aka S3BvaHybD1), with
disulfide bond type 1, N-terminal CSS for addition of
lipids, LN1 linker sequence, N-terminal lipidation

SEQ ID NO: 48

LipCSSFNAKGELSEKTILRANGTRLEYTEIKSDGTGKAKEVLKDFALEGTLAADKTTLKVTCGTVVLSK

HIPNSGEITVELNDSNSTQATKKTGKWDSNTSTLTISVNSKKTKNIVFTKEDTITVQKYDSAGTNLEGNA

VEIKTLDELCNALKGTSDKNNGSGSKEKNKDGKYSFNEKGEVSEKILTRSNGTTLEYSQMTDAENATKAV

ETLKNGIKLPGNLVGGKTKLTVTCGTVTLSKNISKSGEITVALNDTETTPADKKTGEWKSDTSTLTISKN

SQKTKQLVFTKENTITVQNYNRAGNALEGSPAEIKDLAELCAALK

Lip-S1D1-S2D1-nt: Coding sequence for intermediate and
final heterodimer fusion proteins of OspA serotype 1 and
OspA serotype 2 with disulfide bond type 1, *E. coli* Ipp
lipidation signal, LN1 linker sequence, aa 164-174 of
OspA serotype 1 replaced by non-hLFA-1-like sequence
NFTLEGKVAND

SEQ ID NO: 49

ATGAAAGCTACTAAACTGGTACTGGGCGCGGTAATCCTGGGTTCTACTCTGCTGGCAGGTTGCTCAAGCT

TCAACGAAAAGGGCGAAGTCAGCGAAAAAATCATTACCCGCGCAGACGGCACCCGCCTGGAATACACCGG

CATCAAATCGGACGGCAGCGGCAAAGCGAAAGAAGTTCTGAAAAACTTTACCCTGGAAGGCAAAGTCGCA

AATGATAAAACCACCCTGGTGGTGAAATGCGGCACCGTTACGCTGAGCAAAAACATTAGTAAATCCGGTG

AAGTCTCTGTGGAACTGAATGATACCGACAGCTCTGCGGCCACCAAGAAAACCGCAGCTTGGAACTCAGG

CACCTCGACGCTGACCATTACGGTTAATAGCAAGAAAACCAAAGATCTGGTCTTCACGAAAGAAAACACC

ATCACGGTGCAGCAATATGACAGCAATGGTACCAAACTGGAAGGCTCCGCTGTGGAAATCACGAAACTGG

ATGAAATCTGTAATGCTCTGAAAGGTACTAGTGACAAAAACAATGGCTCTGGTAGCAAAGAGAAAAACAA

AGATGGCAAGTACTCATTCAACGAAAAGGCGAACTGTCGGCGAAAACGATGACGCGTGAAAACGGCACC

AAACTGGAATATACGGAAATGAAAAGCGATGGCACCGGTAAAGCGAAAGAAGTTCTGAAAAACTTTACCC

TGGAAGGCAAAGTCGCCAATGACAAAGTCACCCTGGAAGTGAAATGCGGCACCGTTACGCTGTCAAAAGA

AATTGCAAAATCGGGTGAAGTGACCGTTGCTCTGAACGATACGAATACCACGCAAGCGACCAAGAAAACC

GGCGCCTGGGACAGCAAAACCTCTACGCTGACCATTAGTGTTAATAGCAAGAAAACCACGCAGCTGGTCT

TCACCAAACAAGATACGATCACCGTGCAGAAATACGACAGTGCGGGTACCAACCTGGAAGGCACGGCTGT

TGAAATCAAAACCCTGGACGAACTGTGTAACGCCCTGAAA

Lip-S1D1-S2D1-aa: Heterodimer fusion protein of OspA
serotype 1 and OspA serotype 2 with disulfide bond type 1,
N-terminal CSS for addition of lipids, LN1 linker sequence,
aa 164-174 of OspA serotype 1 replaced by non-hLFA-1-like
sequence NFTLEGKVAND, N-terminal lipidation

SEQ ID NO: 50

LipCSSFNEKGEVSEKIITRADGTRLEYTGIKSDGSGKAKEVLKNFTLEGKVANDKTTLVVKCGTVTLSK

NISKSGEVSVELNDTDSSAATKKTAAWNSGTSTLTITVNSKKTKDLVFTKENTITVQQYDSNGTKLEGSA

VEITKLDEICNALKGTSDKNNGSGSKEKNKDGKYSFNEKGELSAKTMTRENGTKLEYTEMKSDGTGKAKE

VLKNFTLEGKVANDKVTLEVKCGTVTLSKEIAKSGEVTVALNDTNTTQATKKTGAWDSKTSTLTISVNSK

KTTQLVFTKQDTITVQKYDSAGTNLEGTAVEIKTLDELCNALK

Lip-S4D1-S3D1-nt: Coding sequence for intermediate and final
heterodimer fusion proteins of OspA serotypes 4 and 3 both
with disulfide bond type 1, *E. coli* Ipp lipidation signal,
N-terminal CSS for addition of lipids, LN1 linker sequence

SEQ ID NO: 51

ATGAAAGCTACTAAACTGGTACTGGGCGCGGTAATCCTGGGTTCTACTCTGCTGGCAGGTTGCTCAAGCT

TCAATGCTAAGGGCGAACTGAGCGAAAAAACGATCCTGCGTGCGAATGGCACCCGTCTGGAATACACCGA

-continued

```
AATCAAATCCGATGGTACGGGCAAAGCAAGGAAGTCCTGAAAGATTTTGCTCTGGAAGGTACCCTGGCG

GCCGACAAAACCACGCTGAAGGTGACGTGCGGCACCGTGGTTCTGAGCAAACATATTCCGAACTCTGGTG

AAATCACCGTTGAACTGAACGATAGCAATTCTACGCAGGCAACCAAAAAGACGGGCAAATGGGACAGTAA

TACCTCCACGCTGACCATTTCAGTCAACTCGAAAAAGACCAAAAATATTGTGTTCACGAAGGAAGATACG

ATCACCGTTCAAAAATATGACTCCGCGGGCACCAACCTGGAAGGCAATGCCGTCGAAATCAAACCCTGG

ATGAACTGTGTAACGCCCTGAAGGGTACTAGTGACAAAAACAATGGCTCTGGTAGCAAAGAGAAAAACAA

AGATGGCAAGTACTCATTTAACGATAAGGGCAAACTGTCGGAAAAAGTGGTCACCCGCGCAAATGGCACC

CGCCTGGAATACACGGAAATCAAAAACGATGGTAGCGGCAAAGCGAAGGAAGTTCTGAAAGGCTTTGCCC

TGGAAGGTACCCTGACGGATGGCGGTGAAACCAAACTGACCGTGACGTGCGGCACCGTTACGCTGTCTAA

AAACATTAGCAAGTCTGGTGAAATCACGGTCGCACTGAATGATACCGAAACCACGCCGGCTGACAAAAAG

ACCGGCGAATGGAAAAGTGACACCTCCACGCTGACCATTTCAAAGAACTCGCAGAAACCGAAGCAACTGG

TCTTCACCAAAGAAAACACGATCACCGTGCAGAACTATAATCGTGCCGGTAATGCTCTGGAAGGCTCACC

GGCTGAAATCAAGGACCTGGCTGAACTGTGTGCGGCACTGAAA

Lip-S4D1-S3D1-aa: Heterodimer fusion protein of OspA
serotypes 4 and 3 both with disulfide bond type 1,
N-terminal CSS for addition of lipids, LN1 linker
sequence, N-terminal lipidation
                                                 SEQ ID NO: 52
LipCSSFNAKGELSEKTILRANGTRLEYTEIKSDGTGKAKEVLKDFALEGTLAADKTTLKVTCGTVVLSK

HIPNSGEITVELNDSNSTQATKKTGKWDSNTSTLTISVNSKKTKNIVFTKEDTITVQKYDSAGTNLEGNA

VEIKTLDELCNALKGTSDKNNGSGSKEKNKDGKYSFNDKGKLSEKVVTRANGTRLEYTEIKNDGSGKAKE

VLKGFALEGTLTDGGETKLTVTCGTVTLSKNISKSGEITVALNDTETTPADKKTGEWKSDTSTLTISKNS

QKPKQLVFTKENTITVQNYNRAGNALEGSPAEIKDLAELCAALK

Lip-S5D1-S6D1-nt: Coding sequence for intermediate and
final heterodimer fusion proteins of OspA serotypes 6
both with disulfide bond type 1, E. coli lpp lipidation
signal, N-terminal CSS for addition of lipids. LN1
linker sequence
                                                 SEQ ID NO: 53
ATGAAAGCTACTAAACTGGTACTGGGCGCGGTAATCCTGGGTTCTACTCTGCTGGCAGGTTGCTCAAGCT

TCAACGAAAAGGGCGAAATCTCAGAAAAAACCATCGTCCGCGCTAACGGCACCCGCCTGGAATACACCGA

CATCAAATCAGACAAGACCGGTAAAGCGAAGGAAGTTCTGAAAGATTTTACGCTGGAAGGTACCCTGGCA

GCAGACGGTAAAACCACGCTGAAGGTGACCTGCGGTACCGTTACGCTGTCCAAAAACATTAGTAAGTCCG

GCGAAATCACGGTCGCCCTGGATGACACCGATAGCTCTGGCAACAAAAAGAGCGGTACCTGGGATTCAGG

CACCTCGACGCTGACCATTTCTAAAAATCGTACGAAAACCAAGCAGCTGGTCTTCACGAAAGAAGATACG

ATCACCGTGCAAAACTATGACAGCGCAGGTACCAATCTGGAAGGCAAAGCTGTGGAAATTACCACGCTGA

AAGAACTGTGTAATGCTCTGAAAGGTACTAGTGACAAAAACAATGGCTCTGGTAGCAAAGAGAAAAACAA

AGATGGCAAGTACTCATTCAACGGCAAAGGTGAAACGAGCGAAAAGACCATCGTGCGTGCGAACGGTACC

CGCCTGGAATATACGGACATTAAATCGGACGGCAGCGGCAAAGCAAAGGAAGTCCTGAAAGATTTTACGC

TGGAAGGTACCCTGGCAGCAGACGGTAAAACCACGCTGAAGGTGACGTGCGGCACCGTGGTTCTGTCAAA

AAACATTCTGAAGTCGGGTGAAATCACCGCAGCTCTGGATGACAGCGATACCACGCGTGCTACGAAAAAG

ACCGGTAAATGGGATAGCAAGACCTCTACGCTGACCATTAGTGTCAACTCCCAGAAAACGAAGAATCTGG

TGTTCACCAAAGAAGATACGATCACCGTTCAACGCTATGACAGTGCGGGCACCAACCTGGAAGGCAAAGC

CGTTGAAATTACCACGCTGAAAGAACTGTGTAATGCTCTGAAA
```

```
Lip-S5D1-S6D1-aa: Heterodimer fusion protein of OspA
serotypes 6 both with disulfide bond type 1, N-terminal
CSS for addition of lipids, LN1 linker sequence,
N-terminal lipidation
                                                SEQ ID NO: 54
LipCSSFNEKGEISEKTIVRANGTRLEYTDIKSDKTGKAKEVLKDFTLEGTLAADGKTTLKVTCGTVTLS

KNISKSGEITVALDDTDSSGNKKSGTWDSGTSTLTISKNRTKTKQLVFTKEDTITVQNYDSAGTNLEGKA

VEITTLKELCNALKGTSDKNNGSGSKEKNKDGKYSFNGKGETSEKTIVRANGTRLEYTDIKSDGSGKAKE

VLKDFTLEGTLAADGKTTLKVTCGTVVLSKNILKSGEITAALDDSDTTRATKKTGKWDSKTSTLTISVNS

QKTKNLVFTKEDTITVQRYDSAGTNLEGKAVEITTLKELCNALK

S1D1
                                                SEQ ID NO: 55
FNEKGEVSEKIITRADGTRLEYTGIKSDGSGKAKEVLKNFTLEGKVANDKTTLVVKCGTVTLSKNISKSG

EVSVELNDTDSSAATKKTAAWNSGTSTLTITVNSKKTKDLVFTKENTITVQQYDSNGTKLEGSAVEITKL

DEICNALK

S2D1
                                                SEQ ID NO: 56
FNEKGELSAKTMTRENGTKLEYTEMKSDGTGKAKEVLKNFTLEGKVANDKVTLEVKCGTVTLSKEIAKSG

EVTVALNDTNTTQATKKTGAWDSKTSTLTISVNSKKTTQLVFTKQDTITVQKYDSAGTNLEGTAVEIKTL

DELCNALK

S3D1
                                                SEQ ID NO: 57
FNDKGKLSEKVVTRANGTRLEYTEIKNDGSGKAKEVLKGFALEGTLTDGGETKLTVTCGTVTLSKNISKS

GEITVALNDTETTPADKKTGEWKSDTSTLTISKNSQKTKQLVFTKENTITVQNYNRAGNALEGSPAEIKD

LAELCAALK

S4D1
                                                SEQ ID NO: 58
FNAKGELSEKTILRANGTRLEYTEIKSDGTGKAKEVLKDFALEGTLAADKTTLKVTCGTVVLSKHIPNSG

EITVELNDSNSTQATKKTGKWDSNTSTLTISVNSKKTKNIVFTKEDTITVQKYDSAGTNLEGNAVEIKTL

DELCNALK

S5D1
                                                SEQ ID NO: 59
FNEKGEISEKTIVRANGTRLEYTDIKSDKTGKAKEVLKDFTLEGTLAADGKTTLKVTCGTVTLSKNISKS

GEITVALDDTDSSGNKKSGTWDSGTSTLTISKNRTKTKQLVFTKEDTITVQNYDSAGTNLEGKAVEITTL

KELCNALK

S6D1
                                                SEQ ID NO: 60
FNGKGETSEKTIVRANGTRLEYTDIKSDGSGKAKEVLKDFTLEGTLAADGKTTLKVTCGTVVLSKNILKS

GEITAALDDSDTTRATKKTGKWDSKTSTLTISVNSQKTKNLVFTKEDTITVQRYDSAGTNLEGKAVEITT

LKELCNALK

S3BvaHybD1 (Bva)
                                                SEQ ID NO: 61
FNEKGEVSEKILTRSNGTTLEYSQMTDAENATKAVETLKNGIKLPGNLVGGKTKLTVTCGTVTLSKNISK

SGEITVALNDTETTPADKKTGEWKSDTSTLTISKNSQKTKQLVFTKENTITVQNYNRAGNALEGSPAEIK

DLAELCAALK

BvaD1 (Bva C-terminal fragment with introduced
disulfide bond)
                                                SEQ ID NO: 62
FNEKGEVSEKILTRSNGTTLEYSQMTDAENATKAVETLKNGIKLPGNLVGGKTTLKITCGTVTLSKHIAK

SGEVTVEINDTSSTPNTKKTGKWDARNSTLTIIVDSKNKTKLVFTKQDTITVQSYNPAGNKLEGTAVEIK

TLQELCNALK
```

-continued

S3BspHybD1 (Bsp): hybrid OspA C-terminal fragment;
amino acids 126-175 from Borrelia spielmanii and
amino acids 177-274 from Borrelia garinii, strain
PBr, with disulfide bond type 1 and T in position 233
SEQ ID NO: 63
FNEKGELSEKTLVRANGTKLEYTEIKSDGTGKAKEVLKDFTLEGTLANEKTKLTVTCGTVTLSKNISKSG

EITVALNDTETTPADKKTGEWKSDTSTLTISKNSQKTKQLVFTKENTITVQNYNRAGNALEGSPAEIKDL

AELCAALK

BspD1 (Bsp C-terminal fragment with introduced
disulfide bond)
SEQ ID NO: 64
FNEKGELSEKTLVRANGTKLEYTEIKSDGTGKAKEVLKDFTLEGTLANEKATLTVKCGTVTLSKNIDKSG

EVTVALNDTDSTAATKKTGAWDSKTSTLTITVNSKKTKDLVFTKQDTITVQKYDSAGTTLEGSAVEIKTL

DELCNALK

Borrelia OspA lipidation signal
SEQ ID NO: 65
MKKYLLGIGLILALIA

Borrelia OspB lipidation signal
SEQ ID NO: 66
MRLLIGFALALALIG

E. coli Ipp lipidation signal
SEQ ID NO: 67
MKATKLVLGAVILGSTLLAG

LN1 peptide linker constructed from two separate loop
regions of the N-terminal half of OspA from B. burgdorferi
s.s. strain B31 (aa 65-74 and aa 42-53, amino acid exchange
at position 53: D53S)
SEQ ID NO: 68
GTSDKNNGSGSKEKNKDGKYS Chimeric OspA Serotype1/Serotype2, N-terminal lipidation,
His-tagged, including the OspB lipidation signal sequence:
MRLLIGFALALALIG (SEQ ID NO: 66) which is cleaved during
processing
SEQ ID NO: 69
MRLLIGFALALALIGCAQKGAESIGSVSVDLPGEMKVLVSKEKDKNGKYDLIATVDKLELKGTSDKNNGS

GVLEGVKTNKSKVKLTISDDLGQTTLEVFKEDGKTLVSKKVTSKDKSSTEEKFNEKGEVSEKIITMADGT

RLEYTGIKSDGTGKAKYVLKNFTLEGKVANDKTTLEVKEGTVTLSMNISKSGEVSVELNDTDSSAATKKT

AAWNSKTSTLTISVNSKKTTQLVFTKQDTITVQKYDSAGTNLEGTAVEIKTLDELKNALKLEHHHHHH

Chimeric OspA Serotype5/Serotype3, N-terminal lipidation,
His-tagged, including the OspB lipidation signal sequence:
MRLLIGFALALALIG (SEQ ID NO: 66) which is cleaved during
processing
SEQ ID NO: 70
MRLLIGFALALALIGCAQKGAESIGSVSVDLPGGMKVLVSKEKDKNGKYSLMATVEKLELKGTSDKNNGS

GTLEGEKTNKSKVKLTIAEDLSKTTFEIFKEDGKTLVSKKVTLKDKSSTEEKFNEKGEISEKTIVMANGT

RLEYTDIKSDKTGKAKYVLKDFTLEGTLAADGKTTLKVTEGTVTLSMNISKSGEITVALDDTDSSGNKKS

GTWDSDTSTLTISKNSQKTKQLVFTKENTITVQNYNRAGNALEGSPAEIKDLAELKAALKLEHHHHHH

Chimeric OspA Serotype6/Serotype4, N-terminal lipidation,
His-tagged, including the OspB lipidation signal sequence:
MRLLIGFALALALIG (SEQ ID NO: 66) which is cleaved during
processing
SEQ ID NO: 71
MRLLIGFALALALIGCAQKGAESIGSVSVDLPGGMTVLVSKEKDKNGKYSLEATVDKLELKGTSDKNNGS

GTLEGEKTNKSKVKLTIADDLSQTKFEIFKEDAKTLVSKKVTLKDKSSTEEKFNEKGETSEKTIVMANGT

RLEYTDIKSDGSGKAKYVLKDFTLEGTLAADGKTTLKVTEGTVVLSMNILKSGEITVALDDSDTTQATKK

TGKWDSNTSTLTISVNSKKTKNIVFTKEDTITVQKYDSAGTNLEGNAVEIKTLDELKNALKLEHHHHHH

-continued

Lip-S4D1-S3BspHybD1-aa: Heterodimer fusion protein of
OspA serotype 4 and OspA serotype 3, comprising amino
acids 125-175 of *B. spielmanii*, strain A14S (SEQ ID
NO: 73) and amino acids 177-274 of *B. garinii*, strain
PBr, serotype 3 (SEQ ID NO: 43), with disulfide bond
type 1, N-terminal CSS for addition of lipids, LN1
linker sequence, N-terminal lipidation

SEQ ID NO: 72

LipCSSFNAKGELSEKTILRANGTRLEYTEIKSDGTGKAKEVLKDFALEGTLAADKTTLKVTCGTVVLSK

HIPNSGEITVELNDSNSTQATKKTGKWDSNTSTLTISVNSKKTKNIVFTKEDTITVQKYDSAGTNLEGNA

VEIKTLDELCNALKGTSDKNNGSGSKEKNKDGKYSFNEKGELSEKTLVRANGTKLEYTEIKSDGTGKAKE

VLKDFTLEGTLANEKTKLTVTCGTVTLSKNISKSGEITVALNDTETTPADKKTGEWKSDTSTLTISKNSQ

KTKQLVFTKENTITVQNYNRAGNALEGSPAEIKDLAELCAALK

*B. spielmanii* (strain A14S) OspA, aa 126-175

SEQ ID NO: 73

FNEKGELSEKTLVRANGTKLEYTEIKSDGTGKAKEVLKDFTLEGTLANEK

*B. afzelii* OspA (strain K78; OspA serotype 2)

SEQ ID NO: 74

MKKYLLGIGLILALIACKQNVSSLDEKNSASVDLPGEMKVLVSKEKDKDGKYSLKATVDKIELKGTSDKD

NGSGVLEGTKDDKSKAKLTIADDLSKTTFELFKEDGKTLVSRKVSSKDKTSTDEMFNEKGELSAKTMTRE

NGTKLEYTEMKSDGTGKAKEVLKNFTLEGKVANDKVTLEVKEGTVTLSKEIAKSGEVTVALNDTNTTQAT

KKTGAWDSKTSTLTISVNSKKTTQLVFTKQDTITVQKYDSAGTNLEGTAVEIKTLDELKNALK

Alternative His-tag

SEQ ID NO: 75

LEHHHHHH

---

The invention claimed is:

1. An immunogenic polypeptide comprising a C terminal domain of an outer surface protein A (OspA of Borrelia, characterized in that said C-terminal OspA domain comprises at least three specific OspA epitopes each from distinct Borrelia strains causing Lyme Borreliosis; wherein said C-terminal OspA domain is able to induce a protective immune response to all of said distinct Borrelia strains, wherein the C-terminal OspA domain is selected from the group consisting of SEQ ID NO: 9, SEQ ID NO: 10, SEQ ID NO: 12, SEQ ID NO: 13, and immunogenic variants thereof that have at least 95% sequence identity with any one of SEQ ID NO:9, SEQ ID NO: 10, SEQ ID NO: 12, or SEQ ID NO: 13, and wherein the three-dimensional structure of the C-terminal OspA domain is stabilized by the introduction of at least two cysteine residues that form a disulfide bond.

2. The immunogenic polypeptide according to claim 1, wherein the Borrelia strains causing Lyme Borreliosis are selected from the group of Borrelia species comprising or consisting of B. burgdorferi s.s., B. afzelii, B. bavariensis, B. garinii, B. mayonii, B. lusitaniae, B. bissettii and B. spielmanii.

3. The immunogenic polypeptide according to claim 1, wherein the at least two cysteine residues are introduced at positions between about amino acids 180 to 184 and 267 to 271, wherein the numbering is relative to the Borrelia afzelii (B. afzelii) full length OspA amino acid sequence provided by SEQ ID NO: 74.

4. The immunogenic polypeptide according to claim 1, wherein the immunogenic variants of SEQ ID NO: 9, SEQ ID NO: 10, SEQ ID NO: 12, or SEQ ID NO: 13 have at least 96%, at least 97%, at least 98%, or at least 99% sequence identity with any one of SEQ ID NO: 9; SEQ ID NO: 10, SEQ ID NO: 12, or SEQ ID NO: 13.

5. The immunogenic polypeptide of claim 1, comprising peptide (i) and peptide (ii), wherein
peptide (i) is a peptide with an amino acid sequence selected from the group consisting of SEQ ID NO: 9 and SEQ ID NO: 10, or immunogenic variant thereof, wherein said immunogenic variant has at least 95% sequence identity with SEQ ID NO: 9 or SEQ ID NO: 10; and
peptide (ii) is a peptide with an amino acid sequence selected from the group consisting of SEQ ID NO: 12 and SEQ ID NO: 13, or an immunogenic variant thereof, wherein said immunogenic variant has at least 95% sequence identity with SEQ ID NO: 12 or SEQ ID NO: 13.

6. The immunogenic polypeptide of claim 5, wherein the immunogenic polypeptide is a fusion protein, wherein peptide (i) is N-terminal to peptide (ii) or wherein peptide (ii) is N-terminal to peptide (i); and optionally wherein peptide (i) and peptide (ii) are joined by a linker sequence.

7. The immunogenic polypeptide of claim 5, further comprising an N-terminal lipidation signal sequence, optionally wherein the N-terminal lipidation signal sequence is MKATKLVLGAVILGSTLLAGCSS (SEQ ID NO: 30).

8. The immunogenic polypeptide of claim 5, wherein the fusion protein comprises the sequence of SEQ ID NO: 28 (Lip-V3-L2-V5).

9. A pharmaceutical composition comprising the immunogenic polypeptide according to claim 1 and a pharmaceutically acceptable excipient.

10. The pharmaceutical composition of claim 9, wherein the pharmaceutically acceptable excipient comprises L-methionine.

11. The pharmaceutical composition of claim 9, further comprising at least one additional antigen from *Borrelia* or a pathogen other than *Borrelia*, optionally wherein the additional antigen is from a tick-borne pathogen, especially wherein the tick-borne pathogen is selected from the group comprising *Borrelia hermsii, Borrelia parkeri, Borrelia duttoni, Borrelia miyamotoi, Borrelia turicatae, Rickettsia rickettsii, Rickettsia australis, Rickettsia conorii, Rickettsia helvetica, Rickettsia parkeri, Francisella tularensis, Anaplasma phagocytophilum, Ehrlichia sennetsu, Ehrlichia chaffeensis, Coxiella burnetii* and *Borrelia lonestari*, Tick-borne encephalitis virus (TBEV), Colorado tick fever virus (CTFV), Crimean-Congo hemorrhagic fever virus (CCHFV), Kyasanur forest disease virus (KFDV), Powassan virus, Heartland virus, Omsk Hemorrhagic Fever virus (OHFV) and *Babesia* spp., or particularly wherein the at least one additional antigen is comprised in a second vaccine composition, especially wherein the second vaccine composition is a tick-borne encephalitis vaccine, a Japanese encephalitis vaccine or a Rocky Mountain spotted fever vaccine.

12. The pharmaceutical composition of claim 9, characterized in that it further comprises an immunostimulatory substance, optionally selected from the group consisting of polycationic polymers, especially polycationic peptides, immunostimulatory oligodeoxynucleotides (ODNs), especially oligo(dIdC)$_{13}$ (SEQ ID NO: 40), peptides containing at least two LysLeuLys motifs, especially peptide KLKLLLLLKLK (SEQ ID NO: 39), neuroactive compounds, optionally human growth hormone, aluminium hydroxide or aluminium phosphate, Freund's complete or incomplete adjuvants, or combinations thereof, optionally wherein said immunostimulatory substance is a combination of either a polycationic polymer and immunostimulatory deoxynucleotides or of a peptide containing at least two LysLeuLys motifs and immunostimulatory deoxynucleotides, optionally a combination of KLKLLLLLKLK (SEQ ID NO: 39) and oligo(dIdC)$_{13}$ (SEQ ID NO: 40) or optionally wherein said polycationic peptide is polyarginine.

13. The immunogenic polypeptide of claim 5 wherein the fusion protein consists of the sequence of SEQ ID NO: 28 (Lip-V3-L2-V5).

14. The immunogenic polypeptide of claim 1 for use in a method of treating or preventing a *Borrelia* infection, optionally a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, optionally a *B. burgdorferi* s.s., *B. afzelii* or *B. garinii* infection.

15. The immunogenic polypeptide of claim 6, wherein said linker sequence comprises or consists of ANNQAGQKSSGSTQATTPNLTFE (SEQ ID NO: 32).

16. The pharmaceutical composition of claim 9, wherein the immunogenic polypeptide comprises or consists of the sequence of SEQ ID NO: 28 (Lip-V3-L2-V5).

17. The pharmaceutical composition of claim 9, wherein said pharmaceutical composition is a vaccine.

18. A method of treating or preventing *Borrelia* infection, comprising administering to a subject in need thereof the pharmaceutical composition of claim 9,
  optionally wherein the *Borrelia* infection is a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, optionally a *B. burgdorferi* s.s., *B. afzelii* or *B. garinii* infection.

19. A method of treating or preventing *Borrelia* infection, comprising administering to a subject in need thereof the immunogenic polypeptide of claim 8,
  optionally wherein the *Borrelia* infection is a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, optionally a *B. burgdorferi* s.s., *B. afzelii* or *B. garinii* infection.

20. A method of treating or preventing *Borrelia* infection, comprising administering to a subject in need thereof the immunogenic polypeptide of claim 13,
  optionally wherein the *Borrelia* infection is a *B. burgdorferi* s.s., *B. garinii, B. afzelii, B. andersoni, B. bavariensis, B. bissettii, B. valaisiana, B. lusitaniae, B. spielmanii, B. mayonii, B. japonica, B. tanukii, B. turdi* or *B. sinica* infection, optionally a *B. burgdorferi* s.s., *B. afzelii* or *B. garinii* infection.

\* \* \* \* \*

SEQUENCE LISTING

<160> NUMBER OF SEQ ID NOS: 75

<210> SEQ ID NO 1
<211> LENGTH: 268
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 1

Cys Ser Ser Phe Lys Gln Asn Val Ser Ser Leu Asp Glu Lys Asn Ser
1               5                   10                  15

Val Ser Val Asp Leu Pro Gly Glu Met Lys Val Leu Val Ser Lys Glu
            20                  25                  30

Lys Asn Lys Asp Gly Lys Tyr Asp Leu Ile Ala Thr Val Asp Lys Leu
        35                  40                  45

Glu Leu Lys Gly Thr Ser Asp Lys Asn Asn Gly Ser Gly Val Leu Glu
    50                  55                  60

Gly Val Lys Ala Asp Lys Ser Lys Val Lys Leu Thr Ile Ser Asp Asp
65                  70                  75                  80

Leu Gly Gln Thr Thr Leu Glu Val Phe Lys Glu Asp Gly Lys Thr Leu
                85                  90                  95

Val Ser Lys Lys Val Thr Ser Lys Asp Lys Ser Ser Thr Glu Glu Lys
            100                 105                 110

Phe Asn Glu Lys Gly Glu Val Ser Glu Lys Ile Ile Thr Arg Ala Asp
        115                 120                 125

```
Gly Thr Arg Leu Glu Tyr Thr Gly Ile Lys Ser Asp Gly Ser Gly Lys
    130                 135                 140

Ala Lys Glu Val Leu Lys Gly Tyr Val Leu Glu Gly Thr Leu Thr Ala
145                 150                 155                 160

Glu Lys Thr Thr Leu Val Val Lys Glu Gly Thr Val Thr Leu Ser Lys
                165                 170                 175

Asn Ile Ser Lys Ser Gly Glu Val Ser Val Glu Leu Asn Asp Thr Asp
                180                 185                 190

Ser Ser Ala Ala Thr Lys Lys Thr Ala Ala Trp Asn Ser Gly Thr Ser
            195                 200                 205

Thr Leu Thr Ile Thr Val Asn Ser Lys Lys Thr Lys Asp Leu Val Phe
    210                 215                 220

Thr Lys Glu Asn Thr Ile Thr Val Gln Gln Tyr Asp Ser Asn Gly Thr
225                 230                 235                 240

Lys Leu Glu Gly Ser Ala Val Glu Ile Thr Lys Leu Asp Glu Ile Lys
                245                 250                 255

Asn Ala Leu Lys Leu Glu His His His His His His
                260                 265
```

<210> SEQ ID NO 2
<211> LENGTH: 268
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 2

```
Cys Ser Ser Phe Lys Gln Asn Val Ser Ser Leu Asp Glu Lys Asn Ser
1               5                   10                  15

Ala Ser Val Asp Leu Pro Gly Glu Met Lys Val Leu Val Ser Lys Glu
                20                  25                  30

Lys Asp Lys Asp Gly Lys Tyr Ser Leu Lys Ala Thr Val Asp Lys Ile
            35                  40                  45

Glu Leu Lys Gly Thr Ser Asp Lys Asp Asn Gly Ser Gly Val Leu Glu
    50                  55                  60

Gly Thr Lys Asp Asp Lys Ser Lys Ala Lys Leu Thr Ile Ala Asp Asp
65                  70                  75                  80

Leu Ser Lys Thr Thr Phe Glu Leu Phe Lys Glu Asp Gly Lys Thr Leu
                85                  90                  95

Val Ser Arg Lys Val Ser Ser Lys Asp Lys Thr Ser Thr Asp Glu Met
                100                 105                 110

Phe Asn Glu Lys Gly Glu Leu Ser Ala Lys Thr Met Thr Arg Glu Asn
            115                 120                 125

Gly Thr Lys Leu Glu Tyr Thr Glu Met Lys Ser Asp Gly Thr Gly Lys
    130                 135                 140

Ala Lys Glu Val Leu Lys Asn Phe Thr Leu Glu Gly Lys Val Ala Asn
145                 150                 155                 160

Asp Lys Val Thr Leu Glu Val Lys Glu Gly Thr Val Thr Leu Ser Lys
                165                 170                 175

Glu Ile Ala Lys Ser Gly Glu Val Thr Val Ala Leu Asn Asp Thr Asn
            180                 185                 190

Thr Thr Gln Ala Thr Lys Lys Thr Gly Ala Trp Asp Ser Lys Thr Ser
    195                 200                 205
```

Thr Leu Thr Ile Ser Val Asn Ser Lys Lys Thr Thr Gln Leu Val Phe
    210                 215                 220

Thr Lys Gln Asp Thr Ile Thr Val Gln Lys Tyr Asp Ser Ala Gly Thr
225                 230                 235                 240

Asn Leu Glu Gly Thr Ala Val Glu Ile Lys Thr Leu Asp Glu Leu Lys
            245                 250                 255

Asn Ala Leu Lys Leu Glu His His His His His
            260                 265

<210> SEQ ID NO 3
<211> LENGTH: 269
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 3

Cys Ser Ser Phe Lys Gln Asn Val Ser Ser Leu Asp Glu Lys Asn Ser
1               5                   10                  15

Val Ser Val Asp Leu Pro Gly Gly Met Lys Val Leu Val Ser Lys Glu
            20                  25                  30

Lys Asp Lys Asp Gly Lys Tyr Ser Leu Met Ala Thr Val Glu Lys Leu
        35                  40                  45

Glu Leu Lys Gly Thr Ser Asp Lys Ser Asn Gly Ser Gly Val Leu Glu
    50                  55                  60

Gly Glu Lys Ala Asp Lys Ser Lys Ala Lys Leu Thr Ile Ser Gln Asp
65                  70                  75                  80

Leu Asn Gln Thr Thr Phe Glu Ile Phe Lys Glu Asp Gly Lys Thr Leu
                85                  90                  95

Val Ser Arg Lys Val Asn Ser Lys Asp Lys Ser Ser Thr Glu Glu Lys
            100                 105                 110

Phe Asn Asp Lys Gly Lys Leu Ser Glu Lys Val Val Thr Arg Ala Asn
        115                 120                 125

Gly Thr Arg Leu Glu Tyr Thr Glu Ile Lys Asn Asp Gly Ser Gly Lys
    130                 135                 140

Ala Lys Glu Val Leu Lys Gly Phe Ala Leu Glu Gly Thr Leu Thr Asp
145                 150                 155                 160

Gly Gly Glu Thr Lys Leu Thr Val Thr Glu Gly Thr Val Thr Leu Ser
                165                 170                 175

Lys Asn Ile Ser Lys Ser Gly Glu Ile Thr Val Ala Leu Asn Asp Thr
            180                 185                 190

Glu Thr Thr Pro Ala Asp Lys Lys Thr Gly Glu Trp Lys Ser Asp Thr
        195                 200                 205

Ser Thr Leu Thr Ile Ser Lys Asn Ser Gln Lys Thr Lys Gln Leu Val
    210                 215                 220

Phe Thr Lys Glu Asn Thr Ile Thr Val Gln Asn Tyr Asn Arg Ala Gly
225                 230                 235                 240

Asn Ala Leu Glu Gly Ser Pro Ala Glu Ile Lys Asp Leu Ala Glu Leu
                245                 250                 255

Lys Ala Ala Leu Lys Leu Glu His His His His His
            260                 265

<210> SEQ ID NO 4
<211> LENGTH: 268

<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 4

Cys Ser Ser Phe Lys Gln Asn Val Ser Ser Leu Asp Glu Lys Asn Ser
1               5                   10                  15

Val Ser Val Asp Leu Pro Gly Glu Met Lys Val Leu Val Ser Lys Glu
            20                  25                  30

Lys Asp Lys Asp Gly Lys Tyr Ser Leu Met Ala Thr Val Asp Lys Leu
        35                  40                  45

Glu Leu Lys Gly Thr Ser Asp Lys Ser Asn Gly Ser Gly Thr Leu Glu
    50                  55                  60

Gly Glu Lys Ser Asp Lys Ser Lys Ala Lys Leu Thr Ile Ser Glu Asp
65                  70                  75                  80

Leu Ser Lys Thr Thr Phe Glu Ile Phe Lys Glu Asp Gly Lys Thr Leu
                85                  90                  95

Val Ser Lys Lys Val Asn Ser Lys Asp Lys Ser Ser Ile Glu Glu Lys
            100                 105                 110

Phe Asn Ala Lys Gly Glu Leu Ser Glu Lys Thr Ile Leu Arg Ala Asn
        115                 120                 125

Gly Thr Arg Leu Glu Tyr Thr Glu Ile Lys Ser Asp Gly Thr Gly Lys
    130                 135                 140

Ala Lys Glu Val Leu Lys Asp Phe Ala Leu Glu Gly Thr Leu Ala Ala
145                 150                 155                 160

Asp Lys Thr Thr Leu Lys Val Thr Glu Gly Thr Val Val Leu Ser Lys
                165                 170                 175

His Ile Pro Asn Ser Gly Glu Ile Thr Val Glu Leu Asn Asp Ser Asn
            180                 185                 190

Ser Thr Gln Ala Thr Lys Lys Thr Gly Lys Trp Asp Ser Asn Thr Ser
        195                 200                 205

Thr Leu Thr Ile Ser Val Asn Ser Lys Lys Thr Lys Asn Ile Val Phe
    210                 215                 220

Thr Lys Glu Asp Thr Ile Thr Val Gln Lys Tyr Asp Ser Ala Gly Thr
225                 230                 235                 240

Asn Leu Glu Gly Asn Ala Val Glu Ile Lys Thr Leu Asp Glu Leu Lys
                245                 250                 255

Asn Ala Leu Lys Leu Glu His His His His His His
            260                 265

<210> SEQ ID NO 5
<211> LENGTH: 268
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 5

Cys Ser Ser Phe Lys Gln Asn Val Ser Ser Leu Asp Glu Lys Asn Ser
1               5                   10                  15

Val Ser Val Asp Leu Pro Gly Gly Met Lys Val Leu Val Ser Lys Glu
            20                  25                  30

Lys Asp Lys Asp Gly Lys Tyr Ser Leu Met Ala Thr Val Glu Lys Leu
            35                  40                  45

Glu Leu Lys Gly Thr Ser Asp Lys Asn Asn Gly Ser Gly Thr Leu Glu
 50                  55                  60

Gly Glu Lys Thr Asp Lys Ser Lys Val Lys Leu Thr Ile Ala Glu Asp
 65                  70                  75                  80

Leu Ser Lys Thr Thr Phe Glu Ile Phe Lys Glu Asp Gly Lys Thr Leu
                85                  90                  95

Val Ser Lys Lys Val Thr Leu Lys Asp Lys Ser Ser Thr Glu Glu Lys
                100                 105                 110

Phe Asn Glu Lys Gly Glu Ile Ser Glu Lys Thr Ile Val Arg Ala Asn
            115                 120                 125

Gly Thr Arg Leu Glu Tyr Thr Asp Ile Lys Ser Asp Lys Thr Gly Lys
130                 135                 140

Ala Lys Glu Val Leu Lys Asp Phe Thr Leu Glu Gly Thr Leu Ala Ala
145                 150                 155                 160

Asp Gly Lys Thr Thr Leu Lys Val Thr Glu Gly Thr Val Thr Leu Ser
                165                 170                 175

Lys Asn Ile Ser Lys Ser Gly Glu Ile Thr Val Ala Leu Asp Asp Thr
            180                 185                 190

Asp Ser Ser Gly Asn Lys Lys Ser Gly Thr Trp Asp Ser Gly Thr Ser
            195                 200                 205

Thr Leu Thr Ile Ser Lys Asn Arg Thr Lys Thr Lys Gln Leu Val Phe
210                 215                 220

Thr Lys Glu Asp Thr Ile Thr Val Gln Asn Tyr Asp Ser Ala Gly Thr
225                 230                 235                 240

Asn Leu Glu Gly Lys Ala Val Glu Ile Thr Thr Leu Lys Glu Leu Lys
                245                 250                 255

Asn Ala Leu Lys Leu Glu His His His His His
            260                 265

<210> SEQ ID NO 6
<211> LENGTH: 269
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 6

Cys Ser Ser Phe Lys Gln Asn Val Ser Ser Leu Asp Glu Lys Asn Ser
 1               5                  10                  15

Val Ser Val Asp Leu Pro Gly Gly Met Thr Val Leu Val Ser Lys Glu
                20                  25                  30

Lys Asp Lys Asp Gly Lys Tyr Ser Leu Glu Ala Thr Val Asp Lys Leu
            35                  40                  45

Glu Leu Lys Gly Thr Ser Asp Lys Asn Asn Gly Ser Gly Thr Leu Glu
 50                  55                  60

Gly Glu Lys Thr Asp Lys Ser Lys Val Lys Ser Thr Ile Ala Asp Asp
 65                  70                  75                  80

Leu Ser Gln Thr Lys Phe Glu Ile Phe Lys Glu Asp Gly Lys Thr Leu
                85                  90                  95

Val Ser Lys Lys Val Thr Leu Lys Asp Lys Ser Ser Thr Glu Glu Lys
                100                 105                 110

```
Phe Asn Gly Lys Gly Glu Thr Ser Glu Lys Thr Ile Val Arg Ala Asn
            115                 120                 125

Gly Thr Arg Leu Glu Tyr Thr Asp Ile Lys Ser Asp Gly Ser Gly Lys
        130                 135                 140

Ala Lys Glu Val Leu Lys Asp Phe Thr Leu Glu Gly Thr Leu Ala Ala
145                 150                 155                 160

Asp Gly Lys Thr Thr Leu Lys Val Thr Glu Gly Thr Val Val Leu Ser
                165                 170                 175

Lys Asn Ile Leu Lys Ser Gly Glu Ile Thr Ala Ala Leu Asp Asp Ser
            180                 185                 190

Asp Thr Thr Arg Ala Thr Lys Lys Thr Gly Lys Trp Asp Ser Lys Thr
            195                 200                 205

Ser Thr Leu Thr Ile Ser Val Asn Ser Gln Lys Thr Lys Asn Leu Val
        210                 215                 220

Phe Thr Lys Glu Asp Thr Ile Thr Val Gln Arg Tyr Asp Ser Ala Gly
225                 230                 235                 240

Thr Asn Leu Glu Gly Lys Ala Val Glu Ile Thr Thr Leu Lys Glu Leu
                245                 250                 255

Lys Asn Ala Leu Lys Leu Glu His His His His His
            260                 265

<210> SEQ ID NO 7
<211> LENGTH: 148
<212> TYPE: PRT
<213> ORGANISM: Borrelia afzelii

<400> SEQUENCE: 7

Phe Asn Glu Lys Gly Glu Leu Ser Ala L

Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Val Ala Ala
        35                  40                  45

Asp Lys Val Thr Leu Lys Val Thr Glu Gly Thr Val Thr Leu Ser Lys
    50                  55                  60

His Ile Pro Asn Ser Gly Glu Ile Thr Val Glu Leu Asp Asp Thr Asp
65                  70                  75                  80

Ser Ser Ala Ala Thr Lys Lys Thr Ala Ala Trp Asp Ser Asn Thr Ser
            85                  90                  95

Thr Leu Thr Ile Thr Val Asn Ser Lys Lys Thr Lys Asn Leu Val Phe
            100                 105                 110

Thr Lys Glu Asp Thr Ile Cys Val Gln Asn Tyr Asp Ser Asn Gly Thr
            115                 120                 125

Asn Leu Glu Gly Lys Cys Val Glu Ile Thr Thr Leu Lys Glu Leu Lys
            130                 135                 140

Asn Ala Leu Lys
145

<210> SEQ ID NO 9
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 9

Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Val Ala Ala
        35                  40                  45

Asp Lys Val Thr Leu Lys Val Thr Cys Gly Thr Val Thr Leu Ser Lys
    50                  55                  60

His Ile Pro Asn Ser Gly Glu Ile Thr Val Glu Leu Asp Asp Thr Asp
65                  70                  75                  80

Ser Ser Ala Ala Thr Lys Lys Thr Ala Ala Trp Asp Ser Asn Thr Ser
            85                  90                  95

Thr Leu Thr Ile Thr Val Asn Ser Lys Lys Thr Lys Asn Leu Val Phe
            100                 105                 110

Thr Lys Glu Asp Thr Ile Thr Val Gln Asn Tyr Asp Ser Asn Gly Thr
            115                 120                 125

Asn Leu Glu Gly Lys Ala Val Glu Ile Thr Thr Leu Lys Glu Leu Cys
            130                 135                 140

Asn Ala Leu Lys
145

<210> SEQ ID NO 10
<211> LENGTH: 149
<212> TYPE: PRT
<213> ORGANISM: Artificial Sequence
<220> FEATURE:
<223> OTHER INFORMATION: Synthetic Polypeptide

<400> SEQUENCE: 10

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Val Ala Ala
            35                  40                  45

Asp Gly Lys Val Thr Leu Lys Val Thr Cys Gly Thr Val Thr Leu Ser
        50                  55                  60

Lys Asn Ile Ser Lys Ser Gly Glu Ile Thr Val Ala Leu Asp Asp Thr
65                  70                  75                  80

Asp Ser Ser Ala Ala Thr Lys Lys Thr Ala Ala Trp Asp Ser Gly Thr
            85                  90                  95

Ser Thr Leu Thr Ile Thr Val Asn Ser Lys Lys Thr Lys Gln Leu Val
            100                 105                 110

Phe Thr Lys Glu Asp Thr Ile Thr Val Gln Asn Tyr Asp Ser Asn Gly
            115                 120                 125

Thr Asn Leu Glu Gly Lys Ala Val Glu Ile Thr Thr Leu Lys Glu Leu
            130                 135                 140

Cys Asn Ala Leu Lys
145

<210> SEQ ID NO 11
<211> LENGTH: 149
<212> TYPE: PRT
<213> ORGANISM: Artificial Sequence
<220> FEATURE:
<223> OTHER INFORMATION: Synthetic Polypeptide

<400> SEQUENCE: 11

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Val Ala Ala
            35                  40                  45

Asp Gly Lys Val Thr Leu Lys Val Thr Glu Gly Thr Val Thr Leu Ser
        50                  55                  60

Lys Asn Ile Ser Lys Ser Gly Glu Ile Thr Val Ala Leu Asp Asp Thr
65                  70                  75                  80

Asp Ser Ser Ala Ala Thr Lys Lys Thr Ala Ala Trp Asp Ser Gly Thr
            85                  90                  95

Ser Thr Leu Thr Ile Thr Val Asn Ser Lys Lys Thr Lys Gln Leu Val
            100                 105                 110

Phe Thr Lys Glu Asp Thr Ile Cys Val Gln Asn Tyr Asp Ser Asn Gly
            115                 120                 125

Thr Asn Leu Glu Gly Lys Cys Val Glu Ile Thr Thr Leu Lys Glu Leu
            130                 135                 140

Lys Asn Ala Leu Lys
145

<210> SEQ ID NO 12
<211> LENGTH: 148
<212> TYPE: PRT
<213> ORGANISM: Artificial Sequence
<220> FEATURE:
<223> OTHER INFORMATION: Synthetic Polypeptide

```
<400> SEQUENCE: 12

Phe Asn Glu Lys Gly Glu Leu Ser Ala Lys Thr Met Thr Arg Glu Asn
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Cys Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Arg Ala Thr Lys Lys Thr Gly Lys Trp Asp Ser Lys Thr Ser
                85                  90                  95

Thr Leu Thr Ile Ser Val Asn Ser Gln Lys Thr Lys Asn Leu Val Phe
            100                 105                 110

Thr Lys Glu Asp Thr Ile Thr Val Gln Asn Tyr Asp Ser Ala Gly Thr
        115                 120                 125

Asn Leu Glu Gly Ser Pro Ala Glu Ile Lys Asp Leu Ala Glu Leu Cys
    130                 135                 140

Ala Ala Leu Lys
145

<210> SEQ ID NO 13
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 13

Phe Asn Glu Lys Gly Glu Leu Ser Ala Lys Thr Met Thr Arg Glu Asn
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Cys Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Lys Asn Leu Val Phe
            100                 105                 110

Thr Lys Glu Asp Thr Ile Thr Val Gln Asn Tyr Asp Ser Ala Gly Thr
        115                 120                 125

Asn Leu Glu Gly Ser Pro Ala Glu Ile Lys Asp Leu Ala Glu Leu Cys
    130                 135                 140

Ala Ala Leu Lys
145

<210> SEQ ID NO 14
<211> LENGTH: 157
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: LIPID
<222> LOCATION: (1)..(1)

<400> SEQUENCE: 14

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Val Ala Ala Asp Lys Val Thr Leu Lys Val Thr Glu Gly Thr Val Thr
50                  55                  60

Leu Ser Lys His Ile Pro Asn Ser Gly Glu Ile Thr Val Glu Leu Asp
65                  70                  75                  80

Asp Thr Asp Ser Ser Ala Ala Thr Lys Lys Thr Ala Ala Trp Asp Ser
                85                  90                  95

Asn Thr Ser Thr Leu Thr Ile Thr Val Asn Ser Lys Lys Thr Lys Asn
            100                 105                 110

Leu Val Phe Thr Lys Glu Asp Thr Ile Cys Val Gln Asn Tyr Asp Ser
        115                 120                 125

Asn Gly Thr Asn Leu Glu Gly Lys Cys Val Glu Ile Thr Thr Leu Lys
    130                 135                 140

Glu Leu Lys Asn Ala Leu Lys His His His His His His
145                 150                 155

<210> SEQ ID NO 15
<211> LENGTH: 157
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 15

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Val Ala Ala Asp Lys Val Thr Leu Lys Val Thr Cys Gly Thr Val Thr
50                  55                  60

Leu Ser Lys His Ile Pro Asn Ser Gly Glu Ile Thr Val Glu Leu Asp
65                  70                  75                  80

Asp Thr Asp Ser Ser Ala Ala Thr Lys Lys Thr Ala Ala Trp Asp Ser
                85                  90                  95

Asn Thr Ser Thr Leu Thr Ile Thr Val Asn Ser Lys Lys Thr Lys Asn
            100                 105                 110

Leu Val Phe Thr Lys Glu Asp Thr Ile Thr Val Gln Asn Tyr Asp Ser
        115                 120                 125

Asn Gly Thr Asn Leu Glu Gly Lys Ala Val Glu Ile Thr Thr Leu Lys
    130                 135                 140

Glu Leu Cys Asn Ala Leu Lys His His His His His His
145                 150                 155
```

```
<210> SEQ ID NO 16
<211> LENGTH: 158
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 16

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Val Ala Ala Asp Gly Lys Val Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Lys Thr Lys
            100                 105                 110

Gln Leu Val Phe Thr Lys Glu Asp Thr Ile Thr Val Gln Asn Tyr Asp
        115                 120                 125

Ser Asn Gly Thr Asn Leu Glu Gly Lys Ala Val Glu Ile Thr Thr Leu
    130                 135                 140

Lys Glu Leu Cys Asn Ala Leu Lys His His His His His His
145                 150                 155

<210> SEQ ID NO 17
<211> LENGTH: 158
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 17

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Val Ala Ala Asp Gly Lys Val Thr Leu Lys Val Thr Glu Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Lys Thr Lys
            100                 105                 110

Gln Leu Val Phe Thr Lys Glu Asp Thr Ile Cys Val Gln Asn Tyr Asp
        115                 120                 125
```

```
Ser Asn Gly Thr Asn Leu Glu Gly Lys Cys Val Glu Ile Thr Thr Leu
            130                 135                 140

Lys Glu Leu Lys Asn Ala Leu Lys His His His His His His
145                 150                 155
```

<210> SEQ ID NO 18
<211> LENGTH: 157
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 18

```
Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Arg Ala Thr Lys Lys Thr Gly Lys Trp Asp Ser
                85                  90                  95

Lys Thr Ser Thr Leu Thr Ile Ser Val Asn Ser Gln Lys Thr Lys Asn
            100                 105                 110

Leu Val Phe Thr Lys Glu Asp Thr Ile Thr Val Gln Asn Tyr Asp Ser
        115                 120                 125

Ala Gly Thr Asn Leu Glu Gly Ser Pro Ala Glu Ile Lys Asp Leu Ala
    130                 135                 140

Glu Leu Cys Ala Ala Leu Lys His His His His His His
145                 150                 155
```

<210> SEQ ID NO 19
<211> LENGTH: 157
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 19

```
Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
```

```
                    85                  90                  95

Lys Thr Ser Thr Leu Thr Ile Ser Val Asn Ser Lys Lys Thr Lys Asn
            100                 105                 110

Leu Val Phe Thr Lys Glu Asp Thr Ile Thr Val Gln Asn Tyr Asp Ser
            115                 120                 125

Ala Gly Thr Asn Leu Glu Gly Ser Pro Ala Glu Ile Lys Asp Leu Ala
        130                 135                 140

Glu Leu Cys Ala Ala Leu Lys His His His His His His
145                 150                 155

<210> SEQ ID NO 20
<211> LENGTH: 151
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 20

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Val Ala Ala Asp Lys Val Thr Leu Lys Val Thr Glu Gly Thr Val Thr
    50                  55                  60

Leu Ser Lys His Ile Pro Asn Ser Gly Glu Ile Thr Val Glu Leu Asp
65                  70                  75                  80

Asp Thr Asp Ser Ser Ala Ala Thr Lys Lys Thr Ala Ala Trp Asp Ser
                85                  90                  95

Asn Thr Ser Thr Leu Thr Ile Thr Val Asn Ser Lys Lys Thr Lys Asn
            100                 105                 110

Leu Val Phe Thr Lys Glu Asp Thr Ile Cys Val Gln Asn Tyr Asp Ser
            115                 120                 125

Asn Gly Thr Asn Leu Glu Gly Lys Cys Val Glu Ile Thr Thr Leu Lys
        130                 135                 140

Glu Leu Lys Asn Ala Leu Lys
145                 150

<210> SEQ ID NO 21
<211> LENGTH: 151
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 21

Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45
```

Val Ala Asp Lys Val Thr Leu Lys Val Thr Cys Gly Thr Val Thr
    50                  55                  60

Leu Ser Lys His Ile Pro Asn Ser Gly Glu Ile Thr Val Glu Leu Asp
65                  70                  75                  80

Asp Thr Asp Ser Ser Ala Ala Thr Lys Lys Thr Ala Ala Trp Asp Ser
                85                  90                  95

Asn Thr Ser Thr Leu Thr Ile Thr Val Asn Ser Lys Lys Thr Lys Asn
                100                 105                 110

Leu Val Phe Thr Lys Glu Asp Thr Ile Thr Val Gln Asn Tyr Asp Ser
            115                 120                 125

Asn Gly Thr Asn Leu Glu Gly Lys Ala Val Glu Ile Thr Thr Leu Lys
130                 135                 140

Glu Leu Cys Asn Ala Leu Lys
145                 150

<210> SEQ ID NO 22
<211> LENGTH: 152
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 22

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
                20                  25                  30

Thr Gly Lys Ala Lys Glu Val Leu Lys Asp Phe Ala Leu Glu Gly Thr
            35                  40                  45

Val Ala Ala Asp Gly Lys Val Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Lys Thr Lys
                100                 105                 110

Gln Leu Val Phe Thr Lys Glu Asp Thr Ile Thr Val Gln Asn Tyr Asp
            115                 120                 125

Ser Asn Gly Thr Asn Leu Glu Gly Lys Ala Val Glu Ile Thr Thr Leu
130                 135                 140

Lys Glu Leu Cys Asn Ala Leu Lys
145                 150

<210> SEQ ID NO 23
<211> LENGTH: 152
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 23

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
                20                  25                  30

Thr Gly Lys Ala Lys Glu Val Leu Lys Asp Phe Ala Leu Glu Gly Thr
            35                  40                  45

Val Ala Asp Gly Lys Val Thr Leu Lys Val Thr Glu Gly Thr Val
 50                  55                  60

Thr Leu Ser Lys Asn Ile Ser Lys Ser Gly Glu Ile Thr Val Ala Leu
 65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Thr Lys
            100                 105                 110

Gln Leu Val Phe Thr Lys Glu Asp Thr Ile Cys Val Gln Asn Tyr Asp
                115                 120                 125

Ser Asn Gly Thr Asn Leu Glu Gly Lys Cys Val Glu Ile Thr Thr Leu
            130                 135                 140

Lys Glu Leu Lys Asn Ala Leu Lys
145                 150

<210> SEQ ID NO 24
<211> LENGTH: 151
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 24

Cys Ser Ser Phe Asn Glu Lys Gly Glu Leu Ser Ala Lys Thr Met Thr
 1               5                  10                  15

Arg Glu Asn Gly Thr Lys Leu Glu Tyr Thr Glu Met Lys Ser Asp Gly
                20                  25                  30

Thr Gly Lys Ala Lys Glu Val Leu Lys Asn Phe Thr Leu Glu Gly Lys
            35                  40                  45

Val Ala Asn Asp Lys Val Thr Leu Glu Val Lys Cys Gly Thr Val Thr
 50                  55                  60

Leu Ser Lys Glu Ile Ala Lys Ser Gly Glu Val Thr Val Ala Leu Asn
 65                  70                  75                  80

Asp Thr Asn Thr Thr Arg Ala Thr Lys Lys Thr Gly Lys Trp Asp Ser
                85                  90                  95

Lys Thr Ser Thr Leu Thr Ile Ser Val Asn Ser Gln Lys Thr Lys Asn
            100                 105                 110

Leu Val Phe Thr Lys Glu Asp Thr Ile Thr Val Gln Asn Tyr Asp Ser
                115                 120                 125

Ala Gly Thr Asn Leu Glu Gly Ser Pro Ala Glu Ile Lys Asp Leu Ala
            130                 135                 140

Glu Leu Cys Ala Ala Leu Lys
145                 150

<210> SEQ ID NO 25
<211> LENGTH: 151
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: LIPID
<222> LOCATION: (1)..(1)

<400> SEQUENCE: 25

Cys Ser Ser Phe Asn Glu Lys Gly Glu Leu Ser Ala Lys Thr Met Thr
1               5                   10                  15

Arg Glu Asn Gly Thr Lys Leu Glu Tyr Thr Glu Met Lys Ser Asp Gly
            20                  25                  30

Thr Gly Lys Ala Lys Glu Val Leu Lys Asn Phe Thr Leu Glu Gly Lys
        35                  40                  45

Val Ala Asn Asp Lys Val Thr Leu Glu Val Lys Cys Gly Thr Val Thr
    50                  55                  60

Leu Ser Lys Glu Ile Ala Lys Ser Gly Glu Val Thr Val Ala Leu Asn
65                  70                  75                  80

Asp Thr Asn Thr Thr Gln Ala Thr Lys Lys Thr Gly Ala Trp Asp Ser
                85                  90                  95

Lys Thr Ser Thr Leu Thr Ile Ser Val Asn Ser Lys Lys Thr Lys Asn
            100                 105                 110

Leu Val Phe Thr Lys Glu Asp Thr Ile Thr Val Gln Asn Tyr Asp Ser
        115                 120                 125

Ala Gly Thr Asn Leu Glu Gly Ser Pro Ala Glu Ile Lys Asp Leu Ala
    130                 135                 140

Glu Leu Cys Ala Ala Leu Lys
145                 150

<210> SEQ ID NO 26
<211> LENGTH: 337
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 26

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Val Ala Ala Asp Gly Lys Val Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Lys Thr Lys
            100                 105                 110

Gln Leu Val Phe Thr Lys Glu Asp Thr Ile Thr Val Gln Asn Tyr Asp
        115                 120                 125

Ser Asn Gly Thr Asn Leu Glu Gly Lys Ala Val Glu Ile Thr Thr Leu
    130                 135                 140

Lys Glu Leu Cys Asn Ala Leu Lys Gly Thr Ser Ala Asn Asn Gln Ala
145                 150                 155                 160

Gly Gln Lys Ser Ser Gly Ser Thr Gln Ala Thr Thr Pro Asn Leu Thr
```

```
                    165                 170                 175
Phe Glu Lys Tyr Ser Phe Asn Glu Lys Gly Glu Leu Ser Ala Lys Thr
                180                 185                 190

Met Thr Arg Glu Asn Gly Thr Lys Leu Glu Tyr Thr Glu Met Lys Ser
            195                 200                 205

Asp Gly Thr Gly Lys Ala Lys Glu Val Leu Lys Asn Phe Thr Leu Glu
        210                 215                 220

Gly Lys Val Ala Asn Asp Lys Val Thr Leu Glu Val Lys Cys Gly Thr
225                 230                 235                 240

Val Thr Leu Ser Lys Glu Ile Ala Lys Ser Gly Glu Val Thr Val Ala
                245                 250                 255

Leu Asn Asp Thr Asn Thr Thr Arg Ala Thr Lys Lys Thr Gly Lys Trp
            260                 265                 270

Asp Ser Lys Thr Ser Thr Leu Thr Ile Ser Val Asn Ser Gln Lys Thr
        275                 280                 285

Lys Asn Leu Val Phe Thr Lys Glu Asp Thr Ile Thr Val Gln Asn Tyr
    290                 295                 300

Asp Ser Ala Gly Thr Asn Leu Glu Gly Ser Pro Ala Glu Ile Lys Asp
305                 310                 315                 320

Leu Ala Glu Leu Cys Ala Ala Leu Lys Leu Glu His His His His His
                325                 330                 335

His
```

<210> SEQ ID NO 27
<211> LENGTH: 1011
<212> TYPE: DNA
<213> ORGANISM: Artificial Sequence
<220> FEATURE:
<223> OTHER INFORMATION: Synthetic Polynucleotide

<400> SEQUENCE: 27

```
tgctcaagct tcaatgcaaa aggtgaactg agcgaaaaaa ccattctgcg tgcaaatggc      60
acccgtctgg aatataccga aatcaaaagt gatggcaccg gtaaagcaaa agaagtgctg     120
aaagattttg cactggaagg caccgttgca gcagatggta agttacccct gaaagttacc     180
tgtggcaccg tgaccctgag caaaaacatt agcaaaagcg gtgaaattac cgttgccctg     240
gatgataccg atagcagcgc agcaaccaaa aaaaccgcag catgggatag cgcaccagc      300
accctgacca ttaccgttaa tagtaaaaaa accaaacagc tggtgtttac aaagaggat      360
accattacgg ttcagaacta tgatagcaat ggtacgaatc tggaaggtaa agccgttgaa     420
atcaccacac tgaaagaact gtgtaatgca ctgaaaggta ctagtgcaaa taatcaggca     480
ggtcagaaaa gcagcggtag cacccaggca accaccccga atctgacctt tgaaaagtac     540
tcatttaacg agaaaggcga gctgtcagca aaaaccatga cccgtgaaaa tggaaccaaa     600
ctggaataca cggaaatgaa atcagatggt acaggcaaag ccaaagaggt cctgaaaaac     660
ttcaccctgg aagggaaagt tgccaatgat aaagtgacac tggaagttaa atgtggtaca     720
gttacactga gcaaagaaat tgccaaatca ggtgaagtga ccgtggcact gaatgataca     780
aataccaccc gtgccacaaa aaaaacaggt aaatgggata gtaaaacgag cacactgaca     840
attagtgtga atagccagaa aacgaaaaac ctggtgttca gaaagaaga tacaatcacc      900
gtacagaatt atgattcagc aggcaccaac ctggaaggtt caccggcaga aattaaagat     960
ctggccgaac tgtgtgcagc cctgaaactc gagcaccacc accaccacca c             1011
```

```
<210> SEQ ID NO 28
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 28

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45

Val Ala Ala Asp Gly Lys Val Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Ala Ala Thr Lys Lys Thr Ala Ala Trp Asp
                85                  90                  95

Ser Gly Thr Ser Thr Leu Thr Ile Thr Val Asn Ser Lys Lys Thr Lys
            100                 105                 110

Gln Leu Val Phe Thr Lys Glu Asp Thr Ile Thr Val Gln Asn Tyr Asp
        115                 120                 125

Ser Asn Gly Thr Asn Leu Glu Gly Lys Ala Val Glu Ile Thr Thr Leu
    130                 135                 140

Lys Glu Leu Cys Asn Ala Leu Lys Gly Thr Ser Ala Asn Asn Gln Ala
145                 150                 155                 160

Gly Gln Lys Ser Ser Gly Ser Thr Gln Ala Thr Thr Pro Asn Leu Thr
                165                 170                 175

Phe Glu Lys Tyr Ser Phe Asn Glu Lys Gly Glu Leu Ser Ala Lys Thr
            180                 185                 190

Met Thr Arg Glu Asn Gly Thr Lys Leu Glu Tyr Thr Glu Met Lys Ser
        195                 200                 205

Asp Gly Thr Gly Lys Ala Lys Glu Val Leu Lys Asn Phe Thr Leu Glu
    210                 215                 220

Gly Lys Val Ala Asn Asp Lys Val Thr Leu Glu Val Lys Cys Gly Thr
225                 230                 235                 240

Val Thr Leu Ser Lys Glu Ile Ala Lys Ser Gly Glu Val Thr Val Ala
                245                 250                 255

Leu Asn Asp Thr Asn Thr Thr Arg Ala Thr Lys Lys Thr Gly Lys Trp
            260                 265                 270

Asp Ser Lys Thr Ser Thr Leu Thr Ile Ser Val Asn Ser Gln Lys Thr
        275                 280                 285

Lys Asn Leu Val Phe Thr Lys Glu Asp Thr Ile Thr Val Gln Asn Tyr
    290                 295                 300

Asp Ser Ala Gly Thr Asn Leu Glu Gly Ser Pro Ala Glu Ile Lys Asp
305                 310                 315                 320

Leu Ala Glu Leu Cys Ala Ala Leu Lys
                325

<210> SEQ ID NO 29
<211> LENGTH: 987
<212> TYPE: DNA
```

```
<213> ORGANISM: Artificial Sequence
<220> FEATURE:
<223> OTHER INFORMATION: Synthetic Polynucleotide

<400> SEQUENCE: 29
tgctcaagct tcaatgcaaa aggtgaactg agcgaaaaaa ccattctgcg tgcaaatggc     60
acccgtctgg aatataccga atcaaaagt gatggcaccg gtaaagcaaa agaagtgctg    120
aaagattttg cactggaagg caccgttgca gcagatggta agttaccct gaaagttacc    180
tgtggcaccg tgaccctgag caaaaacatt agcaaaagcg gtgaaattac cgttgccctg    240
gatgataccg atagcagcgc agcaaccaaa aaaaccgcag catgggatag cggcaccagc    300
accctgacca ttaccgttaa tagtaaaaaa accaaacagc tggtgtttac caaagaggat    360
accattacgg ttcagaacta tgatagcaat ggtacgaatc tggaaggtaa agccgttgaa    420
atcaccacac tgaaagaact gtgtaatgca ctgaaaggta ctagtgcaaa taatcaggca    480
ggtcagaaaa gcagcggtag cacccaggca accaccccga atctgacctt tgaaaagtac    540
tcatttaacg agaaaggcga gctgtcagca aaaaccatga cccgtgaaaa tggaaccaaa    600
ctggaataca cggaaatgaa atcagatggt acaggcaaag ccaaagaggt cctgaaaaac    660
ttcaccctgg aagggaaagt tgccaatgat aaagtgacac tggaagttaa atgtggtaca    720
gttacactga gcaaagaaat tgccaaatca ggtgaagtga ccgtggcact gaatgataca    780
aataccaccc gtgccacaaa aaaaacaggt aaatgggata gtaaaacgag cacactgaca    840
attagtgtga atagccagaa aacgaaaaac ctggtgttca cgaaagaaga tacaatcacc    900
gtacagaatt atgattcagc aggcaccaac ctggaaggtt caccggcaga aattaaagat    960
ctggccgaac tgtgtgcagc cctgaaa                                        987

<210> SEQ ID NO 30
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 30

Met Lys Ala Thr Lys Leu Val Leu Gly Ala Val Ile Leu Gly Ser Thr
1               5                   10                  15

Leu Leu Ala Gly Cys Ser Ser
            20

<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 31

His His His His His His
1               5

<210> SEQ ID NO 32
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 32
```

-continued

```
Ala Asn Asn Gln Ala Gly Gln Lys Ser Ser Gly Ser Thr Gln Ala Thr
1               5                   10                  15

Thr Pro Asn Leu Thr Phe Glu
            20
```

<210> SEQ ID NO 33
<211> LENGTH: 159
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 33

```
Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Leu Glu His His His His His
145                 150                 155
```

<210> SEQ ID NO 34
<211> LENGTH: 162
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 34

```
Leu Ile Pro Cys Ser Ser Phe Asn Glu Lys Gly Glu Leu Ser Ala Lys
1               5                   10                  15

Thr Met Thr Arg Glu Asn Gly Thr Lys Leu Glu Tyr Thr Glu Met Lys
            20                  25                  30

Ser Asp Gly Thr Gly Lys Ala Lys Glu Val Leu Lys Asn Phe Thr Leu
        35                  40                  45

Glu Gly Lys Val Ala Asn Asp Lys Val Thr Leu Glu Val Lys Cys Gly
50                  55                  60

Thr Val Thr Leu Ser Lys Glu Ile Ala Lys Ser Gly Glu Val Thr Val
65                  70                  75                  80

Ala Leu Asn Asp Thr Asn Thr Thr Gln Ala Thr Lys Lys Thr Gly Ala
                85                  90                  95
```

```
Trp Asp Ser Lys Thr Ser Thr Leu Thr Ile Ser Val Asn Ser Lys Lys
            100                 105                 110

Thr Thr Gln Leu Val Phe Thr Lys Gln Asp Thr Ile Thr Val Gln Lys
        115                 120                 125

Tyr Asp Ser Ala Gly Thr Asn Leu Glu Gly Thr Ala Val Glu Ile Lys
    130                 135                 140

Thr Leu Asp Glu Leu Cys Asn Ala Leu Lys Leu Glu His His His His
145                 150                 155                 160

His His

<210> SEQ ID NO 35
<211> LENGTH: 160
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 35

Cys Ser Ser Phe Asn Asp Lys Gly Lys Leu Ser Glu Lys Val Val Thr
1               5                   10                  15

Arg Ala Asn Gly Thr Arg Leu Glu Tyr Thr Glu Ile Lys Asn Asp Gly
            20                  25                  30

Ser Gly Lys Ala Lys Glu Val Leu Lys Gly Phe Ala Leu Glu Gly Thr
        35                  40                  45

Leu Thr Asp Gly Gly Glu Thr Lys Leu Thr Val Thr Cys Gly Thr Val
    50                  55                  60

Thr Leu Ser Lys Asn Ile Ser Lys Ser Gly Glu Ile Thr Val Ala Leu
65                  70                  75                  80

Asn Asp Thr Glu Thr Thr Pro Ala Asp Lys Lys Thr Gly Glu Trp Lys
                85                  90                  95

Ser Asp Thr Ser Thr Leu Thr Ile Ser Lys Asn Ser Gln Lys Pro Lys
            100                 105                 110

Gln Leu Val Phe Thr Lys Glu Asn Thr Ile Thr Val Gln Asn Tyr Asn
        115                 120                 125

Arg Ala Gly Asn Ala Leu Glu Gly Ser Pro Ala Glu Ile Lys Asp Leu
    130                 135                 140

Ala Glu Leu Cys Ala Ala Leu Lys Leu Glu His His His His His
145                 150                 155                 160

<210> SEQ ID NO 36
<211> LENGTH: 159
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 36

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr
        35                  40                  45
```

Leu Ala Ala Asp Lys Thr Thr Leu Lys Val Thr Cys Gly Thr Val Val
         50                  55                  60

Leu Ser Lys His Ile Pro Asn Ser Gly Glu Ile Thr Val Glu Leu Asn
 65                  70                  75                  80

Asp Ser Asn Ser Thr Gln Ala Thr Lys Lys Thr Gly Lys Trp Asp Ser
                 85                  90                  95

Asn Thr Ser Thr Leu Thr Ile Ser Val Asn Ser Lys Lys Thr Lys Asn
                100                 105                 110

Ile Val Phe Thr Lys Glu Asp Thr Ile Thr Val Gln Lys Tyr Asp Ser
            115                 120                 125

Ala Gly Thr Asn Leu Glu Gly Asn Ala Val Glu Ile Lys Thr Leu Asp
        130                 135                 140

Glu Leu Cys Asn Ala Leu Lys Leu Glu His His His His His His
145                 150                 155

<210> SEQ ID NO 37
<211> LENGTH: 159
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 37

Cys Ser Ser Phe Asn Glu Lys Gly Glu Ile Ser Glu Lys Thr Ile Val
 1               5                  10                  15

Arg Ala Asn Gly Thr Arg Leu Glu Tyr Thr Asp Ile Lys Ser Asp Lys
             20                  25                  30

Thr Gly Lys Ala Lys Glu Val Leu Lys Asp Phe Thr Leu Glu Gly Thr
         35                  40                  45

Leu Ala Ala Asp Gly Lys Thr Thr Leu Lys Val Thr Cys Gly Thr Val
     50                  55                  60

Thr Leu Ser Lys Asn Ile Ser Lys Ser Gly Glu Ile Thr Val Ala Leu
 65                  70                  75                  80

Asp Asp Thr Asp Ser Ser Gly Asn Lys Lys Ser Gly Thr Trp Asp Ser
                 85                  90                  95

Gly Thr Ser Thr Leu Thr Ile Ser Lys Asn Arg Thr Lys Thr Lys Gln
                100                 105                 110

Leu Val Phe Thr Lys Glu Asp Thr Ile Thr Val Gln Asn Tyr Asp Ser
            115                 120                 125

Ala Gly Thr Asn Leu Glu Gly Lys Ala Val Glu Ile Thr Thr Leu Lys
        130                 135                 140

Glu Leu Cys Asn Ala Leu Lys Leu Glu His His His His His His
145                 150                 155

<210> SEQ ID NO 38
<211> LENGTH: 160
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 38

Cys Ser Ser Phe Asn Gly Lys Gly Glu Thr Ser Glu Lys Thr Ile Val

```
                1               5                   10                  15
Arg Ala Asn Gly Thr Arg Leu Glu Tyr Thr Asp Ile Lys Ser Asp Gly
                20                  25                  30

Ser Gly Lys Ala Lys Glu Val Leu Lys Asp Phe Thr Leu Glu Gly Thr
                35                  40                      45

Leu Ala Ala Asp Gly Lys Thr Thr Leu Lys Val Thr Cys Gly Thr Val
            50                  55                  60

Val Leu Ser Lys Asn Ile Leu Lys Ser Gly Glu Ile Thr Ala Ala Leu
65                      70                  75                  80

Asp Asp Ser Asp Thr Thr Arg Ala Thr Lys Lys Thr Gly Lys Trp Asp
                    85                  90                  95

Ser Lys Thr Ser Thr Leu Thr Ile Ser Val Asn Ser Gln Lys Thr Lys
                100                 105                 110

Asn Leu Val Phe Thr Lys Glu Asp Thr Ile Thr Val Gln Arg Tyr Asp
                115                 120                 125

Ser Ala Gly Thr Asn Leu Glu Gly Lys Ala Val Glu Ile Thr Thr Leu
            130                 135                 140

Lys Glu Leu Cys Asn Ala Leu Lys Leu Glu His His His His His
145                 150                 155                 160
```

<210> SEQ ID NO 39
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 39

```
Lys Leu Lys Leu Leu Leu Leu Leu Lys Leu Lys
1               5                   10
```

<210> SEQ ID NO 40
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(26)
<223> OTHER INFORMATION: n=deoxyinosine

<400> SEQUENCE: 40 ncncncnc ncncncnc ncncnc                                         26

<210> SEQ ID NO 41
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 41

```
Phe Asn Glu Lys Gly Glu Val Ser Glu Lys Ile Leu Thr Arg Ser Asn
1               5                   10                  15

Gly Thr Thr Leu Glu Tyr Ser Gln Met Thr Asp Ala Glu Asn Ala Thr
                20                  25                  30

Lys Ala Val Glu Thr Leu Lys Asn Gly Ile Lys Leu Pro Gly Asn Leu
            35                  40                  45

Val Gly Gly Lys Thr Lys Leu Thr Val Thr Cys Gly Thr Val Thr Leu
        50                  55                  60
```

```
Ser Lys Asn Ile Ser Lys Ser Gly Glu Ile Thr Val Ala Leu Asn Asp
 65                  70                  75                  80

Thr Glu Thr Thr Pro Ala Asp Lys Lys Thr Gly Glu Trp Lys Ser Asp
                 85                  90                  95

Thr Ser Thr Leu Thr Ile Ser Lys Asn Ser Gln Lys Thr Lys Gln Leu
                100                 105                 110

Val Phe Thr Lys Glu Asn Thr Ile Thr Val Gln Asn Tyr Asn Arg Ala
            115                 120                 125

Gly Asn Ala Leu Glu Gly Ser Pro Ala Glu Ile Lys Asp Leu Ala Glu
        130                 135                 140

Leu Cys Ala Ala Leu Lys
145                 150

<210> SEQ ID NO 42
<211> LENGTH: 52
<212> TYPE: PRT
<213> ORGANISM: Borrelia valaisiana

<400> SEQUENCE: 42

Phe Asn Glu Lys Gly Glu Val Ser Glu Lys Ile Leu Thr Arg Ser Asn
 1               5                  10                  15

Gly Thr Thr Leu Glu Tyr Ser Gln Met Thr Asp Ala Glu Asn Ala Thr
                20                  25                  30

Lys Ala Val Glu Thr Leu Lys Asn Gly Ile Lys Leu Pro Gly Asn Leu
            35                  40                  45

Val Gly Gly Lys
    50

<210> SEQ ID NO 43
<211> LENGTH: 98
<212> TYPE: PRT
<213> ORGANISM: Borrelia garinii

<400> SEQUENCE: 43

Thr Lys Leu Thr Val Thr Cys Gly Thr Val Thr Leu Ser Lys Asn Ile
 1               5                  10                  15

Ser Lys Ser Gly Glu Ile Thr Val Ala Leu Asn Asp Thr Glu Thr Thr
                20                  25                  30

Pro Ala Asp Lys Lys Thr Gly Glu Trp Lys Ser Asp Thr Ser Thr Leu
            35                  40                  45

Thr Ile Ser Lys Asn Ser Gln Lys Thr Lys Gln Leu Val Phe Thr Lys
        50                  55                  60

Glu Asn Thr Ile Thr Val Gln Asn Tyr Asn Arg Ala Gly Asn Ala Leu
 65                  70                  75                  80

Glu Gly Ser Pro Ala Glu Ile Lys Asp Leu Ala Glu Leu Cys Ala Ala
                85                  90                  95

Leu Lys

<210> SEQ ID NO 44
<211> LENGTH: 274
<212> TYPE: PRT
<213> ORGANISM: Borrelia valaisiana

<400> SEQUENCE: 44

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
```

```
            20                  25                  30
Asp Leu Pro Gly Glu Met Lys Val Leu Val Ser Lys Glu Lys Asp Lys
         35                  40                  45

Asp Gly Lys Tyr Ser Leu Val Ala Thr Val Asp Lys Val Glu Leu Lys
     50                  55                  60

Gly Thr Ser Asp Lys Asn Asn Gly Ser Gly Thr Leu Glu Gly Val Lys
 65                  70                  75                  80

Asp Asp Lys Ser Lys Val Lys Leu Thr Ile Ser Asp Asp Leu Gly Glu
                 85                  90                  95

Thr Lys Leu Glu Thr Phe Lys Glu Asp Gly Thr Leu Val Ser Arg Lys
             100                 105                 110

Val Asn Phe Lys Asp Lys Ser Phe Thr Glu Glu Lys Phe Asn Glu Lys
         115                 120                 125

Gly Glu Val Ser Glu Lys Ile Leu Thr Arg Ser Asn Gly Thr Thr Leu
     130                 135                 140

Glu Tyr Ser Gln Met Thr Asp Ala Glu Asn Ala Thr Lys Ala Val Glu
145                 150                 155                 160

Thr Leu Lys Asn Gly Ile Lys Leu Pro Gly Asn Leu Val Gly Gly Lys
                 165                 170                 175

Thr Thr Leu Lys Ile Thr Glu Gly Thr Val Thr Leu Ser Lys His Ile
             180                 185                 190

Ala Lys Ser Gly Glu Val Thr Val Glu Ile Asn Asp Thr Ser Ser Thr
         195                 200                 205

Pro Asn Thr Lys Lys Thr Gly Lys Trp Asp Ala Arg Asn Ser Thr Leu
     210                 215                 220

Thr Ile Ile Val Asp Ser Lys Asn Lys Thr Lys Leu Val Phe Thr Lys
225                 230                 235                 240

Gln Asp Thr Ile Thr Val Gln Ser Tyr Asn Pro Ala Gly Asn Lys Leu
                 245                 250                 255

Glu Gly Thr Ala Val Glu Ile Lys Thr Leu Gln Glu Leu Lys Asn Ala
             260                 265                 270

Leu Lys

<210> SEQ ID NO 45
<211> LENGTH: 273
<212> TYPE: PRT
<213> ORGANISM: Borrelia spielmanii

<400> SEQUENCE: 45

Met Lys Lys Tyr Leu Leu Gly Ile Gly Leu Ile Leu Ala Leu Ile Ala
 1               5                  10                  15

Cys Lys Gln Asn Val Ser Gly Leu Asp Glu Lys Asn Ser Thr Ser Val
                 20                  25                  30

Asp Val Pro Gly Glu Leu Lys Val Leu Val Ser Lys Glu Lys Asp Lys
             35                  40                  45

Asp Gly Lys Tyr Ser Leu Met Ala Thr Val Asp Lys Leu Glu Leu Lys
         50                  55                  60

Gly Thr Ser Asp Lys Asn Asp Gly Ser Gly Val Leu Glu Gly Val Lys
 65                  70                  75                  80

Ala Asp Lys Ser Lys Val Lys Leu Thr Ile Ser Asp His Leu Ser Lys
                 85                  90                  95

Thr Thr Phe Glu Val Phe Lys Glu Asp Gly Lys Thr Leu Val Ser Arg
             100                 105                 110

Asn Val Asn Ser Lys Asp Lys Ser Ser Thr Lys Glu Lys Phe Asn Glu
```

```
            115                 120                 125
Lys Gly Glu Leu Ser Glu Lys Thr Leu Val Arg Ala Asn Gly Thr Lys
        130                 135                 140

Leu Glu Tyr Thr Glu Ile Lys Ser Asp Gly Thr Gly Lys Ala Lys Glu
145                 150                 155                 160

Val Leu Lys Asp Phe Thr Leu Glu Gly Thr Leu Ala Asn Glu Lys Ala
                165                 170                 175

Thr Leu Thr Val Lys Glu Gly Thr Val Thr Leu Ser Lys Asn Ile Asp
            180                 185                 190

Lys Ser Gly Glu Val Thr Val Ala Leu Asn Asp Thr Asp Ser Thr Ala
        195                 200                 205

Ala Thr Lys Lys Thr Gly Ala Trp Asp Ser Lys Thr Ser Thr Leu Thr
    210                 215                 220

Ile Thr Val Asn Ser Lys Lys Thr Lys Asp Leu Val Phe Thr Lys Gln
225                 230                 235                 240

Asp Thr Ile Thr Val Gln Lys Tyr Asp Ser Ala Gly Thr Thr Leu Glu
                245                 250                 255

Gly Ser Ala Val Glu Ile Lys Thr Leu Asp Glu Leu Lys Asn Ala Leu
            260                 265                 270

Lys

<210> SEQ ID NO 46
<211> LENGTH: 274
<212> TYPE: PRT
<213> ORGANISM: Borrelia garinii

<400> SEQUENCE: 46

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
                85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
    130                 135                 140

Leu Glu Tyr Thr Glu Ile Lys Asn Asp Gly Ser Gly Lys Ala Lys Glu
145                 150                 155                 160

Val Leu Lys Gly Phe Ala Leu Glu Gly Thr Leu Thr Asp Gly Gly Glu
                165                 170                 175

Thr Lys Leu Thr Val Thr Glu Gly Thr Val Thr Leu Ser Lys Asn Ile
            180                 185                 190

Ser Lys Ser Gly Glu Ile Thr Val Ala Leu Asn Asp Thr Glu Thr Thr
        195                 200                 205

Pro Ala Asp Lys Lys Thr Gly Glu Trp Lys Ser Asp Thr Ser Thr Leu
```

Thr Ile Ser Lys Asn Ser Gln Lys Thr Lys Gln Leu Val Phe Thr Lys
225                 230                 235                 240

Glu Asn Thr Ile Thr Val Gln Asn Tyr Asn Arg Ala Gly Asn Ala Leu
            245                 250                 255

Glu Gly Ser Pro Ala Glu Ile Lys Asp Leu Ala Glu Leu Ala Ala
            260                 265                 270

Leu Lys

<210> SEQ ID NO 47
<211> LENGTH: 1029
<212> TYPE: DNA
<213> ORGANISM: Artificial Sequence
<220> FEATURE:
<223> OTHER INFORMATION: Synthetic Polynucleotide

<400> SEQUENCE: 47

| | | | | | |
|---|---|---|---|---|---|
| atgaaagcta | ctaaactggt | actgggcgcg | gtaatcctgg | gttctactct | gctggcaggt | 60 |
| tgctcaagct | tcaatgctaa | gggcgaactg | agcgaaaaaa | cgatcctgcg | tgcgaatggc | 120 |
| acccgtctgg | aataccacga | aatcaaatcc | gatggtacgg | gcaaagcaaa | ggaagtcctg | 180 |
| aaagattttg | ctctggaagg | taccctggcg | ccgacaaaaa | ccacgctgaa | ggtgacgtgc | 240 |
| ggcaccgtgg | ttctgagcaa | acatattccg | aactctggtg | aaatcaccgt | tgaactgaac | 300 |
| gatagcaatt | ctacgcaggc | aaccaaaaag | acgggcaaat | gggacagtaa | tacctccacg | 360 |
| ctgaccattt | cagtcaactc | gaaaaagacc | aaaaatattg | tgttcacgaa | ggaagatacg | 420 |
| atcaccgttc | aaaatatga  | ctccgcgggc | accaacctgg | aaggcaatgc | cgtcgaaatc | 480 |
| aaaaccctgg | atgaactgtg | taacgccctg | aagggtacta | gtgacaaaaa | caatggctct | 540 |
| ggtagcaaag | agaaaaacaa | agatggcaag | tactcattca | cgaaaaagg  | cgaagtgagc | 600 |
| gaaaaaattc | tgacccgtag | caatggcacc | accctggaat | atagccagat | gaccgatgca | 660 |
| gaaaatgcaa | ccaaagcagt | tgaaaccctg | aaaaacggta | ttaaactgcc | tggtaatctg | 720 |
| gttggtggta | aaaccaaact | gaccgttacc | tgtggcaccg | ttaccctgag | caaaaacatt | 780 |
| agcaaaagcg | gtgaaattac | cgtggcactg | aatgataccg | aaaccacacc | ggcagacaaa | 840 |
| aaaccggtg  | aatggaaaag | cgataccagc | accctgacca | ttagtaaaaa | tagccagaaa | 900 |
| acaaaacagc | tggtgtttac | caaagaaaac | accattaccg | tgcagaatta | taaccgtgca | 960 |
| ggtaatgcac | tggaaggtag | tccggcagaa | attaaagatc | tggcagaact | gtgtgcagcc | 1020 |
| ctgaaataa |  |  |  |  |  | 1029 |

<210> SEQ ID NO 48
<211> LENGTH: 322
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 48

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30

Thr Gly Lys Ala Lys Glu Val Leu Lys Asp Phe Ala Leu Glu Gly Thr

```
                35                  40                  45
Leu Ala Ala Asp Lys Thr Thr Leu Lys Val Thr Cys Gly Thr Val Val
 50                  55                  60
Leu Ser Lys His Ile Pro Asn Ser Gly Glu Ile Thr Val Glu Leu Asn
 65                  70                  75                  80
Asp Ser Asn Ser Thr Gln Ala Thr Lys Lys Thr Gly Lys Trp Asp Ser
                 85                  90                  95
Asn Thr Ser Thr Leu Thr Ile Ser Val Asn Ser Lys Lys Thr Lys Asn
                100                 105                 110
Ile Val Phe Thr Lys Glu Asp Thr Ile Thr Val Gln Lys Tyr Asp Ser
            115                 120                 125
Ala Gly Thr Asn Leu Glu Gly Asn Ala Val Glu Ile Lys Thr Leu Asp
        130                 135                 140
Glu Leu Cys Asn Ala Leu Lys Gly Thr Ser Asp Lys Asn Asn Gly Ser
145                 150                 155                 160
Gly Ser Lys Glu Lys Asn Lys Asp Gly Lys Tyr Ser Phe Asn Glu Lys
                165                 170                 175
Gly Glu Val Ser Glu Lys Ile Leu Thr Arg Ser Asn Gly Thr Thr Leu
            180                 185                 190
Glu Tyr Ser Gln Met Thr Asp Ala Glu Asn Ala Thr Lys Ala Val Glu
        195                 200                 205
Thr Leu Lys Asn Gly Ile Lys Leu Pro Gly Asn Leu Val Gly Gly Lys
210                 215                 220
Thr Lys Leu Thr Val Thr Cys Gly Thr Val Thr Leu Ser Lys Asn Ile
225                 230                 235                 240
Ser Lys Ser Gly Glu Ile Thr Val Ala Leu Asn Asp Thr Glu Thr Thr
                245                 250                 255
Pro Ala Asp Lys Lys Thr Gly Glu Trp Lys Ser Asp Thr Ser Thr Leu
                260                 265                 270
Thr Ile Ser Lys Asn Ser Gln Lys Thr Lys Gln Leu Val Phe Thr Lys
            275                 280                 285
Glu Asn Thr Ile Thr Val Gln Asn Tyr Asn Arg Ala Gly Asn Ala Leu
        290                 295                 300
Glu Gly Ser Pro Ala Glu Ile Lys Asp Leu Ala Glu Leu Cys Ala Ala
305                 310                 315                 320
Leu Lys

<210> SEQ ID NO 49
<211> LENGTH: 1020
<212> TYPE: DNA
<213> ORGANISM: Artificial Sequence
<220> FEATURE:
<223> OTHER INFORMATION: Synthetic Polynucleotide

<400> SEQUENCE: 49
atgaaagcta ctaaactggt actgggcgcg gtaatcctgg ttctactctc gctggcaggt      60
tgctcaagct tcaacgaaaa gggcgaagtc agcgaaaaaa tcattacccg cgcagacggc     120
acccgcctgg aataccaccgg catcaaatcg gacggcagcg gcaaagcgaa agaagttctg    180
aaaaacttta ccctggaagg caagtcgcaa atgataaaa ccaccctggt ggtgaaatgc      240
ggcaccgtta cgctgagcaa aacattagt aaatccggtg aagtctctgt ggaactgaat      300
gataccgaca gctctgcggc caccaagaaa accgcagctt ggaactcagg cacctcgacg    360
ctgaccatta cggttaatag caagaaaacc aaagatctgg tcttcacgaa agaaaacacc    420
```

```
atcacggtgc agcaatatga cagcaatggt accaaactgg aaggctccgc tgtggaaatc    480
acgaaactgg atgaaatctg taatgctctg aaaggtacta gtgacaaaaa caatggctct    540
ggtagcaaag agaaaaacaa agatggcaag tactcattca cgaaaaaggg cgaactgtcg    600
gcgaaaacga tgacgcgtga aaacggcacc aaactggaat atacggaaat gaaaagcgat    660
ggcaccggta agcgaaaga agttctgaaa actttaccc tggaaggcaa agtcgccaat     720
gacaaagtca ccctggaagt gaatgcggc accgttacgc tgtcaaaaga aattgcaaaa    780
tcgggtgaag tgaccgttgc tctgaacgat acgaatacca cgcaagcgac caagaaaacc    840
ggcgcctggg acagcaaaac ctctacgctg accattagtg ttaatagcaa gaaaaccacg    900
cagctggtct tcaccaaaca agatacgatc accgtgcaga atacgacag tgcgggtacc     960
aacctggaag gcacggctgt tgaaatcaaa accctggacg aactgtgtaa cgccctgaaa   1020
```

<210> SEQ ID NO 50
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 50

Cys Ser Ser Phe Asn Glu Lys Gly Glu Val Ser Glu Lys Ile Ile Thr
1               5                   10                  15

Arg Ala Asp Gly Thr Arg Leu Glu Tyr Thr Gly Ile Lys Ser Asp Gly
            20                  25                  30

Ser Gly Lys Ala Lys Glu Val Leu Lys Asn Phe Thr Leu Glu Gly Lys
        35                  40                  45

Val Ala Asn Asp Lys Thr Thr Leu Val Val Lys Cys Gly Thr Val Thr
    50                  55                  60

Leu Ser Lys Asn Ile Ser Lys Ser Gly Glu Val Ser Val Glu Leu Asn
65                  70                  75                  80

Asp Thr Asp Ser Ser Ala Ala Thr Lys Lys Thr Ala Ala Trp Asn Ser
                85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240

Ser Gly Glu Val Thr Val Ala Leu Asn Asp Thr Asn Thr Thr Gln Ala

```
            245                 250                 255
Thr Lys Lys Thr Gly Ala Trp Asp Ser Lys Thr Ser Thr Leu Thr Ile
            260                 265                 270

Ser Val Asn Ser Lys Lys Thr Thr Gln Leu Val Phe Thr Lys Gln Asp
            275                 280                 285

Thr Ile Thr Val Gln Lys Tyr Asp Ser Ala Gly Thr Asn Leu Glu Gly
            290                 295                 300

Thr Ala Val Glu Ile Lys Thr Leu Asp Glu Leu Cys Asn Ala Leu Lys
305                 310                 315                 320
```

<210> SEQ ID NO 51
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 51

```
atgaaagcta ctaaactggt actgggcgcg gtaatcctgg gttctactct gctggcaggt    60
tgctcaagct tcaatgctaa gggcgaactg agcgaaaaaa cgatcctgcg tgcgaatggc   120
acccgtctgg aatacaccga atcaaatcc gatggtacgg gcaaagcaaa ggaagtcctg   180
aaagattttg ctctggaagg taccctggcg gccgacaaaa ccacgctgaa ggtgacgtgc   240
ggcaccgtgg ttctgagcaa acatattccg aactctggtg aaatcaccgt tgaactgaac   300
gatagcaatt ctacgcaggc aaccaaaaag acgggcaaat gggacagtaa tacctccacg   360
ctgaccattt cagtcaactc gaaaaagacc aaaaatattg tgttcacgaa ggaagatacg   420
atcaccgttc aaaaatatga ctccgcgggc accaacctgg aaggcaatgc cgtcgaaatc   480
aaaaccctgg atgaactgtg taacgccctg aagggtacta gtgacaaaaa caatggctct   540
ggtagcaaag agaaaaacaa agatggcaag tactcatttt acgataaggg caaactgtcg   600
gaaaaagtgg tcacccgcgc aaatggcacc cgcctggaat acacggaaat caaaaacgat   660
ggtagcggca agcgaagga agttctgaaa ggctttgccc tggaaggtac cctgacggat   720
ggcggtgaaa ccaaactgac cgtgacgtgc ggcaccgtta cgctgtctaa aaacattagc   780
aagtctggtg aaatcacggt cgcactgaat gataccgaaa ccacgccggc tgacaaaaag   840
accggcgaat ggaaaagtga cacctccacg ctgaccattt caaagaactc gcagaaaccg   900
aagcaactgg tcttcaccaa agaaaacacg atcaccgtgc agaactataa tcgtgccggt   960
aatgctctgg aaggctcacc ggctgaaatc aaggacctgg ctgaactgtg tgcggcactg  1020
aaa                                                                1023
```

<210> SEQ ID NO 52
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 52

```
Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30
```

Thr Gly Lys Ala Lys Glu Val Leu Lys Asp Phe Ala Leu Glu Gly Thr
                35                  40                  45

Leu Ala Ala Asp Lys Thr Thr Leu Lys Val Thr Cys Gly Thr Val Val
 50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
                100                 105                 110

Ile Val Phe Thr Lys Glu Asp Thr Ile Thr Val Gln Lys Tyr Asp Ser
                115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
                180                 185                 190

Glu Tyr Thr Glu Ile Lys Asn Asp Gly Ser Gly Lys Ala Lys Glu Val
            195                 200                 205

Leu Lys Gly Phe Ala Leu Glu Gly Thr Leu Thr Asp Gly Gly Glu Thr
    210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
                260                 265                 270

Ile Ser Lys Asn Ser Gln Lys Pro Lys Gln Leu Val Phe Thr Lys Glu
                275                 280                 285

Asn Thr Ile Thr Val Gln Asn Tyr Asn Arg Ala Gly Asn Ala Leu Glu
        290                 295                 300

Gly Ser Pro Ala Glu Ile Lys Asp Leu Ala Glu Leu Cys Ala Ala Leu
305                 310                 315                 320

Lys

<210> SEQ ID NO 53
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 53
atgaaagcta ctaaactggt actgggcgcg gtaatcctgg gttctactct gctggcaggt    60
tgctcaagct tcaacgaaaa gggcgaaatc tcagaaaaaa ccatcgtccg cgctaacggc   120
acccgcctgg aatacaccga catcaaatca gacaagaccg gtaaagcgaa ggaagttctg   180
aaagatttta cgctggaagg taccctggca gcagacggta aaaccacgct gaaggtgacc   240
tgcggtaccg ttacgctgtc caaaaacatt agtaagtccg gcgaaatcac ggtcgccctg   300
gatgacaccg atagctctgg caacaaaaag agcggtacct gggattcagg cacctcgacg   360
ctgaccattt ctaaaaatcg tacgaaaacc aagcagctgg tcttcacgaa agaagatacg   420

```
atcaccgtgc aaaactatga cagcgcaggt accaatctgg aaggcaaagc tgtggaaatt      480
accacgctga agaactgtg taatgctctg aaaggtacta gtgacaaaaa caatggctct       540
ggtagcaaag agaaaaacaa agatggcaag tactcattca acggcaaagg tgaaacgagc      600
gaaaagacca tcgtgcgtgc gaacggtacc cgcctggaat atacggacat taaatcggac      660
ggcagcggca agcaaagga agtcctgaaa gattttacgc tggaaggtac cctggcagca       720
gacggtaaaa ccacgctgaa ggtgacgtgc ggcaccgtgg ttctgtcaaa aaacattctg      780
aagtcgggtg aaatcaccgc agctctggat gacagcgata ccacgcgtgc tacgaaaaag      840
accggtaaat gggatagcaa gacctctacg ctgaccatta gtgtcaactc ccagaaaacg      900
aagaatctgg tgttcaccaa agaagatacg atcaccgttc aacgctatga cagtgcgggc      960
accaacctgg aaggcaaagc cgttgaaatt accacgctga agaactgtg taatgctctg      1020 aaa                                                                    1023
```

<210> SEQ ID NO 54
<211> LENGTH: 321
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 54

```
Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220

Thr Leu Lys Val Thr Cys Gly Thr Val Val Leu Ser Lys Asn Ile Leu
```

```
225                 230                 235                 240

Lys Ser Gly Glu Ile Thr Ala Ala Leu Asp Asp Ser Asp Thr Thr Arg
                245                 250                 255

Ala Thr Lys Lys Thr Gly Lys Trp Asp Ser Lys Thr Ser Thr Leu Thr
                260                 265                 270

Ile Ser Val Asn Ser Gln Lys Thr Lys Asn Leu Val Phe Thr Lys Glu
                275                 280                 285

Asp Thr Ile Thr Val Gln Arg Tyr Asp Ser Ala Gly Thr Asn Leu Glu
                290                 295                 300

Gly Lys Ala Val Glu Ile Thr Thr Leu Lys Glu Leu Cys Asn Ala Leu
305                 310                 315                 320

Lys

<210> SEQ ID NO 55
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 55

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
                20                  25                  30

Ala Lys Glu Val Leu Lys Asn Phe Thr Leu Glu Gly Lys Val Ala Asn
                35                  40                  45

Asp Lys Thr Thr Leu Val Val Lys Cys Gly Thr Val Thr Leu Ser Lys
            50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
                100                 105                 110

Thr Lys Glu Asn Thr Ile Thr Val Gln Gln Tyr Asp Ser Asn Gly Thr
            115                 120                 125

Lys Leu Glu Gly Ser Ala Val Glu Ile Thr Lys Leu Asp Glu Ile Cys
        130                 135                 140

Asn Ala Leu Lys
145

<210> SEQ ID NO 56
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 56

Phe Asn Glu Lys Gly Glu Leu Ser Ala Lys Thr Met Thr Arg Glu Asn
1               5                   10                  15

Gly Thr Lys Leu Glu Tyr Thr Glu Met Lys Ser Asp Gly Thr Gly Lys
                20                  25                  30

Ala Lys Glu Val Leu Lys Asn Phe Thr Leu Glu Gly Lys Val Ala Asn
                35                  40                  45

Asp Lys Val Thr Leu Glu Val Lys Cys Gly Thr Val Thr Leu Ser Lys
```

```
                    50                  55                  60
Glu Ile Ala Lys Ser Gly Glu Val Thr Val Ala Leu Asn Asp Thr Asn
 65                  70                  75                  80

Thr Thr Gln Ala Thr Lys Lys Thr Gly Ala Trp Asp Ser Lys Thr Ser
                     85                  90                  95

Thr Leu Thr Ile Ser Val Asn Ser Lys Lys Thr Thr Gln Leu Val Phe
                    100                 105                 110

Thr Lys Gln Asp Thr Ile Thr Val Gln Lys Tyr Asp Ser Ala Gly Thr
                115                 120                 125

Asn Leu Glu Gly Thr Ala Val Glu Ile Lys Thr Leu Asp Glu Leu Cys
            130                 135                 140

Asn Ala Leu Lys
145

<210> SEQ ID NO 57
<211> LENGTH: 149
<212> TYPE: PRT
<213> ORGANISM: Artificial Sequence
<220> FEATURE:
<223> OTHER INFORMATION: Synthetic Polypeptide

<400> SEQUENCE: 57

Phe Asn Asp Lys Gly Lys Leu Ser Glu Lys Val Val Thr Arg Ala Asn
 1               5                  10                  15

Gly Thr Arg Leu Glu Tyr Thr Glu Ile Lys Asn Asp Gly Ser Gly Lys
                20                  25                  30

Ala Lys Glu Val Leu Lys Gly Phe Ala Leu Glu Gly Thr Leu Thr Asp
             35                 40                 45

Gly Gly Glu Thr Lys Leu Thr Val Thr Cys Gly Thr Val Thr Leu Ser
         50                  55                  60

Lys Asn Ile Ser Lys Ser Gly Glu Ile Thr Val Ala Leu Asn Asp Thr
 65                 70                  75                  80

Glu Thr Thr Pro Ala Asp Lys Lys Thr Gly Glu Trp Lys Ser Asp Thr
                 85                 90                  95

Ser Thr Leu Thr Ile Ser Lys Asn Ser Gln Lys Thr Lys Gln Leu Val
                100                 105                 110

Phe Thr Lys Glu Asn Thr Ile Thr Val Gln Asn Tyr Asn Arg Ala Gly
                115                 120                 125

Asn Ala Leu Glu Gly Ser Pro Ala Glu Ile Lys Asp Leu Ala Glu Leu
            130                 135                 140

Cys Ala Ala Leu Lys
145

<210> SEQ ID NO 58
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 58

Phe Asn Ala Lys Gly Glu Leu Ser Glu Lys Thr Ile Leu Arg Ala Asn
 1               5                  10                  15

Gly Thr Arg Leu Glu Tyr Thr Glu Ile Lys Ser Asp Gly Thr Gly Lys
                20                  25                  30

Ala Lys Glu Val Leu Lys Asp Phe Ala Leu Glu Gly Thr Leu Ala Ala
             35                 40                 45
```

```
Asp Lys Thr Thr Leu Lys Val Thr Cys Gly Thr Val Val Leu Ser Lys
 50                  55                  60

His Ile Pro Asn Ser Gly Glu Ile Thr Val Glu Leu Asn Asp Ser Asn
 65                  70                  75                  80

Ser Thr Gln Ala Thr Lys Lys Thr Gly Lys Trp Asp Ser Asn Thr Ser
                 85                  90                  95

Thr Leu Thr Ile Ser Val Asn Ser Lys Lys Thr Lys Asn Ile Val Phe
            100                 105                 110

Thr Lys Glu Asp Thr Ile Thr Val Gln Lys Tyr Asp Ser Ala Gly Thr
            115                 120                 125

Asn Leu Glu Gly Asn Ala Val Glu Ile Lys Thr Leu Asp Glu Leu Cys
130                 135                 140

Asn Ala Leu Lys
145

<210> SEQ ID NO 59
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 59

Phe Asn Glu Lys Gly Glu Ile Ser Glu Lys Thr Ile Val Arg Ala Asn
 1               5                  10                  15

Gly Thr Arg Leu Glu Tyr Thr Asp Ile Lys Ser Asp Lys Thr Gly Lys
                20                  25                  30

Ala Lys Glu Val Leu Lys Asp Phe Thr Leu Glu Gly Thr Leu Ala Ala
             35                  40                  45

Asp Gly Lys Thr Thr Leu Lys Val Thr Cys Gly Thr Val Thr Leu Ser
 50                  55                  60

Lys Asn Ile Ser Lys Ser Gly Glu Ile Thr Val Ala Leu Asp Asp Thr
 65                  70                  75                  80

Asp Ser Ser Gly Asn Lys Lys Ser Gly Thr Trp Asp Ser Gly Thr Ser
                 85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
            115                 120                 125

Asn Leu Glu Gly Lys Ala Val Glu Ile Thr Thr Leu Lys Glu Leu Cys
130                 135                 140

Asn Ala Leu Lys
145

<210> SEQ ID NO 60
<211> LENGTH: 149
<212> TYPE: PRT
<213> ORGANISM: Artificial Sequence
<220> FEATURE:
<223> OTHER INFORMATION: Synthetic Polypeptide

<400> SEQUENCE: 60

Phe Asn Gly Lys Gly Glu Thr Ser Glu Lys Thr Ile Val Arg Ala Asn
 1               5                  10                  15

Gly Thr Arg Leu Glu Tyr Thr Asp Ile Lys Ser Asp Gly Ser Gly Lys
                20                  25                  30

Ala Lys Glu Val Leu Lys Asp Phe Thr Leu Glu Gly Thr Leu Ala Ala
             35                  40                  45
```

Asp Gly Lys Thr Thr Leu Lys Val Thr Cys Gly Thr Val Leu Ser
            50                  55                  60

Lys Asn Ile Leu Lys Ser Gly Glu Ile Thr Ala Ala Leu Asp Asp Ser
 65                  70                  75                  80

Asp Thr Thr Arg Ala Thr Lys Lys Thr Gly Lys Trp Asp Ser Lys Thr
                 85                  90                  95

Ser Thr Leu Thr Ile Ser Val Asn Ser Gln Lys Thr Lys Asn Leu Val
                100                 105                 110

Phe Thr Lys Glu Asp Thr Ile Thr Val Gln Arg Tyr Asp Ser Ala Gly
            115                 120                 125

Thr Asn Leu Glu Gly Lys Ala Val Glu Ile Thr Thr Leu Lys Glu Leu
        130                 135                 140

Cys Asn Ala Leu Lys
145

<210> SEQ ID NO 61
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 61

Phe Asn Glu Lys Gly Glu Val Ser Glu Lys Ile Leu Thr Arg Ser Asn
  1               5                  10                  15

Gly Thr Thr Leu Glu Tyr Ser Gln Met Thr Asp Ala Glu Asn Ala Thr
                 20                  25                  30

Lys Ala Val Glu Thr Leu Lys Asn Gly Ile Lys Leu Pro Gly Asn Leu
             35                  40                  45

Val Gly Gly Lys Thr Lys Leu Thr Val Thr Cys Gly Thr Val Thr Leu
         50                  55                  60

Ser Lys Asn Ile Ser Lys Ser Gly Glu Ile Thr Val Ala Leu Asn Asp
 65                  70                  75                  80

Thr Glu Thr Thr Pro Ala Asp Lys Lys Thr Gly Glu Trp Lys Ser Asp
                 85                  90                  95

Thr Ser Thr Leu Thr Ile Ser Lys Asn Ser Gln Lys Thr Lys Gln Leu
                100                 105                 110

Val Phe Thr Lys Glu Asn Thr Ile Thr Val Gln Asn Tyr Asn Arg Ala
            115                 120                 125

Gly Asn Ala Leu Glu Gly Ser Pro Ala Glu Ile Lys Asp Leu Ala Glu
        130                 135                 140

Leu Cys Ala Ala Leu Lys
145                 150

<210> SEQ ID NO 62
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 62

Phe Asn Glu Lys Gly Glu Val Ser Glu Lys Ile Leu Thr Arg Ser Asn
  1               5                  10                  15

Gly Thr Thr Leu Glu Tyr Ser Gln Met Thr Asp Ala Glu Asn Ala Thr
                 20                  25                  30

Lys Ala Val Glu Thr Leu Lys Asn Gly Ile Lys Leu Pro Gly Asn Leu

```
            35                  40                  45
Val Gly Gly Lys Thr Thr Leu Lys Ile Thr Cys Gly Thr Val Thr Leu
 50                  55                  60

Ser Lys His Ile Ala Lys Ser Gly Glu Val Thr Val Glu Ile Asn Asp
 65                  70                  75                  80

Thr Ser Ser Thr Pro Asn Thr Lys Lys Thr Gly Lys Trp Asp Ala Arg
                 85                  90                  95

Asn Ser Thr Leu Thr Ile Ile Val Asp Ser Lys Asn Lys Thr Lys Leu
                100                 105                 110

Val Phe Thr Lys Gln Asp Thr Ile Thr Val Gln Ser Tyr Asn Pro Ala
                115                 120                 125

Gly Asn Lys Leu Glu Gly Thr Ala Val Glu Ile Lys Thr Leu Gln Glu
            130                 135                 140

Leu Cys Asn Ala Leu Lys
145                 150

<210> SEQ ID NO 63
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 63

Phe Asn Glu Lys Gly Glu Leu Ser Glu Lys Thr Leu Val Arg Ala Asn
 1               5                  10                  15

Gly Thr Lys Leu Glu Tyr Thr Glu Ile Lys Ser Asp Gly Thr Gly Lys
                20                  25                  30

Ala Lys Glu Val Leu Lys Asp Phe Thr Leu Glu Gly Thr Leu Ala Asn
             35                  40                  45

Glu Lys Thr Lys Leu Thr Val Thr Cys Gly Thr Val Thr Leu Ser Lys
 50                  55                  60

Asn Ile Ser Lys Ser Gly Glu Ile Thr Val Ala Leu Asn Asp Thr Glu
 65                  70                  75                  80

Thr Thr Pro Ala Asp Lys Lys Thr Gly Glu Trp Lys Ser Asp Thr Ser
                 85                  90                  95

Thr Leu Thr Ile Ser Lys Asn Ser Gln Lys Thr Lys Gln Leu Val Phe
                100                 105                 110

Thr Lys Glu Asn Thr Ile Thr Val Gln Asn Tyr Asn Arg Ala Gly Asn
            115                 120                 125

Ala Leu Glu Gly Ser Pro Ala Glu Ile Lys Asp Leu Ala Glu Leu Cys
            130                 135                 140

Ala Ala Leu Lys
145

<210> SEQ ID NO 64
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 64

Phe Asn Glu Lys Gly Glu Leu Ser Glu Lys Thr Leu Val Arg Ala Asn
 1               5                  10                  15

Gly Thr Lys Leu Glu Tyr Thr Glu Ile Lys Ser Asp Gly Thr Gly Lys
                20                  25                  30
```

Ala Lys Glu Val Leu Lys Asp Phe Thr Leu Glu Gly Thr Leu Ala Asn
             35                  40                  45

Glu Lys Ala Thr Leu Thr Val Lys Cys Gly Thr Val Thr Leu Ser Lys
 50                  55                  60

Asn Ile Asp Lys Ser Gly Glu Val Thr Val Ala Leu Asn Asp Thr Asp
 65                  70                  75                  80

Ser Thr Ala Ala Thr Lys Lys Thr Gly Ala Trp Asp Ser Lys Thr Ser
                 85                  90                  95

Thr Leu Thr Ile Thr Val Asn Ser Lys Lys Thr Lys Asp Leu Val Phe
                100                 105                 110

Thr Lys Gln Asp Thr Ile Thr Val Gln Lys Tyr Asp Ser Ala Gly Thr
            115                 120                 125

Thr Leu Glu Gly Ser Ala Val Glu Ile Lys Thr Leu Asp Glu Leu Cys
    130                 135                 140

Asn Ala Leu Lys
145

<210> SEQ ID NO 65
<211> LENGTH: 16
<212> TYPE: PRT
<213> ORGANISM: Borrelia

<400> SEQUENCE: 65

Met Lys Lys Tyr Leu Leu Gly Ile Gly Leu Ile Leu Ala Leu Ile Ala
1               5                   10                  15

<210> SEQ ID NO 66
<211> LENGTH: 15
<212> TYPE: PRT
<213> ORGANISM: Borrelia

<400> SEQUENCE: 66

Met Arg Leu Leu Ile Gly Phe Ala Leu Ala Leu Ala Leu Ile Gly
1               5                   10                  15

<210> SEQ ID NO 67
<211> LENGTH: 20
<212> TYPE: PRT
<213> ORGANISM: Escherichia coli

<400> SEQUENCE: 67

Met Lys Ala Thr Lys Leu Val Leu Gly Ala Val Ile Leu Gly Ser Thr
1               5                   10                  15

Leu Leu Ala Gly
            20

<210> SEQ ID NO 68
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 68

Gly Thr Ser Asp Lys Asn Asn Gly Ser Gly Ser Lys Glu Lys Asn Lys
1               5                   10                  15

Asp Gly Lys Tyr Ser
            20

<210> SEQ ID NO 69
<211> LENGTH: 278

<212> TYPE: PRT
<213> ORGANISM: Artificial Sequence
<220> FEATURE:
<223> OTHER INFORMATION: Synthetic Polypeptide

<400> SEQUENCE: 69

```
Met Arg Leu Leu Ile Gly Phe Ala Leu Ala Leu Ile Gly Cys
1               5                   10                  15

Ala Gln Lys Gly Ala Glu Ser Ile Gly Ser Val Ser Val Asp Leu Pro
            20                  25                  30

Gly Glu Met Lys Val Leu Val Ser Lys Glu Lys Asp Lys Asn Gly Lys
        35                  40                  45

Tyr Asp Leu Ile Ala Thr Val Asp Lys Leu Glu Leu Lys Gly Thr Ser
    50                  55                  60

Asp Lys Asn Asn Gly Ser Gly Val Leu Glu Gly Val Lys Thr Asn Lys
65                  70                  75                  80

Ser Lys Val Lys Leu Thr Ile Ser Asp Asp Leu Gly Gln Thr Thr Leu
                85                  90                  95

Glu Val Phe Lys Glu Asp Gly Lys Thr Leu Val Ser Lys Lys Val Thr
            100                 105                 110

Ser Lys Asp Lys Ser Ser Thr Glu Glu Lys Phe Asn Glu Lys Gly Glu
        115                 120                 125

Val Ser Glu Lys Ile Ile Thr Met Ala Asp Gly Thr Arg Leu Glu Tyr
    130                 135                 140

Thr Gly Ile Lys Ser Asp Gly Thr Gly Lys Ala Lys Tyr Val Leu Lys
145                 150                 155                 160

Asn Phe Thr Leu Glu Gly Lys Val Ala Asn Asp Lys Thr Thr Leu Glu
                165                 170                 175

Val Lys Glu Gly Thr Val Thr Leu Ser Met Asn Ile Ser Lys Ser Gly
            180                 185                 190

Glu Val Ser Val Glu Leu Asn Asp Thr Asp Ser Ser Ala Ala Thr Lys
        195                 200                 205

Lys Thr Ala Ala Trp Asn Ser Lys Thr Ser Thr Leu Thr Ile Ser Val
    210                 215                 220

Asn Ser Lys Lys Thr Thr Gln Leu Val Phe Thr Lys Gln Asp Thr Ile
225                 230                 235                 240

Thr Val Gln Lys Tyr Asp Ser Ala Gly Thr Asn Leu Glu Gly Thr Ala
                245                 250                 255

Val Glu Ile Lys Thr Leu Asp Glu Leu Lys Asn Ala Leu Lys Leu Glu
            260                 265                 270

His His His His His His
        275
```

<210> SEQ ID NO 70
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 70

```
Met Arg Leu Leu Ile Gly Phe Ala Leu Ala Leu Ile Gly Cys
1               5                   10                  15

Ala Gln Lys Gly Ala Glu Ser Ile Gly Ser Val Ser Val Asp Leu Pro
            20                  25                  30

Gly Gly Met Lys Val Leu Val Ser Lys Glu Lys Asp Lys Asn Gly Lys
        35                  40                  45
```

```
Tyr Ser Leu Met Ala Thr Val Glu Lys Leu Glu Leu Lys Gly Thr Ser
    50                  55                  60

Asp Lys Asn Asn Gly Ser Gly Thr Leu Glu Gly Glu Lys Thr Asn Lys
 65                  70                  75                  80

Ser Lys Val Lys Leu Thr Ile Ala Glu Asp Leu Ser Lys Thr Thr Phe
                 85                  90                  95

Glu Ile Phe Lys Glu Asp Gly Lys Thr Leu Val Ser Lys Lys Val Thr
            100                 105                 110

Leu Lys Asp Lys Ser Ser Thr Glu Glu Lys Phe Asn Glu Lys Gly Glu
        115                 120                 125

Ile Ser Glu Lys Thr Ile Val Met Ala Asn Gly Thr Arg Leu Glu Tyr
    130                 135                 140

Thr Asp Ile Lys Ser Asp Lys Thr Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Thr Leu Ser Met Asn Ile Ser Lys Ser
            180                 185                 190

Gly Glu Ile Thr Val Ala Leu Asp Asp Thr Asp Ser Ser Gly Asn Lys
        195                 200                 205

Lys Ser Gly Thr Trp Asp Ser Asp Thr Ser Thr Leu Thr Ile Ser Lys
    210                 215                 220

Asn Ser Gln Lys Thr Lys Gln Leu Val Phe Thr Lys Glu Asn Thr Ile
225                 230                 235                 240

Thr Val Gln Asn Tyr Asn Arg Ala Gly Asn Ala Leu Glu Gly Ser Pro
                245                 250                 255

Ala Glu Ile Lys Asp Leu Ala Glu Leu Lys Ala Leu Lys Leu Glu
            260                 265                 270

His His His His His His
        275

<210> SEQ ID NO 71
<211> LENGTH: 279
<212> TYPE: PRT
<213> ORGANISM: Artificial Sequence
<220> FEATURE:
<223> OTHER INFORMATION: Synthetic Polypeptide

<400> SEQUENCE: 71

Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Val Ser Val Asp Leu Pro
                20                  25                  30

Gly Gly Met Thr Val Leu Val Ser Lys Glu Lys Asp Lys Asn Gly Lys
            35                  40                  45

Tyr Ser Leu Glu Ala Thr Val Asp Lys Leu Glu Leu Lys Gly Thr Ser
    50                  55                  60

Asp Lys Asn Asn Gly Ser Gly Thr Leu Glu Gly Glu Lys Thr Asn Lys
 65                  70                  75                  80

Ser Lys Val Lys Leu Thr Ile Ala Asp Asp Leu Ser Gln Thr Lys Phe
                 85                  90                  95

Glu Ile Phe Lys Glu Asp Ala Lys Thr Leu Val Ser Lys Lys Val Thr
            100                 105                 110

Leu Lys Asp Lys Ser Ser Thr Glu Glu Lys Phe Asn Glu Lys Gly Glu
        115                 120                 125
```

Thr Ser Glu Lys Thr Ile Val Met Ala Asn Gly Thr Arg Leu Glu Tyr
    130                 135                 140

Thr Asp Ile Lys Ser Asp Gly Ser Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Val Leu Ser Met Asn Ile Leu Lys Ser
                180                 185                 190

Gly Glu Ile Thr Val Ala Leu Asp Asp Ser Asp Thr Thr Gln Ala Thr
                195                 200                 205

Lys Lys Thr Gly Lys Trp Asp Ser Asn Thr Ser Thr Leu Thr Ile Ser
    210                 215                 220

Val Asn Ser Lys Lys Thr Lys Asn Ile Val Phe Thr Lys Glu Asp Thr
225                 230                 235                 240

Ile Thr Val Gln Lys Tyr Asp Ser Ala Gly Thr Asn Leu Glu Gly Asn
                245                 250                 255

Ala Val Glu Ile Lys Thr Leu Asp Glu Leu Lys Asn Ala Leu Lys Leu
                260                 265                 270

Glu His His His His His His
        275

<210> SEQ ID NO 72
<211> LENGTH: 320
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LIPID
<222> LOCATION: (1)..(1)

<400> SEQUENCE: 72

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
                20                  25                  30

Thr Gly Lys Ala Lys Glu Val Leu Lys Asp Phe Ala Leu Glu Gly Thr
            35                  40                  45

Leu Ala Ala Asp Lys Thr Thr Leu Lys Val Thr Cys Gly Thr Val Val
    50                  55                  60

Leu Ser Lys His Ile Pro Asn Ser Gly Glu Ile Thr Val Glu Leu Asn
65                  70                  75                  80

Asp Ser Asn Ser Thr Gln Ala Thr Lys Lys Thr Gly Lys Trp Asp Ser
                85                  90                  95

Asn Thr Ser Thr Leu Thr Ile Ser Val Asn Ser Lys Lys Thr Lys Asn
                100                 105                 110

Ile Val Phe Thr Lys Glu Asp Thr Ile Thr Val Gln Lys Tyr Asp Ser
                115                 120                 125

Ala Gly Thr Asn Leu Glu Gly Asn Ala Val Glu Ile Lys Thr Leu Asp
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Glu Lys Thr Leu Val Arg Ala Asn Gly Thr Lys Leu
                180                 185                 190

```
Glu Tyr Thr Glu Ile Lys Ser Asp Gly Thr Gly Lys Ala Lys Glu Val
        195                 200                 205

Leu Lys Asp Phe Thr Leu Glu Gly Thr Leu Ala Asn Glu Lys Thr Lys
    210                 215                 220

Leu Thr Val Thr Cys Gly Thr Val Thr Leu Ser Lys Asn Ile Ser Lys
225                 230                 235                 240

Ser Gly Glu Ile Thr Val Ala Leu Asn Asp Thr Glu Thr Thr Pro Ala
                245                 250                 255

Asp Lys Lys Thr Gly Glu Trp Lys Ser Asp Thr Ser Thr Leu Thr Ile
            260                 265                 270

Ser Lys Asn Ser Gln Lys Thr Lys Gln Leu Val Phe Thr Lys Glu Asn
        275                 280                 285

Thr Ile Thr Val Gln Asn Tyr Asn Arg Ala Gly Asn Ala Leu Glu Gly
    290                 295                 300

Ser Pro Ala Glu Ile Lys Asp Leu Ala Glu Leu Cys Ala Ala Leu Lys
305                 310                 315                 320

<210> SEQ ID NO 73
<211> LENGTH: 50
<212> TYPE: PRT
<213> ORGANISM: Borrelia spielmanii

<400> SEQUENCE: 73

Phe Asn Glu Lys Gly Glu Leu Ser Glu Lys Thr Leu Val Arg Ala Asn
1               5                   10                  15

Gly Thr Lys Leu Glu Tyr Thr Glu Ile Lys Ser Asp Gly Thr Gly Lys
            20                  25                  30

Ala Lys Glu Val Leu Lys Asp Phe Thr Leu Glu Gly Thr Leu Ala Asn
        35                  40                  45

Glu Lys
    50

<210> SEQ ID NO 74
<211> LENGTH: 273
<212> TYPE: PRT
<213> ORGANISM: Borrelia afzelii

<400> SEQUENCE: 74

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

```
Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 75
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 75

Leu Glu His His His His His His
1               5
```